United States Patent
Luttrull et al.

(10) Patent No.: US 12,377,283 B2
(45) Date of Patent: *Aug. 5, 2025

(54) SYSTEM AND PROCESS OF UTILIZING MICROWAVE ENERGY FOR TREATING BIOLOGICAL TISSUE

(71) Applicant: Ojai Retinal Technology, LLC, Los Angeles, CA (US)

(72) Inventors: Jeffrey K. Luttrull, Los Angeles, CA (US); David B. Chang, Tustin, CA (US); Benjamin W. L. Margolis, Oakland, CA (US)

(73) Assignee: Ojai Retinal Technology, LLC, Los Angeles, CA (US)

( * ) Notice: Subject to any disclaimer, the term of this patent is extended or adjusted under 35 U.S.C. 154(b) by 1075 days.

This patent is subject to a terminal disclaimer.

(21) Appl. No.: 17/336,200

(22) Filed: Jun. 1, 2021

(65) Prior Publication Data
US 2021/0346712 A1    Nov. 11, 2021

Related U.S. Application Data

(60) Division of application No. 16/039,779, filed on Jul. 19, 2018, now Pat. No. 11,077,318, which is a (Continued)

(51) Int. Cl.
*A61N 5/04*    (2006.01)
*A61B 18/12*    (2006.01)
(Continued)

(52) U.S. Cl.
CPC ........ *A61N 5/0603* (2013.01); *A61B 18/1206* (2013.01); *A61B 18/14* (2013.01);
(Continued)

(58) Field of Classification Search
CPC . A61N 5/00; A61N 5/02; A61N 5/022; A61N 5/025; A61N 5/0625; A61N 1/403;
(Continued)

(56) References Cited

U.S. PATENT DOCUMENTS 3,408,593 A    10/1968    Hurwitz, Jr.
4,048,011 A    9/1977    Kovin et al.
(Continued)

FOREIGN PATENT DOCUMENTS

DE    10 2010 022 760 A1    12/2011
WO    1997/017011 A1    5/1997
(Continued)

OTHER PUBLICATIONS

Yeow, J.T.W. et al.; Micromachined 2-D scanner for 3-D optical coherence tomography; Sensors and Actuators A: Physical, vol. 117, Issue 2, Jan. 14, 2005, pp. 331-340; Elsevier.
(Continued)

*Primary Examiner* — Joseph A Stoklosa
*Assistant Examiner* — Adam J Avigan
(74) *Attorney, Agent, or Firm* — KELLY & KELLEY, PLLC

(57) ABSTRACT

A process for heat treating biological tissue includes providing a plurality of energy emitters formed into an array. Treatment energy in the form of microwave energy is generated from the plurality of emitters and applied to target tissue. The treatment energy has energy and application parameters selected so as to raise the target tissue temperature sufficiently to create a therapeutic effect while maintaining an average temperature of the target tissue over several minutes at or below a predetermined temperature so as not to destroy or permanently damage the target tissue.

12 Claims, 49 Drawing Sheets

Related U.S. Application Data continuation-in-part of application No. 15/918,487, filed on Mar. 12, 2018, now Pat. No. 10,874,873, which is a continuation-in-part of application No. 15/629,002, filed on Jun. 21, 2017, now Pat. No. 10,278,863, and a continuation-in-part of application No. 15/583,096, filed on May 1, 2017, now Pat. No. 10,953,241, and a continuation-in-part of application No. 15/460,821, filed on Mar. 16, 2017, now abandoned, said application No. 16/039,779 is a continuation-in-part of application No. 15/460,821, filed on Mar. 16, 2017, now abandoned, said application No. 15/918,487 is a continuation-in-part of application No. 15/232,320, filed on Aug. 9, 2016, now Pat. No. 9,962,291, and a continuation-in-part of application No. 15/214,726, filed on Jul. 20, 2016, now Pat. No. 10,531,908, and a continuation-in-part of application No. 15/178,842, filed on Jun. 10, 2016, now Pat. No. 9,626,445, and a continuation-in-part of application No. 14/922,885, filed on Oct. 26, 2015, now Pat. No. 9,427,602, and a continuation-in-part of application No. 14/921,890, filed on Oct. 23, 2015, now Pat. No. 9,381,116, and a continuation-in-part of application No. 14/607,959, filed on Jan. 28, 2015, now Pat. No. 9,168,174, and a continuation-in-part of application No. 13/798,523, filed on Mar. 13, 2013, now Pat. No. 10,219,947, and a continuation-in-part of application No. 13/481,124, filed on May 25, 2012, now Pat. No. 9,381,115.

(51) Int. Cl.
*A61B 18/14* (2006.01)
*A61F 9/008* (2006.01)
*A61N 5/02* (2006.01)
*A61N 5/06* (2006.01)
*A61N 7/02* (2006.01)
*A61B 18/00* (2006.01)
*A61N 1/40* (2006.01)
*A61N 5/067* (2006.01)
*A61N 7/00* (2006.01)

(52) U.S. Cl.
CPC ...... *A61F 9/00817* (2013.01); *A61F 9/00821* (2013.01); *A61N 5/025* (2013.01); *A61N 5/045* (2013.01); *A61N 5/0625* (2013.01); *A61N 7/022* (2013.01); *A61B 2018/00005* (2013.01); *A61B 2018/0016* (2013.01); *A61B 2018/00494* (2013.01); *A61F 2009/00863* (2013.01); *A61N 1/403* (2013.01); *A61N 2005/0604* (2013.01); *A61N 2005/0608* (2013.01); *A61N 2005/0609* (2013.01); *A61N 2005/063* (2013.01); *A61N 2005/0651* (2013.01); *A61N 2005/0659* (2013.01); *A61N 2005/0662* (2013.01); *A61N 5/067* (2021.08); *A61N 2007/0043* (2013.01)

(58) Field of Classification Search
CPC . A61N 5/045; A61N 1/32; A61N 1/40; A61B 18/1815; A61B 2018/1861; A61F 9/0079; A61H 2201/0292; A61M 2205/3686
See application file for complete search history.

(56) References Cited

U.S. PATENT DOCUMENTS

| | | |
|---|---|---|
| 4,176,325 A | 11/1979 | Kajimura et al. |
| 4,194,114 A | 3/1980 | Pankratov et al. |
| 4,410,365 A | 10/1983 | Glukhovsky et al. |
| 4,556,051 A | 12/1985 | Maurer |
| 4,695,733 A | 9/1987 | Pesavento |
| 4,730,335 A | 3/1988 | Clark et al. |
| 4,791,634 A | 12/1988 | Miyake |
| 4,825,880 A | 5/1989 | Stauffer et al. |
| 4,865,029 A | 9/1989 | Pankratov et al. |
| 4,879,722 A | 11/1989 | Dixon et al. |
| 4,930,504 A | 6/1990 | Diamantopoulos et al. |
| 4,933,944 A | 6/1990 | McGraw |
| 4,935,931 A | 6/1990 | McGraw |
| 4,961,079 A | 10/1990 | Owens et al. |
| 4,967,416 A | 10/1990 | Esterowitz et al. |
| 5,037,421 A | 8/1991 | Boutacoff et al. |
| 5,067,951 A | 11/1991 | Greve |
| 5,085,492 A | 2/1992 | Kelsoe et al. |
| 5,088,803 A | 2/1992 | Buzawa |
| 5,147,354 A | 9/1992 | Boutacoff et al. |
| 5,348,002 A | 9/1994 | Caro |
| 5,372,595 A | 12/1994 | Gaasterland et al. |
| 5,394,199 A | 2/1995 | Flower |
| 5,430,756 A | 7/1995 | Hanihara |
| 5,520,680 A | 5/1996 | Shapshay et al. |
| 5,651,019 A | 7/1997 | Goldberg et al. |
| 5,982,789 A | 11/1999 | Marshall et al. |
| 6,047,216 A | 4/2000 | Carl et al. |
| 6,050,990 A | 4/2000 | Tankovich et al. |
| 6,066,128 A | 5/2000 | Bahmanyar et al. |
| 6,129,722 A | 10/2000 | Ruiz |
| 6,156,028 A | 12/2000 | Prescott |
| 6,208,769 B1 | 3/2001 | Pankratov |
| 6,222,869 B1 | 4/2001 | Marshall et al. |
| 6,259,952 B1 | 7/2001 | Sluijter et al. |
| 6,327,291 B1 | 12/2001 | Marshall |
| 6,377,599 B1 | 4/2002 | Marshall |
| 6,540,391 B2 | 4/2003 | Lanzetta et al. |
| 6,599,246 B1 | 7/2003 | Coffey et al. |
| 6,681,185 B1 | 1/2004 | Young et al. |
| 6,715,877 B2 | 4/2004 | Molebny |
| 6,733,490 B1 | 5/2004 | Falsini et al. |
| 6,813,942 B1 | 11/2004 | Vozhdaev et al. |
| 6,889,695 B2 | 5/2005 | Pankratov et al. |
| 6,942,655 B2 | 9/2005 | Peyman |
| 7,227,196 B2 | 6/2007 | Burgener, II et al. |
| 7,229,435 B2 | 6/2007 | Nakamura |
| 7,387,785 B1 | 6/2008 | Rudin et al. |
| 7,452,081 B2 | 11/2008 | Wiltberger et al. |
| 7,645,276 B2 | 1/2010 | Pankratov et al. |
| 7,763,828 B2 | 7/2010 | Talwar et al. |
| 7,766,903 B2 | 8/2010 | Blumenkranz et al. |
| 7,766,904 B2 | 8/2010 | McGowan, Sr. et al. |
| 7,771,417 B2 | 8/2010 | Telfair et al. |
| 7,909,816 B2 | 3/2011 | Buzawa |
| 8,007,702 B2 | 8/2011 | Gellman |
| 8,414,509 B2 | 4/2013 | Diederich et al. |
| 8,454,161 B2 | 6/2013 | Su et al. |
| 9,192,780 B2 | 11/2015 | McDaniel |
| 9,333,371 B2 | 5/2016 | Bean et al. |
| 9,561,357 B2 | 2/2017 | Hall et al. |
| 2002/0099363 A1 | 7/2002 | Woodward et al. |
| 2002/0120255 A1 | 8/2002 | Sotiropoulos et al. |
| 2002/0165525 A1 | 11/2002 | Nakamura |
| 2003/0078567 A1 | 4/2003 | Dorin et al. |
| 2004/0098070 A1 | 5/2004 | Mohr et al. |
| 2005/0049582 A1 | 3/2005 | DeBenedictis et al. |
| 2005/0069531 A1 | 3/2005 | Karageozian et al. |
| 2005/0176662 A1 | 8/2005 | Inana et al. |
| 2005/0222555 A1 | 10/2005 | Manstein |
| 2006/0173512 A1 | 8/2006 | Barolet et al. |
| 2007/0173793 A1 | 7/2007 | Rathjen |
| 2007/0213693 A1 | 9/2007 | Plunkett |
| 2008/0015553 A1 | 1/2008 | Zacharias |
| 2008/0076958 A1 | 3/2008 | Britva et al. |
| 2008/0086050 A1 | 4/2008 | Misic |
| 2009/0048586 A1 | 2/2009 | Krueger et al. |
| 2009/0093798 A1 | 4/2009 | Charles |
| 2009/0198309 A1 | 8/2009 | Gowda et al. |
| 2009/0276019 A1 | 11/2009 | Perez et al. |
| 2010/0049180 A1 | 2/2010 | Wells et al. |

(56) References Cited

U.S. PATENT DOCUMENTS

| | | |
|---|---|---|
| 2010/0068141 A1 | 3/2010 | Kaushal et al. |
| 2010/0082024 A1 | 4/2010 | Brannan et al. |
| 2010/0092424 A1 | 4/2010 | Sanghvi et al. |
| 2010/0100162 A1 | 4/2010 | Peyman |
| 2010/0152716 A1 | 6/2010 | Previn et al. |
| 2010/0168724 A1 | 7/2010 | Sramek et al. |
| 2010/0249760 A1 | 9/2010 | Blumenkranz et al. |
| 2010/0290007 A1 | 11/2010 | Van De Velde |
| 2011/0196350 A1 | 8/2011 | Friedman et al. |
| 2013/0085481 A1 | 4/2013 | Dick et al. |
| 2013/0110095 A1 | 5/2013 | Boxer Wachler |
| 2013/0110206 A1 | 5/2013 | Yee et al. |
| 2013/0116672 A1 | 5/2013 | Yee |
| 2013/0231721 A1 | 9/2013 | Omneuon |
| 2013/0317487 A1 | 11/2013 | Luttrull et al. |
| 2013/0317570 A1 | 11/2013 | Luttrull et al. |
| 2014/0074191 A1 | 3/2014 | Dunleavy |
| 2014/0121631 A1 | 5/2014 | Bean et al. |
| 2014/0148735 A1 | 5/2014 | Nau, Jr. |
| 2014/0194958 A1 | 7/2014 | Chabal et al. |
| 2014/0228824 A1 | 8/2014 | Yee et al. |
| 2014/0364927 A1 | 12/2014 | Fuller |
| 2015/0058204 A1 | 2/2015 | Dunleavy et al. |
| 2015/0157498 A1 | 6/2015 | Luttrull et al. |
| 2015/0217125 A1 | 8/2015 | Chornenky et al. |
| 2016/0082294 A1 | 3/2016 | Luttrull et al. |
| 2016/0220834 A1 | 8/2016 | Schwarz |
| 2016/0296374 A1 | 10/2016 | Luttrull et al. |
| 2016/0338757 A1 | 11/2016 | Luttrull et al. |
| 2016/0346126 A1 | 12/2016 | Luttrull et al. |
| 2016/0361572 A1 | 12/2016 | Slayton |
| 2017/0232269 A1 | 8/2017 | Uttrull et al. |
| 2017/0319383 A1 | 11/2017 | Luttrull et al. |

FOREIGN PATENT DOCUMENTS

| | | |
|---|---|---|
| WO | 2004/043234 A2 | 5/2004 |
| WO | 2006002949 A2 | 1/2006 |
| WO | 2006005038 A2 | 1/2006 |
| WO | 2007035855 A2 | 3/2007 |
| WO | 2007106521 A2 | 9/2007 |
| WO | 2011/050056 A2 | 4/2011 |
| WO | 2012/018385 A2 | 2/2012 |

OTHER PUBLICATIONS

Luttrull, JK et al.; Subthreshold diode micropulse panretinal photocoagulation for proliferative diabetic retinopathy Eye (2007), 1-6; Eye advance online publication Jan. 16, 2009.

Luttrull, J K et al.; Subthreshold diode micropulse photocoagulation for the treatment of clinically significant diabetic macular oedema; Br J Ophthalmol 2005; 89:74-80.

Luttrull, Jeffrey K., MD et al.; Serial Optical Coherence Tomography of Subthreshold Diode Laser Micropulse Photocoagulation for Diabetic Macular Edema; Ophthalmic Surgery, Lasers & Imaging; Sep./Oct. 2006; vol. 37, No. 5; pp. 370-377.

Uttrull, J K et al.; Subthreshold diode micropulse photocoagulation for the treatment of clinically significant diabetic macular oedema; Eye (2009) Macmillan Publishers Limited 2009.

Luttrull et al. Subthreshold diode micropulse panretinal photocoagulation for proliferative diabetic retinopathy. Eye (2007), 1-6 © 2007 Nature Publishing Group, www.nature.com/eye.

Small Beam Diameter Scanning Galvo Mirror Systems; Thorlabs; 1999-2013, 4 pgs.

Keller, Matthew D. et al.; Raman Spectroscopy for Cancer Diagnosis; www.spectroscopyonline.com; Nov. 2006 21(11); pp. 33-41 (including Reference (21) thereof).

International Search Report for PCT/US2015/0060836 mailing date Jan. 29, 2016.

Allingham RR, Damji KF, Freedman S, et al. Shields Textbook of Glaucoma, 6th Ed., 2010, Wolters Kluwer / Lippincott Williams & Wilkins, Philadelphia. ISBN-13: 978-0-7817-9585-2.

Danesh-Meyer HV, Levin LA. Glaucoma as a neurodegenerative disease. J Neuroophthalmol. Sep. 2015; 35 Suppl 1: S22-8.

Tian K, Shibata-Germanos S, Pahlitzsch M, Cordeiro MF. Current perspective of neuroprotection and glaucoma. Clin Ophthalmol. Nov. 11, 2015; 9: 2109-18.

Vujosevic S, Bottega E, Casciano M, et al. Microperimetry and fundus autofluorescence in diabetic macular edema. Subthreshold micropulse diode laser versus modified Early Treatment Diabetic Retinopathy Study Laser photocoagulation. Retina 2010; 30:908-16.

Lavinsky D, Cardillo JA, Melo, et al. Randomized clinical trial evaluating mETDRS versus normal or high-density micropulsephotocoagulation for diabetic macular edema. Invest Ophthalmol Vis Sci. Jun. 17, 2011; 52 (7): 4314-23.

Luttrull JK, Spink CJ, Musch DA. Subthreshold diode micropulse panretinal photocoagulation for proliferative diabetic retinopathy. Eye, May 2008; 22 (5): 607-12.

Luttrull JK, Sramek C, Palanker D, Spink CJ, Musch DC. Long-term safety, high-resolution imaging, and tissue temperature modeling of subvisible diode micropulse photocoagulation for retinovascular macular edema. Retina 2012: 32 (2): 375-86.

Malik KJ1, Sampat KM, Mansouri A, Steiner JN, Glaser BM. Low-intensity/high-density subthreshold microPulse diode laser for chronic central serous chorioretinopathy. Retina. Mar. 2015;35(3):532-6.

Luttrull, JK. Low-Intensity/High-Density Subthreshold diode micropulse laser (SDM) for central serous chorioretinopathy. Retina, Jan. 2016 (in press).

Luttrull JK, Dorin G. Subthreshold diode micropulse photocoagulation as invisible retinal phototherapy for diabetic macular edema. A review. Current Diabetes Reviews, 2012, 8, 274-284.

Luttrull JK, Chang DB, Margolis BWL, Dorin G, Luttrull DK. Laser re-sensitization of medically unresponsive neovascular age-related macular degeneration: Efficacy and implications. Retina Jun. 2015; 35(6): 1184-1194.

Uttrull JK, Margolis BWL. Functionally guided retinal protective therapy as prophylaxis for age-related and inherited retinal degenerations. A pilot study. Invest Ophthalmol Vis Sci. Jan. 1, 2016;57(1):265-75. doi: 10.1167/iovs.15-18163.

McCulloch DL, Marmor MF, Brigell MG, et al. ISCEV Standard for full-field clinical electroretinography (2015 update). Doc Ophthalmol. Feb. 2015; 130 (1): 1-12.

Porciatti V, Ventura LM. Normative Data for a User-friendly Paradigm for Pattern Electroretinogram Recording. Ophthalmology, 2004; 111(1): 161-168.

Gutstein W, Sinclair SH, Presti P, North RV. Interactive thresholding of central acuity under contrast and luminance conditions mimicking real world environments: 1. Evaluation against LogMAR charts. J Comput Sci Sys Bio, 20125; 8(4) 225-232.

Parisi V, Centofanti M, Ziccardi L, et al. Treatment with citicoline drops enhances retinal function and neural conduction along the visual pathways in open angle glaucoma. Graefes Arch Clin Exp Ophthamol, May 2015; DOI 10.1007/s00417-015-3044-9.

Miller NR, ed. Walsh and Hoyt's Clinical Neurophthalmology. 4th Ed, 1985; Chapter 3: 41-60.Williams and Wilkins, Baltimore Maryland.

Salomão SR, Berezovsky A, Andrade RE, et al. Visual electrophysiologic findings in patients from an extensive Brazilian family with Leber'shereditary optic neuropathy. Doc Ophthalmol. Mar. 2004;108(2):147-55.

Kolomeyer AM, Zarbin MA. Trophic factors in the pathogenesis and therapy for retinal degenerative diseases. Surv Ophthalmol. Mar.-Apr. 2014;59 (2):134-65.

Kenealey J, Subramanian P, Comitato A, et al. Small Retinoprotective Peptides Reveal a Receptor-binding Region on Pigment Epithelium-derived Factor. J Biol Chem. Oct. 16, 2015;290(42):25241-53.

Yu PK1, Cringle SJ, McAllister IL, Yu DY. Low power laser treatment of the retina ameliorates neovascularisation in a transgenic mouse model of retinalneovascularisation. Exp Eye Res. Nov. 2009;89(5):791-800.

Flaxel C1, Bradle J, Acott T, Samples JR. Retinal pigment epithelium produces matrix metalloproteinases after laser treatment. Retina. Jun. 2007;27 (5):629-34.

(56) References Cited

OTHER PUBLICATIONS

Sramek C, Mackanos M, Spitler R, et al. Non-damaging retinal phototherapy: dynamic range of heat shock protein expression. Invest Ophthalmol Vis Sci. Mar. 28, 2011; 52 (3):1780-7.
Ventura LM, Feuer WJ, Porciatti V. Progressive loss of retinal ganglion cell function is hindered with IOP-lowering treatment in early glaucoma. IOVS, Feb. 2012 53 (2): 659-663.
Ventura LM, Porciatti V. Restoration of retinal ganglion cell function in early glaucoma after intraocular pressure reduction. A pilot study. Ophthalmology 2005, 112 (1): 20-27.
Yap GH, Chen LY, Png R, et al. Clinical value of electrophysiology in determining the diagnosis of visual dysfunction in neuro-ophthalmology patients. Doc Ophthalmol. Dec. 2015;131(3):189-96.
Waisbourd M, Ahmed OM, Molineaux J, et al. Reversible structural and functional changes after intraocular pressure reduction in patients with glaucoma. Graefes Arch Clin Exp Ophthalmol. Mar. 16, 2016. [Epub ahead of print] PMID: 26995555.
Banitt MR, Ventura LM, Feuer WJ, Savatovsky E, et al. Progressive loss of retinal ganglion cell function precedes structural loss by several years in glaucoma suspects. IOVS, Mar. 2013; 54 (3): 2346-2352.
Karu T. Photobiology of low-power laser effects. Review. Health Phys. May 1989; 56 (5): 691-704.
Gao X, Xing D. Molecular mechanisms of cell proliferation induced by low power laser irradiation. J Biomed Sci. Jan. 12, 2009;16:4.
Dorin G, Luttrull JK, Samples JR. Chapter 21: Laser alteration of collector channel ostia. Pivotal paradigm shift from photocoagulation to photostimulation. Glaucoma Research and Clinical Advances: 2016 to 2018. Knepper and Samples, Eds. Kugler Pub. Jan. 1, 2016, Amsterdam, Netherlands. ISBN: 9789062992478.

Van Teijlingen ER1, Rennie AM, Hundley V, Graham W. The importance of conducting and reporting pilot studies: the example of the Scottish Births Survey. J Adv Nurs. May 2001; 34 (3): 289-95.
Luttrull JK, Sinclair SH. Safety of transfoveal subthreshold diode micropulse laser (SDM) for fovea-involving diabetic macular edema in eyes with good visual acuity. Retina. Oct. 2014; 34 (10): 2010-20.
Luttrull, JK and Margolis BWL. improved retinal function following SDM laser for chronic disease. American Society of Retina Specialists Annual Meeting Vienna, Austria. Jul. 11, 2015 [online]. [retrieved on Jan. 11, 2017] KURL: http://www.diopsys.com/wp-content/uploads/2015/07/Luttrutl_Improved-retinal-function-following-SDM-laser-for-chronic-disease_ASRS2015.pdf>.
International Search Report for the International application No. PCT/US2016/46043 mailing date of Dec. 27, 2016.
International Search Report for International Application No. PCT/US2016/62421 mailing date Feb. 7, 2017.
International Search Report for the International Application No. PCT/US2017/44337 mailing date of Jan. 9, 2018.
International Search Report for the International Application No. PCT/US2015/60893, Mailing date Mar. 18, 2016.
Westerheide, Sandy D. et al.; Heat Shock Response Modulators as Therapeutic Tools for Diseases of Protein Conformation; Minireview; Journal of Biological Chemistry; vol. 280, No. 39, pp. 33097-33100, Sep. 30, 2005.
Najarzadegan, Mohammad Reza et al.; The Role of Heat Shock Proteins in Alzheimer Disease: A Systematic Review; Avens Publishing Group; J Syndromes; vol. 3, Issue 1; 6 pgs.; May 2016.
International Search Report for the International Application No. PCT/US2017/064708, Mailing date Feb. 9, 2018.
International Search Report for the International Application No. PCT/US2017/044319, Mailing date Jan. 11, 2018.
International Search Report for the International Application No. PCT/US2018/22201, Mailing date Jun. 1, 2018.
International Search Report for the International Application No. PCT/US2018/042903 mailing date of Sep. 24, 2018.

SYSTEM AND PROCESS OF UTILIZING MICROWAVE ENERGY FOR TREATING BIOLOGICAL TISSUE

RELATED APPLICATIONS

This application is a divisional of U.S. application Ser. No. 16/039,779 filed Jul. 19, 2018, which is a continuation-in-part of U.S. application Ser. No. 15/918,487 filed Mar. 12, 2018, which is a continuation-in-part of U.S. application Ser. No. 15/629,002 filed Jun. 21, 2017, Ser. No. 15/583,096 filed May 1, 2017, Ser. No. 15/460,821 filed Mar. 16, 2017, Ser. No. 15/232,320 filed Aug. 9, 2016 (now U.S. Pat. No. 9,962,291), Ser. No. 15/214,726 filed Jul. 20, 2016, Ser. No. 15/178,842 filed Jun. 10, 2016 (now U.S. Pat. No. 9,626,445), Ser. No. 14/922,885 filed Oct. 26, 2015 (now U.S. Pat. No. 9,427,602), Ser. No. 14/921,890 filed Oct. 23, 2015 (now U.S. Pat. No. 9,381,116), Ser. No. 14/607,959 filed Jan. 28, 2015 (now U.S. Pat. No. 9,168,174), Ser. No. 13/798,523 filed Mar. 13, 2013, and Ser. No. 13/481,124 filed May 25, 2012. This application is also a continuation-in-part of U.S. application Ser. No. 15/460,821, filed Mar. 16, 2017.

BACKGROUND OF THE INVENTION

The present invention is generally directed to systems and processes for treating biological tissue, such as diseased biological tissue. More particularly, the present invention is directed to a process for heat treating biological tissue using energy having parameters and applied such so as to create a therapeutic effect to a target tissue without destroying or permanently damaging the target tissue.

The inventors have discovered that there is a therapeutic effect to biological tissue, and particularly damaged or diseased biological tissue, by controllably elevating the tissue temperature up to a predetermined temperature range while maintaining the average temperature rise of the tissue over several minutes at or below a predetermined level so as not to permanently damage the target tissue. More particularly, the inventors have discovered that electromagnetic radiation, such as in the form of various wavelengths of light, can be applied to retinal tissue in a manner that does not destroy or damage the retinal tissue while achieving beneficial effects on eye diseases. The inventors have found that a light beam can be generated and applied to the retinal tissue cells such that it is therapeutic, yet sublethal to retinal tissue cells and thus avoids damaging photocoagulation in the retinal tissue which provides preventative and protective treatment of the retinal tissue of the eye. The treatment typically entails applying a train of laser micropulses to radiate a portion of a diseased retina for a total duration of less than a second. Each micropulse is on the order of tens to hundreds of microseconds long, with the microseconds being separated by one to several milliseconds, which raises the tissue temperature in a controlled manner.

It is believed that raising the tissue temperature in such a controlled manner selectively stimulates heat shock protein activation and/or production and facilitation of protein repair, which serves as a mechanism for therapeutically treating the tissue. It is believed that this micropulse train thermally activates heat shock proteins (HSPs) in the targeted tissue. In the case of retinal tissue, the process thermally activates HSPs in the retinal pigment epithelium (RPE) layer immediately behind the retinal layer containing the visually sensitive rods and cones, and that these activated HSPs then reset the diseased retina to its healthy condition by removing and repairing damaged proteins. This then results in improved RPE function, improves retinal function and autoregulation, restorative acute inflammation, reduced chronic inflammation, and systematic immunodulation. These laser-triggered effects then slow, stop or reverse retinal disease, improve visual function and reduce the risk of visual loss. It is believed that raising tissue temperature in such a controlled manner to selectively stimulate heat shock protein activation has benefits in other tissues as well.

HSPs are a family of proteins that are produced by cells in response to exposure to stressful conditions. Production of high levels of heat shock proteins can be triggered by exposure to different kinds of environmental stress conditions, such as infection, inflammation, exercise, exposure of the cell to toxins, oxidants, heavy metals, starvation, hypoxia, water deprivation and tissue trauma.

It is known that heat shock proteins play a role in responding to a large number of abnormal conditions in body tissues, including viral infection, inflammation, malignant transformations, exposure to oxidizing agents, cytotoxins, and anoxia. Several heat shock proteins function as intra-cellular chaperones for other proteins and members of the HSP family are expressed or activated at low to moderate levels because of their essential role in protein maintenance and simply monitoring the cell's proteins even under non-stressful conditions. These activities are part of a cell's own repair system, called the cellular stress response or the heat-shock response.

Heat shock proteins are found in nearly every cell and tissue-type of multicellular organisms as well as in explanted tissues and in cultured cells. The HSPs typically comprise 3%-10% of a cell's proteins, although when under stress the percentage can rise to 15%. The density of proteins of a mammalian cells has been found to be in the range of $(2\text{-}4) \times 10^{18} CM^{-3}$. Thus, the aforementioned percentages mean that the density of HSPs is normally $(1\text{-}4) \times 10^{17} CM^{-3}$, while under stress the density can rise to $(3\text{-}6) \times 10^{17} CM^{-3}$.

Heat shock proteins are typically named according to their molecular weight, and act in different ways. An especially ubiquitous heat shock protein is Hsp70, a protein with a molecular weight of 70 kilodaltons. It plays a particularly significant role in protecting proteins that are just being formed and in rescuing damaged proteins. It contains a groove with an affinity for neutral, hydrophobic amino acid residues that can interact with peptides up to 7 residues in length. Hsp70 has peptide-binding and ATPase domains that stabilize protein structures in unfolded and assembly-competent states. The HSPs play a role in preventing aggregation of misfolded proteins, many of which have exposed hydrophobic portions, and a facilitating the refolding of proteins into their proper conformations. Hsp70 accomplishes this by first binding to the misfolded or fragmented protein, a binding that is made energetically possible by a site that binds ATP and hydrolyzes it into ADP.

Hsp70 heat shock proteins are a member of extracellular and membrane bound heat-shock proteins which are involved in binding antigens and presenting them to the immune system. Hsp70 has been found to inhibit the activity of influenza A virus ribonucleoprotein and to block the replication of the virus. Heat shock proteins derived from tumors elicit specific protective immunity. Experimental and clinical observations have shown that heat shock proteins are involved in the regulation of autoimmune arthritis, type 1 diabetes, mellitus, arterial sclerosis, multiple sclerosis, and other autoimmune reactions.

Accordingly, it is believed that it is advantageous to be able to selectively and controllably raise a target tissue temperature up to a predetermined temperature range over a short period of time, while maintaining the average temperature rise of the tissue at a predetermined temperature over a longer period of time. It is believed that this induces the heat shock response in order to increase the number or activity of heat shock proteins in body tissue in response to infection or other abnormalities. However, this must be done in a controlled manner in order not to damage or destroy the tissue or the area of the body being treated. It would also be desirable to maximize the amount of heat shock protein activation within the cells of a targeted tissue during a single treatment session. The present invention fulfills these needs, and provides other related advantages.

SUMMARY OF THE INVENTION

The present invention is directed to a process for heat treating biological tissues by applying treatment energy to a target tissue to therapeutically treat the target tissue. A first treatment to the target tissue is performed by generating treatment energy and repeatedly applying the treatment energy to the target tissue over a period of time so as to controllably raise a temperature of the target tissue to therapeutically treat the target tissue without destroying or permanently damaging the target tissue. The generated treatment energy may be pulsed or rapidly applied in succession. The target tissue may comprise retinal tissue.

The energy parameters are selected so as to raise a target tissue temperature up to 11° C. to achieve a therapeutic effect, wherein the average temperature rise of the tissue over several minutes is maintained at or below a predetermined level so as not to permanently damage the target tissue. The energy parameters may be selected so that the target tissue temperature is raised between approximately 6° C. to 11° C. at least during application of the energy to the target tissue. The average temperature rise of the target tissue over several minutes is maintained at 6° C. or less, such as at approximately 1° C. or less over several minutes.

The treatment energy and application parameters are selected such so as to therapeutically treat the target tissue without destroying or permanently damaging the target tissue. The selected energy and application parameters may comprise tissue application spot size or area, average power or average power density, and exposure duration. Other parameters which may be selected include wavelength or frequency and duty cycle. For example, the treatment energy and application parameters may be selected to have an average power density of 100-590 watts per square centimeter of target tissue, a target tissue application spot size between 100-500 microns, and a train exposure duration of 500 milliseconds or less.

The treatment energy may comprise a light beam, a microwave, a radiofrequency or an ultrasound. A device may be inserted into a cavity of the body in order to apply the treatment energy to the tissue. The treatment energy may be applied to an exterior area of a body which is adjacent to the target tissue, or has a blood supply close to a surface of the exterior area of the body.

The treatment energy may comprise a radiofrequency between approximately 3 to 6 megahertz (MHz). It may have a duty cycle of between approximately 2.5% to 5%. It may have a pulsed train duration of between approximately 0.2 to 0.4 seconds. The radiofrequency may be generated with a device having a coil radii of between approximately 2 and 6 mm and approximately 13 and 57 amp turns.

The treatment energy may comprise a microwave frequency of between 10 to 20 gigahertz (GHz). The microwave may have a pulse train duration of approximately between 0.2 and 0.6 seconds. The microwave may have a duty cycle of between approximately 2% and 5%. The microwave may have an average power of between approximately 8 and 52 watts.

The treatment energy may comprise a pulsed light beam, such as one or more laser light beams. The light beam may have a wavelength of between approximately 570 nm to 1300 nm, and more preferably between 600 nm and 1000 nm. The pulsed light beam may have a power of between approximately 0.5 and 74 watts. The pulsed light beam has a duty cycle of less than 10%, and preferably between 2.5% and 5%. The pulsed light beam may have a pulse train duration of approximately 0.1 and 0.6 seconds.

The treatment energy may comprise a pulsed ultrasound, having a frequency of between approximately 1 and 5 MHz. The ultrasound has a train duration of approximately 0.1 and 05 seconds. The ultrasound may have a duty cycle of between approximately 2% and 10%. The ultrasound has a power of between approximately 0.46 and 28.6 watts.

The process of the present invention may comprise the steps of providing a plurality of energy emitters formed into an array. Treatment energy is generated from the plurality of emitters. The treatment energy is applied to the target tissue, wherein the treatment energy has energy and application parameters selected so as to raise the target tissue temperature sufficiently to create a therapeutic effect while maintaining an average temperature of the target tissue over several minutes at or below a predetermined temperature so as not to destroy or permanently damage the target tissue.

The first treatment comprises applying the treatment energy to the target tissue for a period of less than ten seconds, and more typically less than one second. The first treatment creates a level of heat shock protein activation in the target tissue. The application of the treatment energy to the target tissue is halted for an interval of time that preferably exceeds the period of time of the first treatment. The interval of time may comprise several seconds to several minutes, such as three seconds to three minutes, or preferably between ten seconds to ninety seconds. After the interval of time and within a single treatment session, a second treatment is performed to the target tissue by repeatedly reapplying the treatment energy to the target tissue so as to controllably raise the temperature of the target tissue to therapeutically treat the target tissue without destroying or permanently damaging the target tissue. The second treatment increases the level of heat shock protein activation in the target tissue such that it is at a level which is higher than the level after the first treatment.

During an interval of time, typically comprising less than one second, between applications of treatment energy applied to a first area of the target tissue, the treatment energy may be applied to a second area of the target tissue sufficiently spaced apart from the first area of the target tissue to avoid thermal tissue damage of the target tissue. The treatment energy is repeatedly applied, in an alternating manner during the same treatment session, to each of the first and second areas of the target tissue until the predetermined number of energy applications to each of the first and second areas of the target tissue has been achieved.

When utilizing an array, a phase delay in the activation of the energy emitters of the array may be introduced to generate treatment energy in a phased manner using a predetermined delay of activation in order to apply treatment energy to each of the first and second areas of the target tissue. Alternatively, the energy emitters of the array may be activated sequentially in order to apply treatment energy to each of the first and second areas of the target tissue.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

Figure 1A:
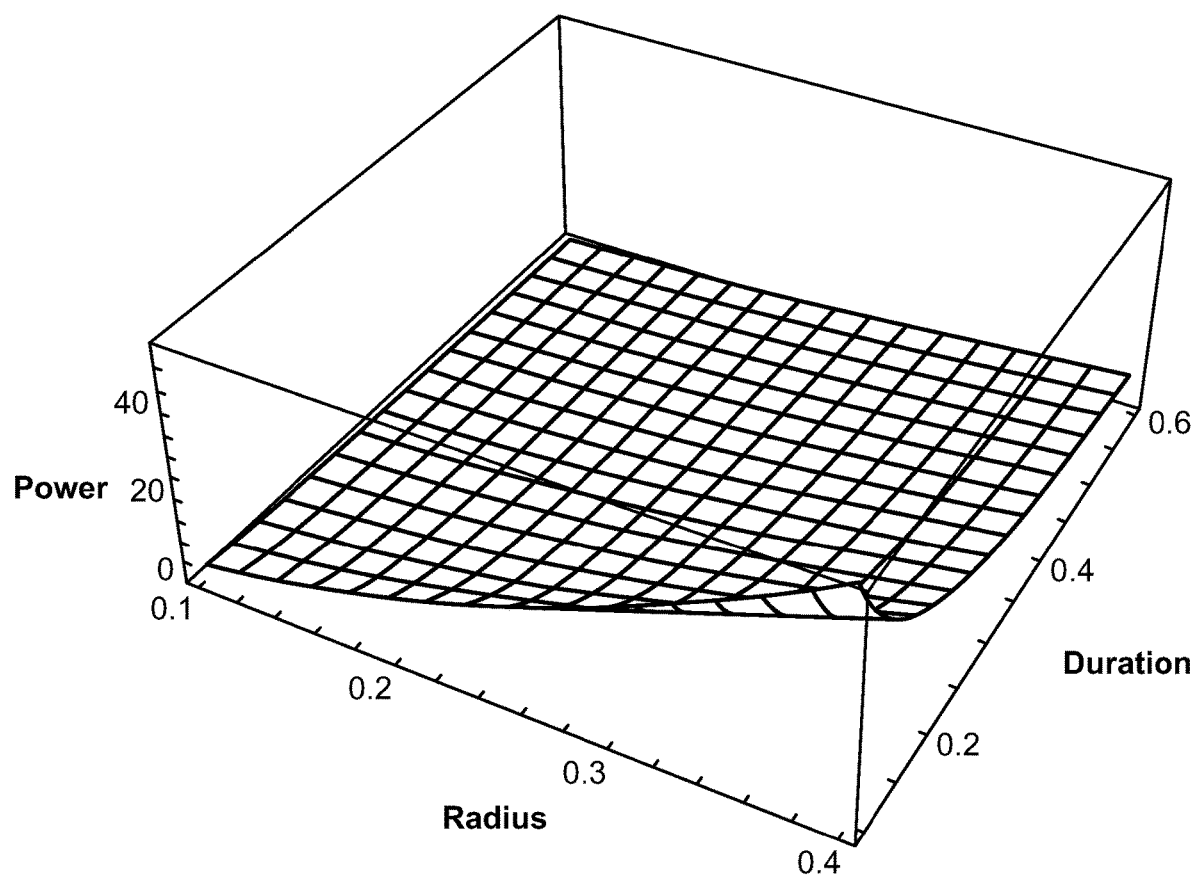
FIGS. 1A and 1B are graphs illustrating the average power of a laser source compared to a source radius and pulse train duration of the laser.

As shown in the accompanying drawings, and as more fully described herein, the present invention is directed to a system and method for delivering a pulsed energy, such as ultrasound, ultraviolet radiofrequency, microwave radiofrequency, one or more light beams, and the like, having energy parameters selected to cause a thermal time-course in tissue to raise the tissue temperature over a short period of time to a sufficient level to achieve a therapeutic effect while maintaining an average tissue temperature over a prolonged period of time below a predetermined level so as to avoid permanent tissue damage. It is believed that the creation of the thermal time-course stimulates heat shock protein activation or production and facilitates protein repair without causing any damage.

The inventors have discovered that electromagnetic radiation can be applied to retinal tissue in a manner that does not destroy or damage the retinal tissue while achieving beneficial effects on eye diseases. More particularly, a laser light beam can be generated that is therapeutic, yet sublethal to retinal tissue cells and thus avoids damaging photocoagulation in the retinal tissue which provides preventative and protective treatment of the retinal tissue of the eye. It is believed that this may be due, at least in part, to the stimulation and activation of heat shock proteins and the facilitation of protein repair in the retinal tissue. This is disclosed in U.S. patent application Ser. No. 14/607,959 filed Jan. 28, 2015, Ser. No. 13/798,523 filed Mar. 13, 2013, and Ser. No. 13/481,124 filed May 25, 2012, the contents of which are hereby incorporated by reference as if made in full.

Various parameters of the light beam must be taken into account and selected so that the combination of the selected parameters achieve the therapeutic effect while not permanently damaging the tissue. These parameters include laser wavelength, radius of the laser source or tissue application spot, laser power, total pulse train duration, and duty cycle of the pulse train.

The selection of these parameters may be determined by requiring that the Arrhenius integral for HSP activation be greater than 1 or unity. Arrhenius integrals are used for analyzing the impacts of actions on biological tissue. See, for instance, The CRC Handbook of Thermal Engineering, ed. Frank Kreith, Springer Science and Business Media (2000). At the same time, the selected parameters must not permanently damage the tissue. Thus, the Arrhenius integral for damage may also be used, wherein the solved Arrhenius integral is less than 1 or unity. Alternatively, the FDA/FCC constraints on energy deposition per unit gram of tissue and temperature rise as measured over periods of minutes be satisfied so as to avoid permanent tissue damage. The FDA/FCC requirements on energy deposition and temperature rise are widely used and can be referenced, for example, at www.fda.gov/medicaldevices/deviceregulationandguidance/guidancedocument s/ucm073817.htm#attacha for electromagnetic sources, and Anastosio and P. LaRivero, ed., Emerging Imaging Technologies. CRC Press (2012), for ultrasound sources. Generally speaking, tissue temperature rises of between 6° C. and 11° C. can create therapeutic effect, such as by activating heat shock proteins, whereas maintaining the average tissue temperature over a prolonged period of time, such as over several minutes, such as six minutes, below a predetermined temperature, such as 6° C. and even 1° C. or less in certain circumstances, will not permanently damage the tissue.

The inventors have discovered that generating a subthreshold, sublethal micropulse laser light beam which has a wavelength greater than 532 nm and a duty cycle of less than 10% at a predetermined intensity or power and a predetermined pulse length or exposure time creates desirable retinal photostimulation without any visible burn areas or tissue destruction. More particularly, a laser light beam having a wavelength of between 570 nm-1300 nm, and in a particularly preferred embodiment between 600 nm and 1100 nm, having a duty cycle of approximately 2.5%-10% and a predetermined average power or power intensity (such as between 100-590 watts per square centimeter at the retina or approximately 1 watt per laser spot for each treatment spot at the retina) and a predetermined pulse train length or exposure time (such as between 100 and 600 milliseconds or less) creates a sublethal, "true subthreshold" retinal photostimulation in which all areas of the retinal pigment epithelium exposed to the laser irradiation are preserved and available to contribute therapeutically. In other words, the inventors have found that raising the retinal tissue at least up to a therapeutic level but below a cellular or tissue lethal level recreates the benefit of the halo effect of the prior art methods without destroying, burning or otherwise damaging the retinal tissue. This is referred to herein as subthreshold diode micropulse laser treatment (SDM).

SDM does not produce laser-induced retinal damage (photocoagulation), and has no known adverse treatment effect, and has been reported to be an effective treatment in a number of retinal disorders (including diabetic macular edema (DME) proliferative diabetic retinopathy (PDR), macular edema due to branch retinal vein occlusion (BRVO), central serous chorioretinopathy (CSR), reversal of drug tolerance, and prophylactic treatment of progressive degenerative retinopathies such as dry age-related macular degeneration, Stargardts' disease, cone dystrophies, and retinitis pigmentosa. The safety of SDM is such that it may be used transfoveally in eyes with 20/20 visual acuity to reduce the risk of visual loss due to early fovea-involving DME.

A mechanism through which SDM might work is the generation or activation of heat shock proteins (HSPs). Despite a near infinite variety of possible cellular abnormalities, cells of all types share a common and highly conserved mechanism of repair: heat shock proteins (HSPs). HSPs are elicited almost immediately, in seconds to minutes, by almost any type of cell stress or injury. In the absence of lethal cell injury, HSPs are extremely effective at repairing and returning the viable cell toward a more normal functional state. Although HSPs are transient, generally peaking in hours and persisting for a few days, their effects may be long lasting. HSPs reduce inflammation, a common factor in many disorders.

Laser treatment can induce HSP production or activation and alter cytokine expression. The more sudden and severe the non-lethal cellular stress (such as laser irradiation), the more rapid and robust HSP activation. Thus, a burst of repetitive low temperature thermal spikes at a very steep rate of change (~7° C. elevation with each 100 µs micropulse, or 70,000° C./sec) produced by each SDM exposure is especially effective in stimulating activation of HSPs, particularly compared to non-lethal exposure to subthreshold treatment with continuous wave lasers, which can duplicate only the low average tissue temperature rise.

Laser wavelengths below 550 nm produce increasingly cytotoxic photochemical effects. The lower wavelength limit realistically usable by the process of the present invention is determined by the undesirable absorption by the visual pigments and other absorbers, including blood, the lens of the eye, etc. At approximately 570 nm, the sum of the optical densities of the long wavelength sensitive and medium wavelength sensitive visual pigments in the eye and the blood exceeds the optical density of the melanin. The absorption is dominated by melanin between 570 nm and 650 nm, where above 650 nm the absorption is practically all due to the melanin in the RPE. However, at higher wavelengths, such as above 1300 nm, there is a decrease in melanin absorption with increasing absorption by the water in the vitreous of the eye. At 1300 nm, for instance, the melanin absorbance is only 0.048 of what it is at 810 nm, and the radiation power due to this effect alone would have to be increased by a factor of 20 compared to the power at 810 nm to achieve the same temperature increase. Accordingly, the present invention can be performed at a broad range of wavelengths between 570 nm to 1300 nm, with the more preferable range of wavelengths being 600 nm to 1100 nm, and an even more preferable range of wavelengths of 650 nm to 900 nm, with the particularly preferred operating wavelength at approximately 810 nm. At these wavelengths, the melanin absorption is dominant and the heating primarily in the desired RPE and the wavelength is at a safe distance from the wavelengths where appreciable absorption occurs in the visual pigments as shorter wavelengths or water at longer wavelengths, which will create undesirable heating of the eye and other tissues. At 810 nm, SDM produces photothermal, rather than photochemical, cellular stress. Thus, SDM is able to affect the tissue without damaging it.

It has been found that the average required treatment power between tissue reset and tissue damage can be calculated with the wavelength used, the radiation train duration, preferably being between 0.03 and 0.8 seconds and a retinal application spot by the radiation being between 10 and 500 microns. A duty cycle of less than 10% and preferably between 2.5% and 5% with a total pulse duration of between 100 milliseconds and 600 milliseconds has been found to be effective. The corresponding peak powers, during the individual pulse, are obtained from the average powers by dividing by the duty cycle. The average power can vary between 0.0000069 to 37.5 watts within a wavelength between 570 nm-1300 nm, a pulse train duration between 30-800 milliseconds, and a treatment spot between 10-700 microns.

The clinical benefits of SDM are thus primarily produced by sub-morbid photothermal cellular HSP activation. In dysfunctional cells, HSP stimulation by SDM results in normalized cytokine expression, and consequently improved structure and function. The therapeutic effects of this "low-intensity" laser/tissue interaction are then amplified by "high-density" laser application, recruiting all the dysfunctional cells in the targeted tissue area by densely/confluently treating a large tissue area, including all areas of pathology, thereby maximizing the treatment effect. These principles define the treatment strategy of SDM described herein.

Because normally functioning cells are not in need of repair, HSP stimulation in normal cells would tend to have no notable clinical effect. The "patho-selectivity" of near infrared laser effects, such as SDM, affecting sick cells but not affecting normal ones, on various cell types is consistent with clinical observations of SDM. SDM has been reported to have a clinically broad therapeutic range, unique among retinal laser modalities, consistent with American National Standards Institute "Maximum Permissible Exposure" predictions. While SDM may cause direct photothermal effects such as entropic protein unfolding and disaggregation, SDM appears optimized for clinically safe and effective stimulation of HSP-mediated repair.

As noted above, while SDM stimulation of HSPs is non-specific with regard to the disease process, the result of HSP mediated repair is by its nature specific to the state of the dysfunction. HSPs tend to fix what is wrong, whatever that might be. Thus, the observed effectiveness of SDM in retinal conditions as widely disparate as BRVO, DME, PDR, CSR, age-related and genetic retinopathies, and drug-tolerant NAMD. Conceptually, this facility can be considered a sort of "Reset to Default" mode of SDM action. For the wide range of disorders in which cellular function is critical, SDM normalizes cellular function by triggering a "reset" (to the "factory default settings") via HSP-mediated cellular repair.

The inventors have found that SDM treatment of patients suffering from age-related macular degeneration (AMD) can slow the progress or even stop the progression of AMD. Most of the patients have seen significant improvement in dynamic functional logMAR mesoptic visual acuity and mesoptic contrast visual acuity after the SDM treatment. It is believed that SDM works by targeting, preserving, and "normalizing" (moving toward normal) function of the retinal pigment epithelium (RPE).

SDM has also been shown to stop or reverse the manifestations of the diabetic retinopathy disease state without treatment-associated damage or adverse effects, despite the persistence of systemic diabetes mellitus. On this basis it is hypothesized that SDM might work by inducing a return to more normal cell function and cytokine expression in diabetes-affected RPE cells, analogous to hitting the "reset" button of an electronic device to restore the factory default settings. Based on the above information and studies, SDM treatment may directly affect cytokine expression via heat shock protein (HSP) activation in the targeted tissue.

As heat shock proteins play a role in responding to a large number of abnormal conditions in body tissue other than eye tissue, it is believed that similar systems and methodologies can be advantageously used in treating such abnormal conditions, infections, etc. As such, the present invention is directed to the controlled application of ultrasound or electromagnetic radiation to treat abnormal conditions including inflammations, autoimmune conditions, and cancers that are accessible by means of fiber optics of endoscopes or surface probes as well as focused electromagnetic/sound waves. For example, cancers on the surface of the prostate that have the largest threat of metastasizing can be accessed by means of fiber optics in a proctoscope. Colon tumors can be accessed by an optical fiber system, like those used in colonoscopy.

As indicated above, subthreshold diode micropulse laser (SDM) photostimulation has been effective in stimulating direct repair of slightly misfolded proteins in eye tissue.

Besides HSP activation, another way this may occur is because the spikes in temperature caused by the micropulses in the form of a thermal time-course allows diffusion of water inside proteins, and this allows breakage of the peptide-peptide hydrogen bonds that prevent the protein from returning to its native state. The diffusion of water into proteins results in an increase in the number of restraining hydrogen bonds by a factor on the order of a thousand. Thus, it is believed that this process could be applied to other tissues and diseases advantageously as well.

As explained above, the energy source to be applied to the target tissue will have energy and operating parameters which must be determined and selected so as to achieve the therapeutic effect while not permanently damaging the tissue. Using a light beam energy source, such as a laser light beam, as an example, the laser wavelength, duty cycle and total pulse train duration parameters must be taken into account. Other parameters which can be considered include the radius of the laser source as well as the average laser power. Adjusting or selecting one of these parameters can have an effect on at least one other parameter.

Figure 1B:
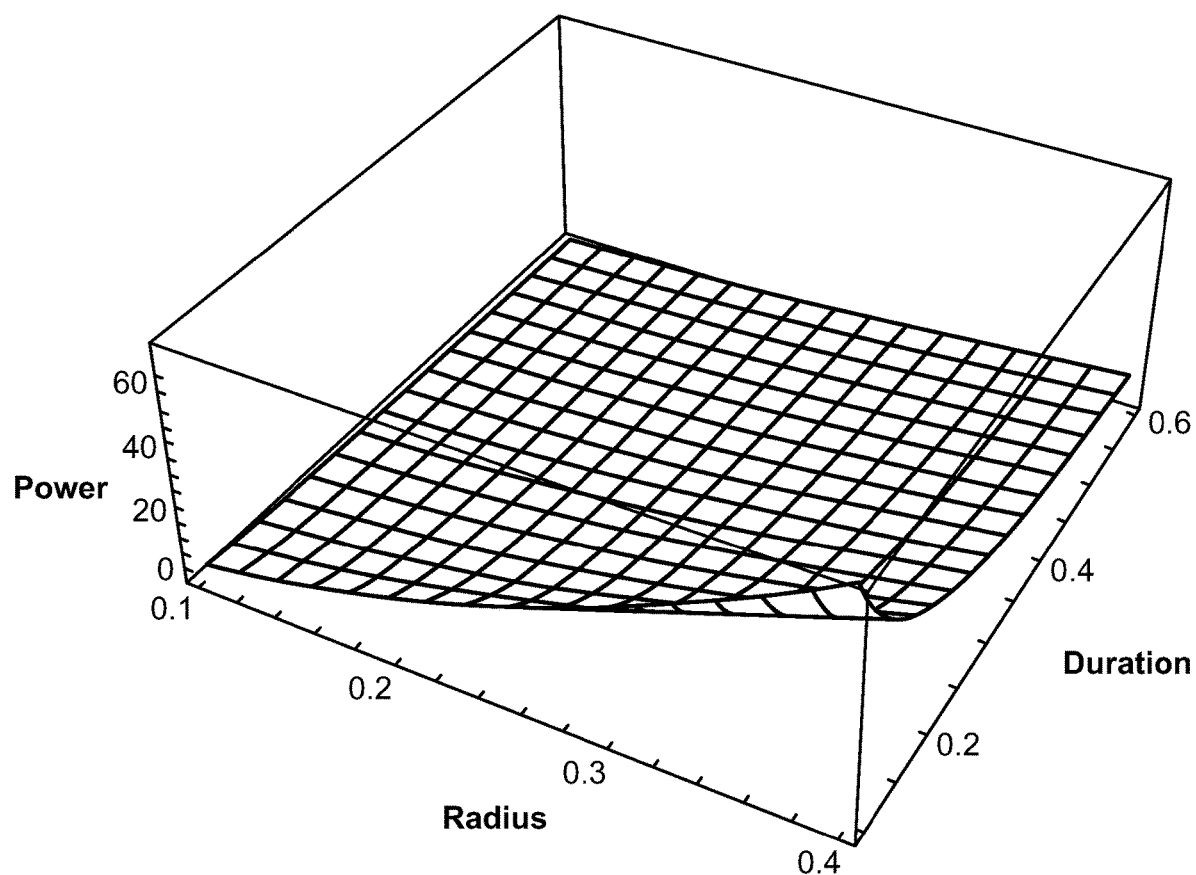

FIGS. 1A and 1B illustrate graphs showing the average power in watts as compared to the laser source radius (between 0.1 cm and 0.4 cm) and pulse train duration (between 0.1 and 0.6 seconds). FIG. 1A shows a wavelength of 880 nm, whereas FIG. 1B has a wavelength of 1000 nm. It can be seen in these figures that the required power decreases monotonically as the radius of the source decreases, as the total train duration increases, and as the wavelength decreases. The preferred parameters for the radius of the laser source is 1 mm-4 mm. For a wavelength of 880 nm, the minimum value of power is 0.55 watts, with a radius of the laser source being 1 mm, and the total pulse train duration being 600 milliseconds. The maximum value of power for the 880 nm wavelength is 52.6 watts when the laser source radius is 4 mm and the total pulse drain duration is 100 milliseconds. However, when selecting a laser having a wavelength of 1000 nm, the minimum power value is 0.77 watts with a laser source radius of 1 mm and a total pulse train duration of 600 milliseconds, and a maximum power value of 73.6 watts when the laser source radius is 4 mm and the total pulse duration is 100 milliseconds. The corresponding peak powers, during an individual pulse, are obtained from the average powers by dividing by the duty cycle.

The volume of the tissue region to be heated is determined by the wavelength, the absorption length in the relevant tissue, and by the beam width. The total pulse duration and the average laser power determine the total energy delivered to heat up the tissue, and the duty cycle of the pulse train gives the associated spike, or peak, power associated with the average laser power. Preferably, the pulsed energy source energy parameters are selected so that approximately 20 to 40 joules of energy is absorbed by each cubic centimeter of the target tissue.

The absorption length is very small in the thin melanin layer in the retinal pigmented epithelium. In other parts of the body, the absorption length is not generally that small. In wavelengths ranging from 400 nm to 2000 nm, the penetration depth and skin is in the range of 0.5 mm to 3.5 mm. The penetration depth into human mucous tissues is in the range of 0.5 mm to 6.8 mm. Accordingly, the heated volume will be limited to the exterior or interior surface where the radiation source is placed, with a depth equal to the penetration depth, and a transverse dimension equal to the transverse dimension of the radiation source. Since the light beam energy source is used to treat diseased tissues near external surfaces or near internal accessible surfaces, a source radii of between 1 mm to 4 mm and operating a wavelength of 880 nm yields a penetration depth of approximately 2.5 mm and a wavelength of 1000 nm yields a penetration depth of approximately 3.5 mm.

Figure 2A:
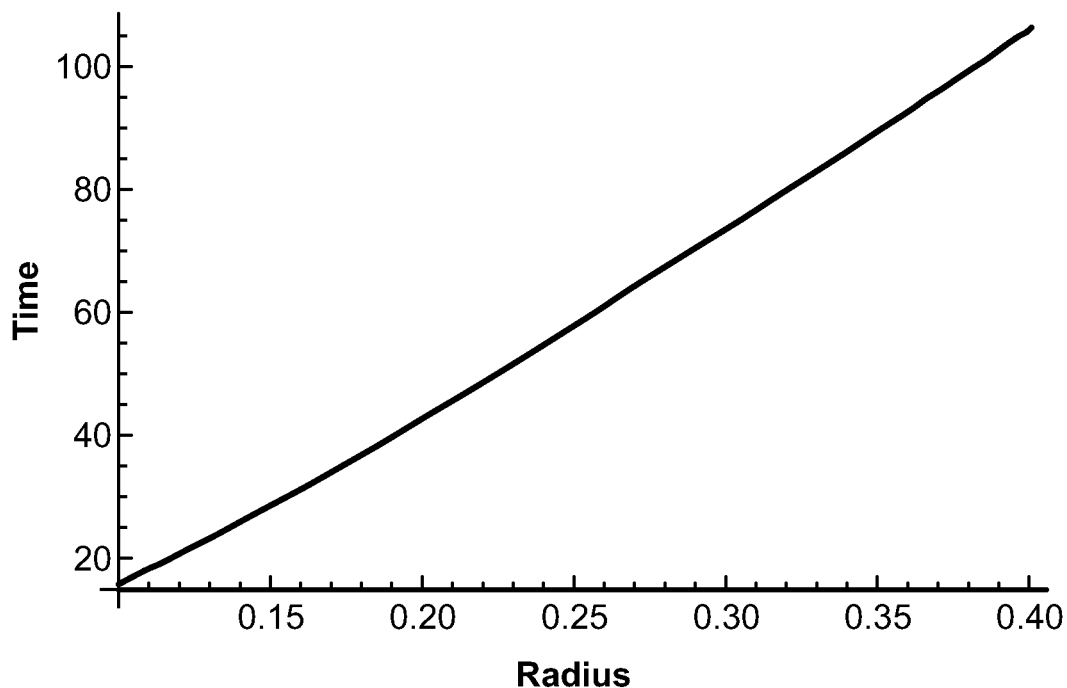
FIGS. 2A and 2B are graphs illustrating the time for the temperature to decay depending upon the laser source radius and wavelength.
Figure 2B:
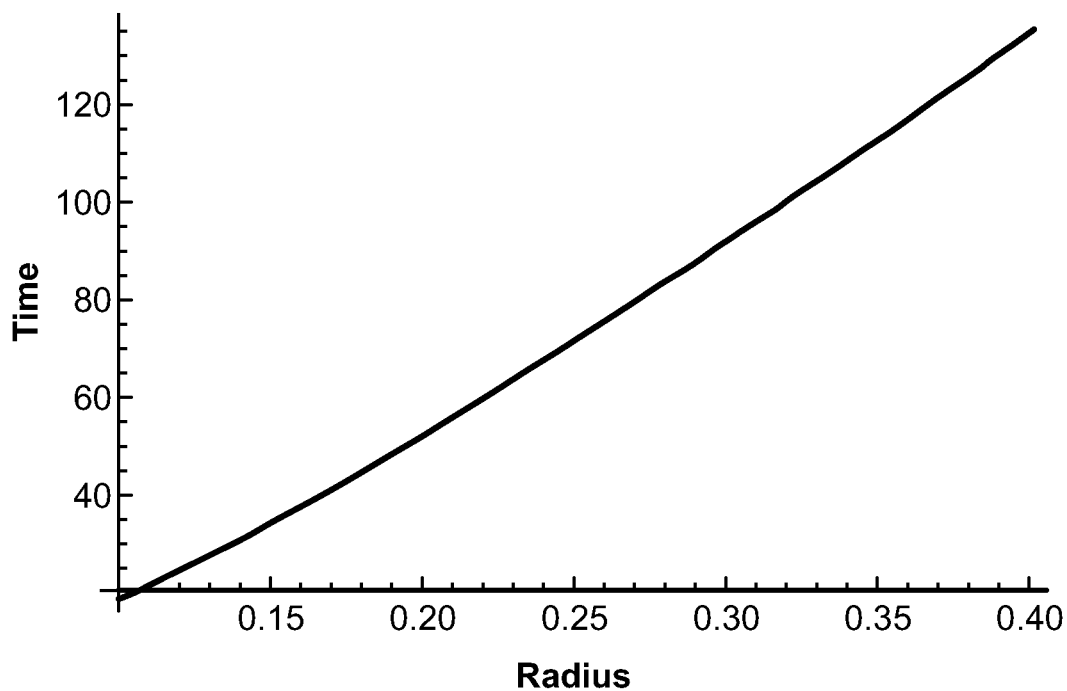

It has been determined that the target tissue can be heated to up to approximately 11° C. for a short period of time, such as less than one second, to create the therapeutic effect of the invention while maintaining the target tissue average temperature to a lower temperature range, such as less than 6° C. or even 1° C. or less over a prolonged period of time, such as several minutes. The selection of the duty cycle and the total pulse train duration provide time intervals in which the heat can dissipate. A duty cycle of less than 10%, and preferably between 2.5% and 5%, with a total pulse duration of between 100 milliseconds and 600 milliseconds has been found to be effective. FIGS. 2A and 2B illustrate the time to decay from 10° C. to 1° C. for a laser source having a radius of between 0.1 cm and 0.4 cm with the wavelength being 880 nm in FIG. 2A and 1000 nm in FIG. 2B. It can be seen that the time to decay is less when using a wavelength of 880 nm, but either wavelength falls within the acceptable requirements and operating parameters to achieve the benefits of the present invention while not causing permanent tissue damage.

It has been found that the average temperature rise of the desired target region increasing at least 6° C. and up to 11° C., and preferably approximately 10° C., during the total irradiation period results in HSP activation. The control of the target tissue temperature is determined by choosing source and target parameters such that the Arrhenius integral for HSP activation is larger than 1, while at the same time assuring compliance with the conservative FDA/FCC requirements for avoiding damage or a damage Arrhenius integral being less than 1.

In order to meet the conservative FDA/FCC constraints to avoid permanent tissue damage, for light beams and other electromagnetic radiation sources, the average temperature rise of the target tissue over any six-minute period is 1° C. or less. FIGS. 2A and 2B above illustrate the typical decay times required for the temperature in the heated target region to decrease by thermal diffusion from a temperature rise of approximately 10° C. to 1° C. as can be seen in FIG. 2A when the wavelength is 880 nm and the source diameter is 1 millimeter, the temperature decay time is 16 seconds. The temperature decay time is 107 seconds when the source diameter is 4 mm. As shown in FIG. 2B, when the wavelength is 1000 nm, the temperature decay time is 18 seconds when the source diameter is 1 mm and 136 seconds when the source diameter is 4 mm. This is well within the time of the average temperature rise being maintained over the course of several minutes, such as 6 minutes or less. While the target tissue's temperature is raised, such as to approximately 10° C., very quickly, such as in a fraction of a second during the application of the energy source to the tissue, the relatively low duty cycle provides relatively long periods of time between the pulses of energy applied to the tissue and the relatively short pulse train duration ensure sufficient temperature diffusion and decay within a relatively short period of time comprising several minutes, such as 6 minutes or less, that there is no permanent tissue damage.

The parameters differ for the individual energy sources, including microwave, infrared lasers, radiofrequency and ultrasound, because the absorption properties of tissues differ for these different types of energy sources. The tissue water content can vary from one tissue type to another, however, there is an observed uniformity of the properties of tissues at normal or near normal conditions which has allowed publication of tissue parameters that are widely used by clinicians in designing treatments. Below are tables illustrating the properties of electromagnetic waves in biological media, with Table 1 relating to muscle, skin and tissues with high water content, and Table 2 relating to fat, bone and tissues with low water content.

the first and second kind. The heating occurs only in a region that is comparable in size to the dimensions of the coil source itself. Accordingly, if it is desired to preferentially heat a region characterized by a radius, the source coil will be chosen to have a similar radius. The heating drops off very rapidly outside of a hemispherical region of radius

TABLE 1

Properties of Electromagnetic Waves in Biological Media: Muscle, Skin, and Tissues with High Water Content

| Frequency (MHz) | Wavelength in Air (cm) | Dielectric Constant $\epsilon_H$ | Conductivity $\sigma_H$ (mho/m) | Wavelength $\lambda_H$ (cm) | Depth of Penetration (cm) | Reflection Coefficient Air-Muscle Interface r | ø | Reflection Coefficient Muscle-Fat Interface r | ø |
|---|---|---|---|---|---|---|---|---|---|
| 1 | 30000 | 2000 | 0.400 | 436 | 91.3 | 0.982 | +179 | | |
| 10 | 3000 | 160 | 0.625 | 118 | 21.6 | 0.956 | +178 | | |
| 27.12 | 1106 | 113 | 0.612 | 68.1 | 14.3 | 0.925 | +177 | 0.651 | −11.13 |
| 40.68 | 738 | 97.3 | 0.693 | 51.3 | 11.2 | 0.913 | +176 | 0.652 | −10.21 |
| 100 | 300 | 71.7 | 0.889 | 27 | 6.66 | 0.881 | +175 | 0.650 | −7.96 |
| 200 | 150 | 56.5 | 1.28 | 16.6 | 4.79 | 0.844 | +175 | 0.612 | −8.06 |
| 300 | 100 | 54 | 1.37 | 11.9 | 3.89 | 0.825 | +175 | 0.592 | −8.14 |
| 433 | 69.3 | 53 | 1.43 | 8.76 | 3.57 | 0.803 | +175 | 0.562 | −7.06 |
| 750 | 40 | 52 | 1.54 | 5.34 | 3.18 | 0.779 | +176 | 0.532 | −5.69 |
| 915 | 32.8 | 51 | 1.60 | 4.46 | 3.04 | 0.772 | +177 | 0.519 | −4.32 |
| 1500 | 20 | 49 | 1.77 | 2.81 | 2.42 | 0.761 | +177 | 0.506 | −3.66 |
| 2450 | 12.2 | 47 | 2.21 | 1.76 | 1.70 | 0.754 | +177 | 0.500 | −3.88 |
| 3000 | 10 | 46 | 2.26 | 1.45 | 1.61 | 0.751 | +178 | 0.495 | −3.20 |
| 5000 | 6 | 44 | 3.92 | 0.89 | 0.788 | 0.749 | +177 | 0.502 | −4.95 |
| 5800 | 5.17 | 43.3 | 4.73 | 0.775 | 0.720 | 0.746 | +177 | 0.502 | −4.29 |
| 8000 | 3.75 | 40 | 7.65 | 0.578 | 0.413 | 0.744 | +176 | 0.513 | −6.65 |
| 10000 | 3 | 39.9 | 10.3 | 0.464 | 0.343 | 0.743 | +176 | 0.518 | −5.95 |

TABLE 2

Properties of Electromagnetic Waves in Biological Media: Fat, Bone, and Tissues with Low Water Content

| Frequency (MHz) | Wavelength in Air (cm) | Dielectric Constant $\epsilon_L$ | Conductivity $\sigma_L$ (mmho/m) | Wavelength $\lambda_L$ (cm) | Depth of Penetration (cm) | Reflection Coefficient Air-Fat Interface r | ø | Reflection Coefficient Fat-Muscle Interface r | ø |
|---|---|---|---|---|---|---|---|---|---|
| 1 | 30000 | | | | | | | | |
| 10 | 3000 | | | | | | | | |
| 27.12 | 1106 | 20 | 10.9-43.2 | 241 | 159 | 0.660 | +174 | 0.651 | +169 |
| 40.68 | 738 | 14.6 | 12.6-52.8 | 187 | 118 | 0.617 | +173 | 0.652 | +170 |
| 100 | 300 | 7.45 | 19.1-75.9 | 106 | 60.4 | 0.511 | +168 | 0.650 | +172 |
| 200 | 150 | 5.95 | 25.8-94.2 | 59.7 | 39.2 | 0.458 | +168 | 0.612 | +172 |
| 300 | 100 | 5.7 | 31.6-107 | 41 | 32.1 | 0.438 | +169 | 0.592 | +172 |
| 433 | 69.3 | 5.6 | 37.9-118 | 28.8 | 26.2 | 0.427 | +170 | 0.562 | +173 |
| 750 | 40 | 5.6 | 49.8-138 | 16.8 | 23 | 0.415 | +173 | 0.532 | +174 |
| 915 | 32.8 | 5.6 | 55.6-147 | 13.7 | 17.7 | 0.417 | +173 | 0.519 | +176 |
| 1500 | 20 | 5.6 | 70.8-171 | 8.41 | 13.9 | 0.412 | +174 | 0.506 | +176 |
| 2450 | 12.2 | 5.5 | 96.4-213 | 5.21 | 11.2 | 0.406 | +176 | 0.500 | +176 |
| 3000 | 10 | 5.5 | 110-234 | 4.25 | 9.74 | 0.406 | +176 | 0.495 | +177 |
| 5000 | 6 | 5.5 | 162-309 | 2.63 | 6.67 | 0.393 | +176 | 0.502 | +175 |
| 5900 | 5.17 | 5.05 | 186-338 | 2.29 | 5.24 | 0.388 | +176 | 0.502 | +176 |
| 8000 | 3.75 | 4.7 | 255-431 | 1.73 | 4.61 | 0.371 | +176 | 0.513 | +173 − |
| 10000 | 3 | 4.5 | 324-549 | 1.41 | 3.39 | 0.363 | +175 | 0.518 | +174, − |

The absorption lengths of radiofrequency in body tissue are long compared to body dimensions. Consequently, the heated region is determined by the dimensions of the coil that is the source of the radiofrequency energy rather than by absorption lengths. Long distances r from a coil the magnetic (near) field from a coil drops off as $1/r^3$. At smaller distances, the electric and magnetic fields can be expressed in terms of the vector magnetic potential, which in turn can be expressed in closed form in terms of elliptic integrals of the first and second kind. because of the $1/r^3$ drop off of the magnetic field. Since it is proposed to use the radiofrequency the diseased tissue accessible only externally or from inner cavities, it is reasonable to consider a coil radii of between approximately 2 to 6 mm.

The radius of the source coil(s) as well as the number of ampere turns (NI) in the source coils give the magnitude and spatial extent of the magnetic field, and the radiofrequency is a factor that relates the magnitude of the electric field to the magnitude of the magnetic field. The heating is proportional to the product of the conductivity and the square of the electric field. For target tissues of interest that are near external or internal surfaces, the conductivity is that of skin and mucous tissue. The duty cycle of the pulse train as well as the total train duration of a pulse train are factors which affect how much total energy is delivered to the tissue.

Figure 3:
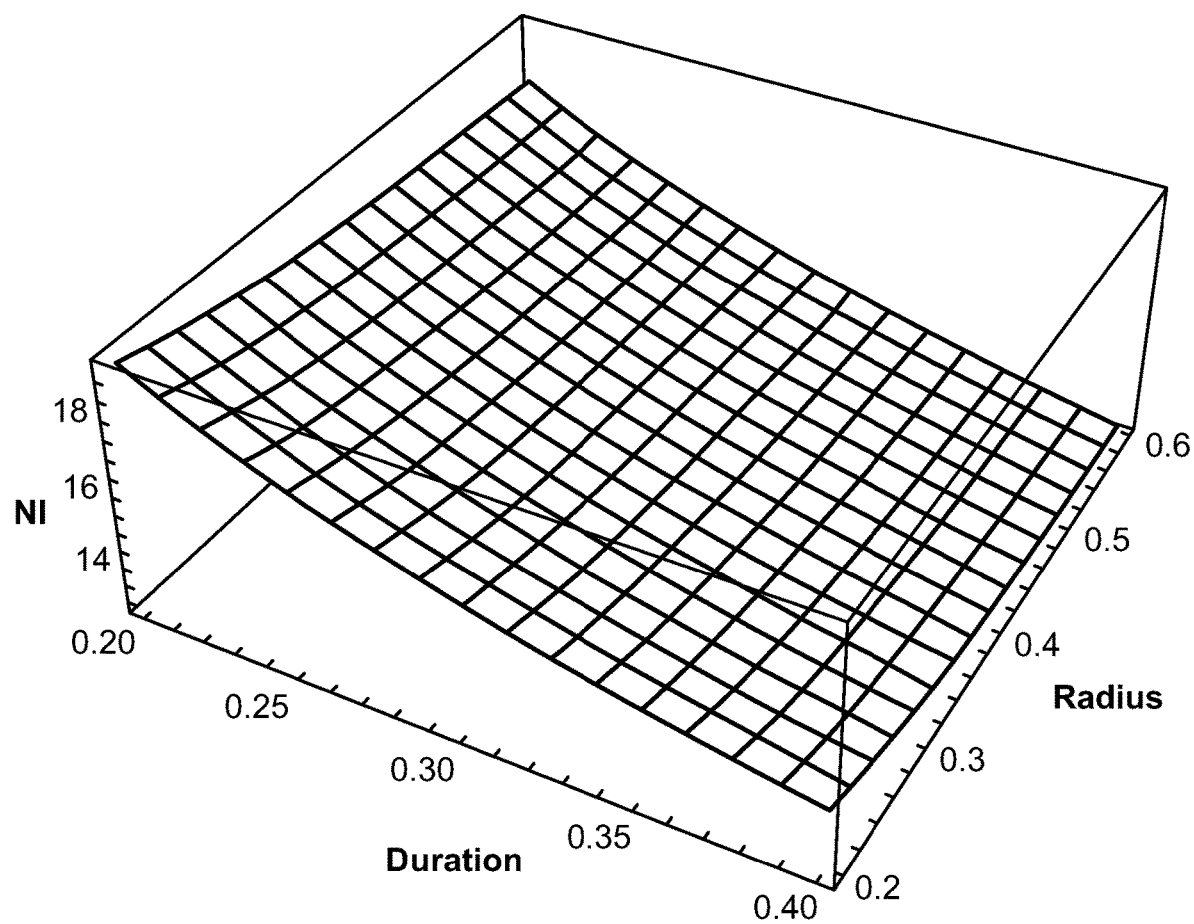
FIGS. 3-6 are graphs illustrating the peak ampere turns for various radiofrequencies, duty cycles, and coil radii.
Figure 4:
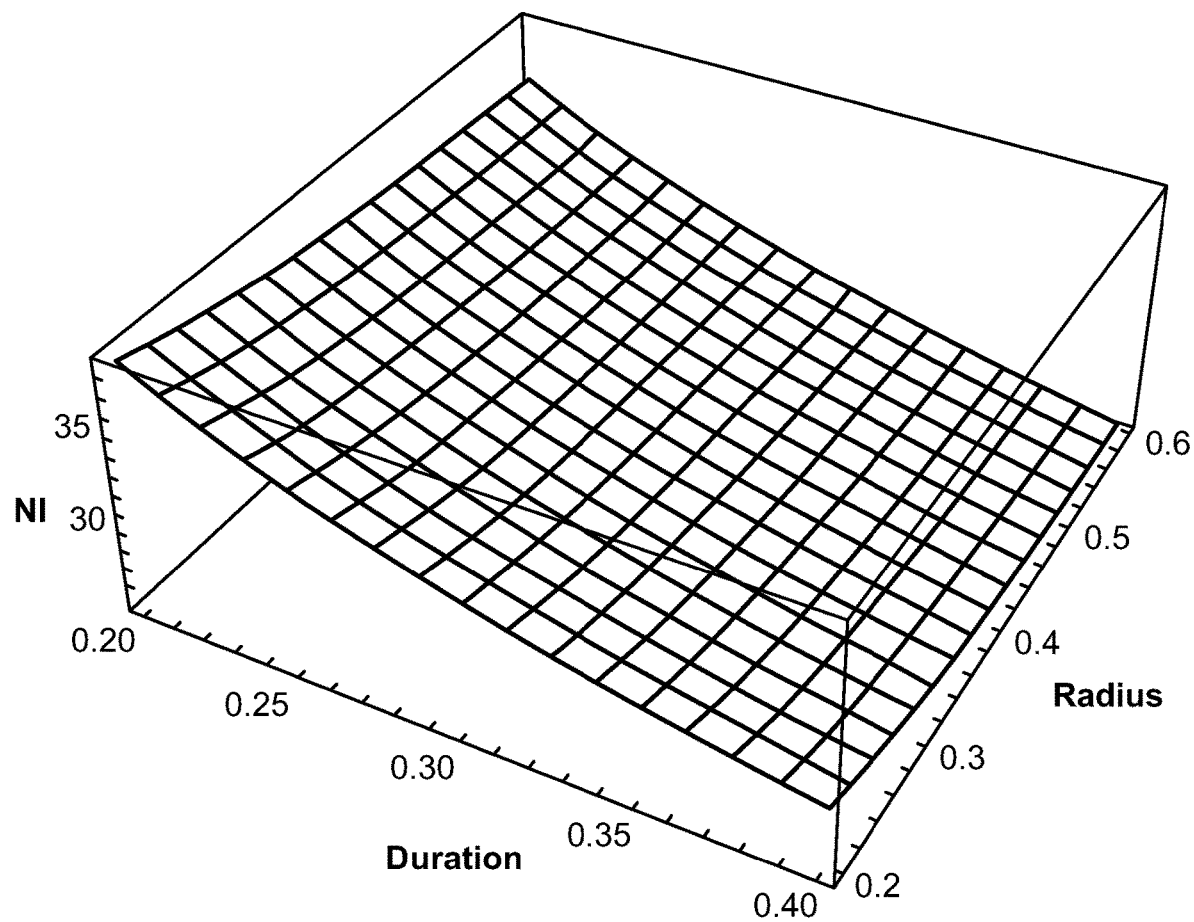
Figure 5:
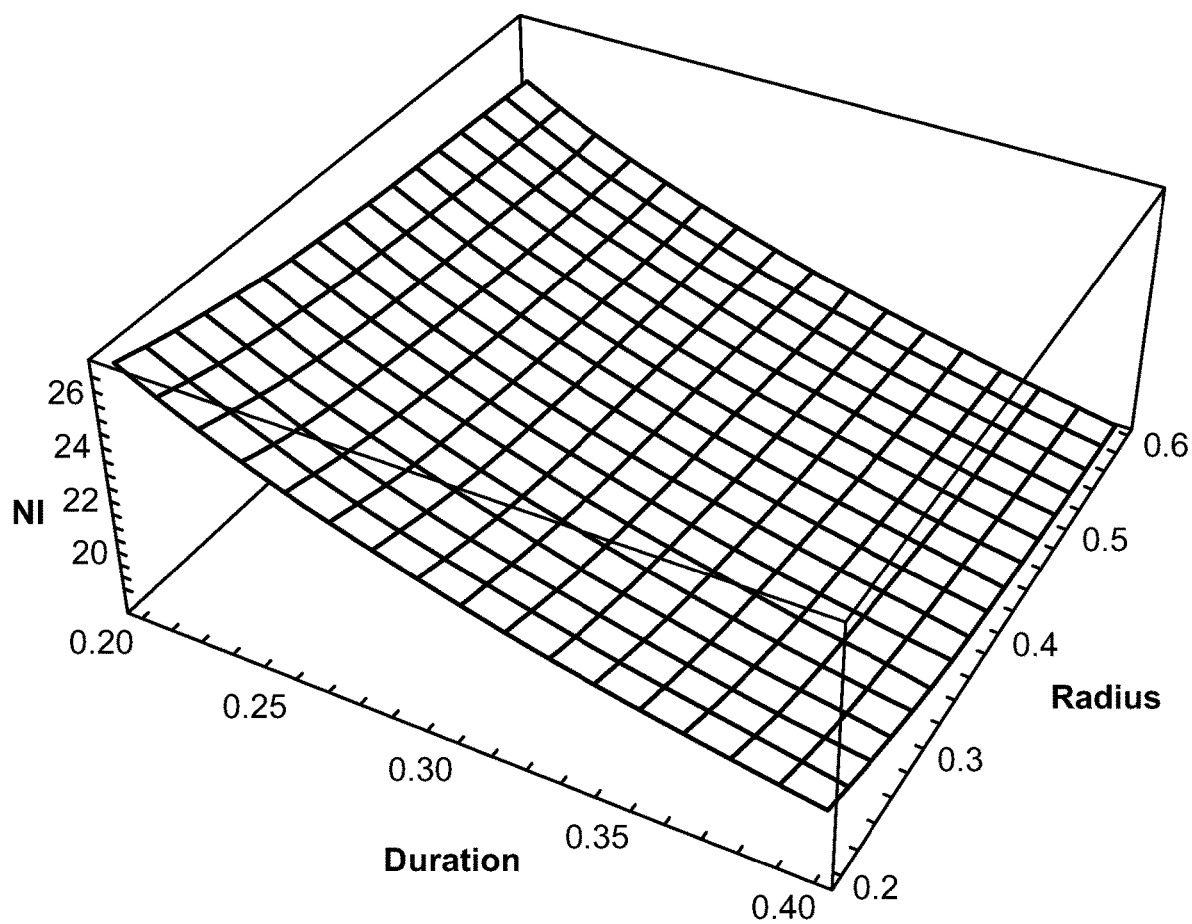
Figure 6:
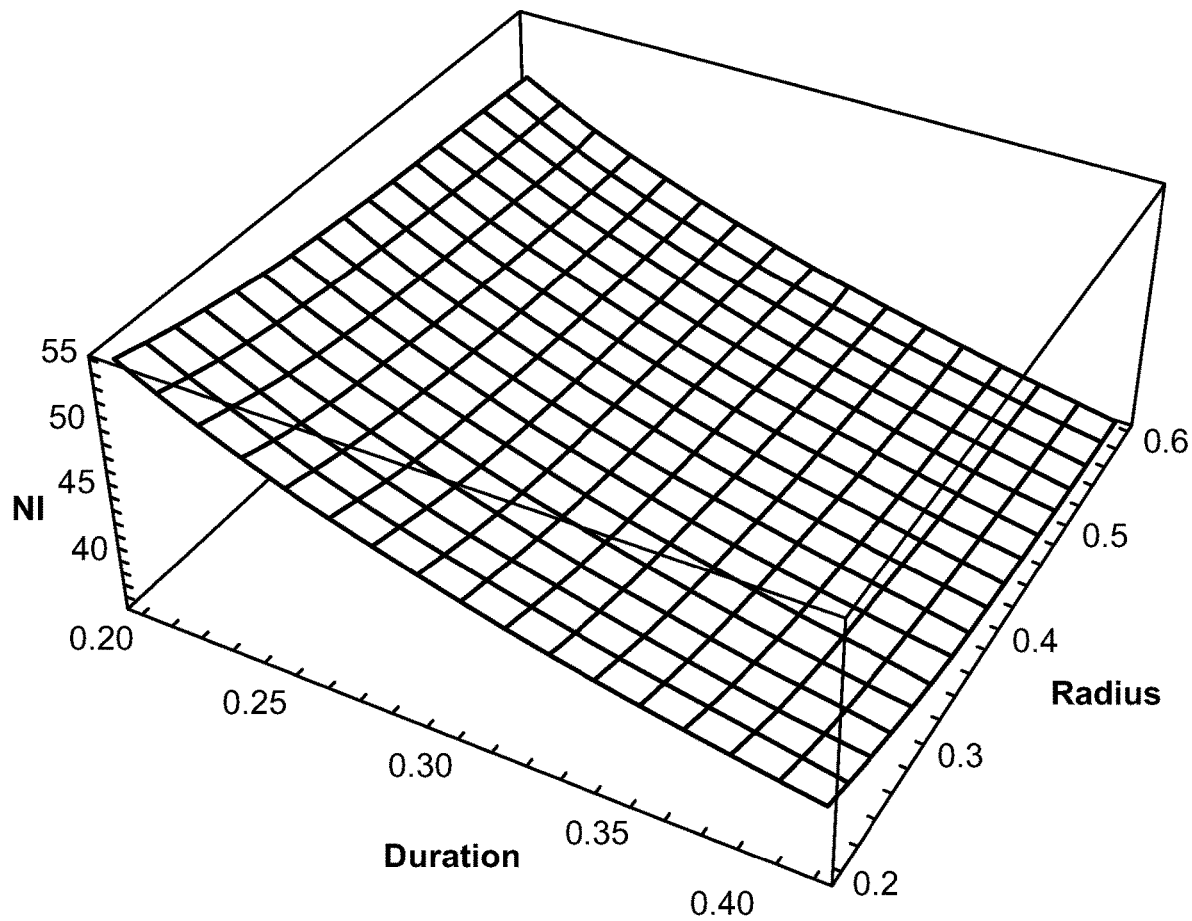

Preferred parameters for a radiofrequency energy source have been determined to be a coil radii between 2 and 6 mm, radiofrequencies in the range of 3-6 MHz, total pulse train durations of 0.2 to 0.4 seconds, and a duty cycle of between 2.5% and 5%. FIGS. 3-6 show how the number of ampere turns varies as these parameters are varied in order to give a temperature rise that produces an Arrhenius integral of approximately one or unity for HSP activation. With reference to FIG. 3, for an RF frequency of 6 MHz, a pulse train duration of between 0.2 and 0.4 seconds, a coil radius between 0.2 and 0.6 cm, and a duty cycle of 5%, the peak ampere turns (NI) is 13 at the 0.6 cm coil radius and 20 at the 0.2 cm coil radius. For a 3 MHz frequency, as illustrated in FIG. 4, the peak ampere turns is 26 when the pulse train duration is 0.4 seconds and the coil radius is 0.6 cm and the duty cycle is 5%. However, with the same 5% duty cycle, the peak ampere turns is 40 when the coil radius is 0.2 cm and the pulse train duration is 0.2 seconds. A duty cycle of 2.5% is used in FIGS. 5 and 6. This yields, as illustrated in FIG. 5, 18 amp turns for a 6 MHz radiofrequency having a coil radius of 0.6 cm and a pulse train duration of 0.4 seconds, and 29 amp turns when the coil radius is only 0.2 cm and the pulse train duration is 0.2 seconds. With reference to FIG. 6, with a duty cycle of 2.5% and a radiofrequency of 3 MHz, the peak ampere turns is 36 when the pulse train duration is 0.4 seconds and the coil radius is 0.6 cm, and 57 amp turns when the pulse train duration is 0.2 seconds and the coil radius is 0.2 cm.

Figure 7:
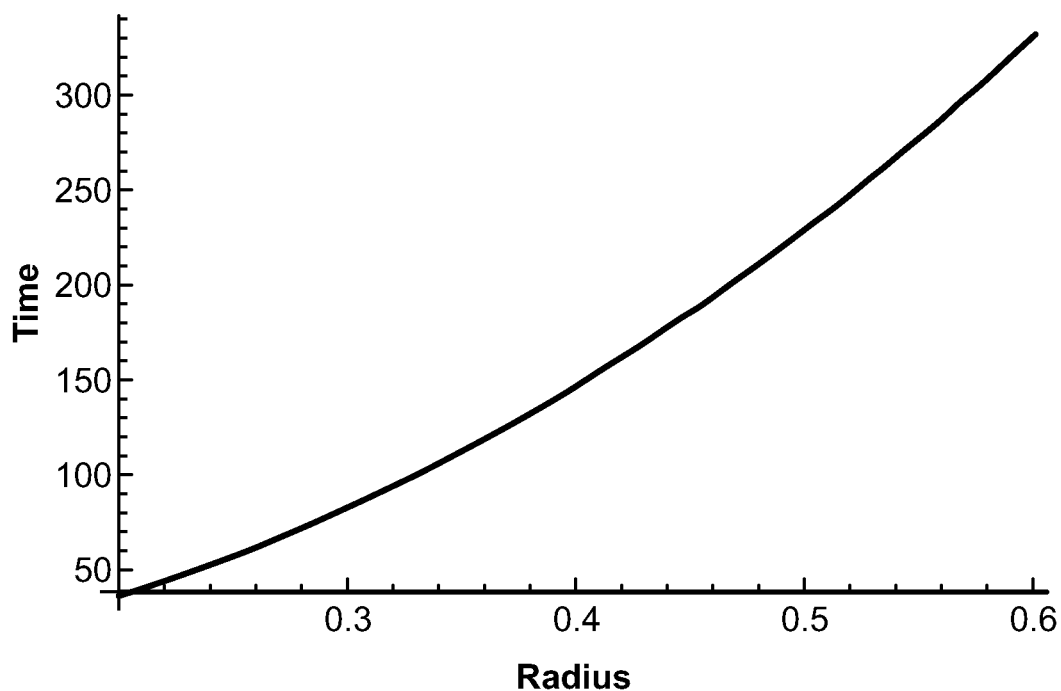
FIG. 7 is a graph depicting the time for temperature rise to decay compared to radiofrequency coil radius.

The time, in seconds, for the temperature rise to decay from approximately 10° C. to approximately 1° C. for coil radii between 0.2 cm and 0.6 cm is illustrated for a radiofrequency energy source in FIG. 7. The temperature decay time is approximately 37 seconds when the radiofrequency coil radius is 0.2 cm, and approximately 233 seconds when the radiofrequency coil radius is 0.5 cm. When the radiofrequency coil radius is 0.6 cm, the decay time is approximately 336 seconds, which is still within the acceptable range of decay time, but at an upper range thereof.

Microwaves are another electromagnetic energy source which can be utilized in accordance with the present invention. The frequency of the microwave determines the tissue penetration distance. The gain of a conical microwave horn is large compared to the microwave wavelength, indicating under those circumstances that the energy is radiated mostly in a narrow forward load. Typically, a microwave source used in accordance with the present invention has a linear dimension on the order of a centimeter or less, thus the source is smaller than the wavelength, in which case the microwave source can be approximated as a dipole antenna. Such small microwave sources are easier to insert into internal body cavities and can also be used to radiate external surfaces. In that case, the heated region can be approximated by a hemisphere with a radius equal to the absorption length of the microwave in the body tissue being treated. As the microwaves are used to treat tissue near external surfaces or surfaces accessible from internal cavities, frequencies in the 10-20 GHz range are used, wherein the corresponding penetration distances are only between approximately 2 and 4 mm.

The temperature rise of the tissue using a microwave energy source is determined by the average power of the microwave and the total pulse train duration. The duty cycle of the pulse train determines the peak power in a single pulse in a train of pulses. As the radius of the source is taken to be less than approximately 1 centimeter, and frequencies between 10 and 20 GHz are typically used, a resulting pulse train duration of 0.2 and 0.6 seconds is preferred.

The required power decreases monotonically as the train duration increases and as the microwave frequency increases. For a frequency of 10 GHz, the average power is 18 watts when the pulse train duration is 0.6 seconds, and 52 watts when the pulse train duration is 0.2 seconds. For a 20 GHz microwave frequency, an average power of 8 watts is used when the pulse train is 0.6 seconds, and can be 26 watts when the pulse train duration is only 0.2 seconds. The corresponding peak power are obtained from the average power simply by dividing by the duty cycle.

Figure 8:
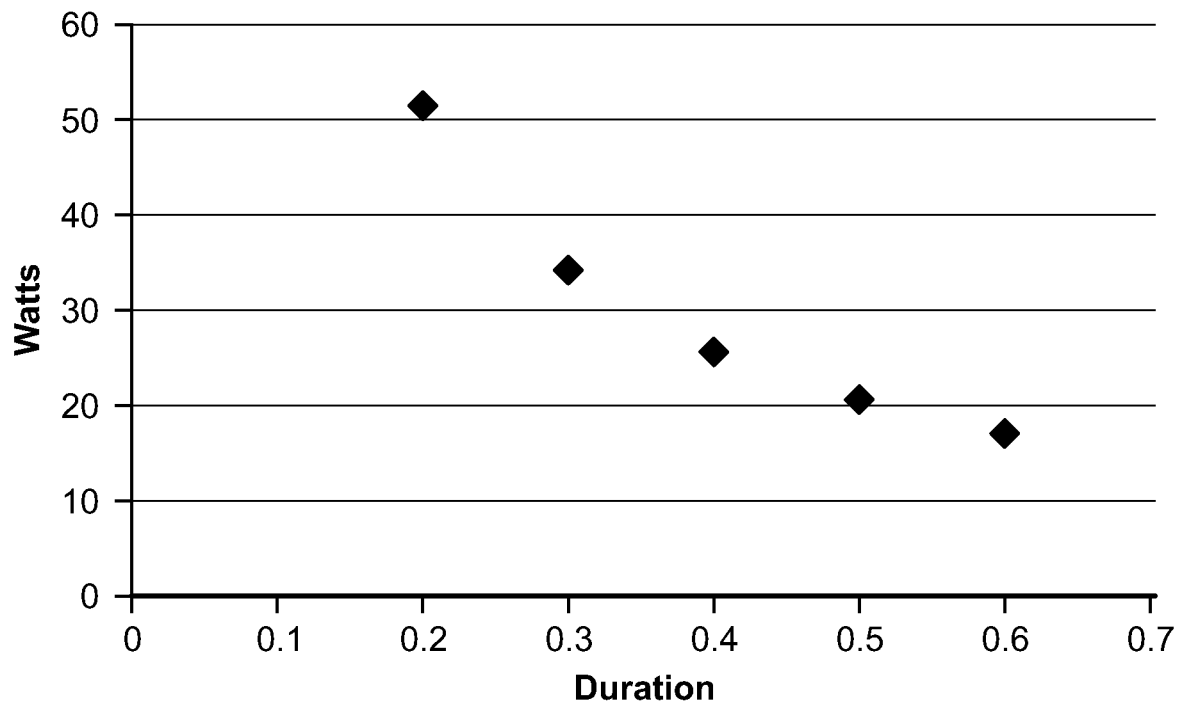
FIGS. 8 and 9 are graphs depicting the average microwave power compared to microwave frequency and pulse train durations.
Figure 9:
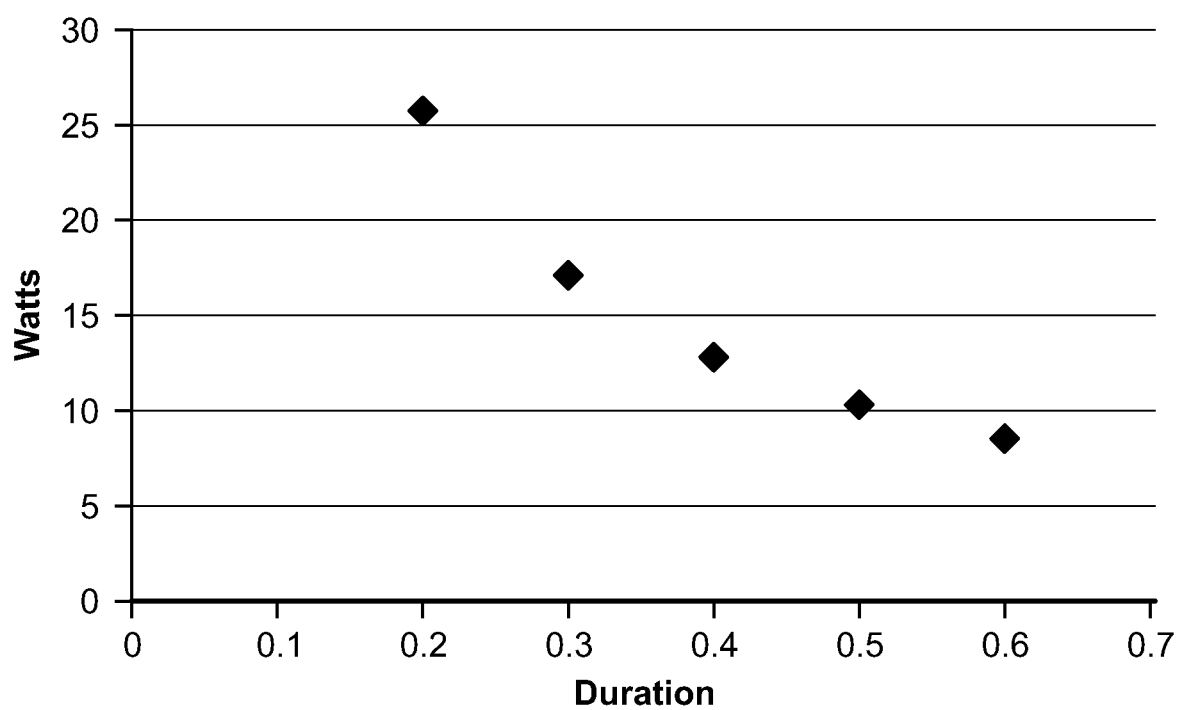

With reference now to FIG. 8, a graph depicts the average microwave power in watts of a microwave having a frequency of 10 GHz and a pulse train duration from between 0.2 seconds and 0.6 seconds. FIG. 9 is a similar graph, but showing the average microwave power for a microwave having a frequency of 20 GHz. Thus, it will be seen that the average microwave source power varies as the total train duration and microwave frequency vary. The governing condition, however, is that the Arrhenius integral for HSP activation in the heated region is approximately 1.

Figure 10:
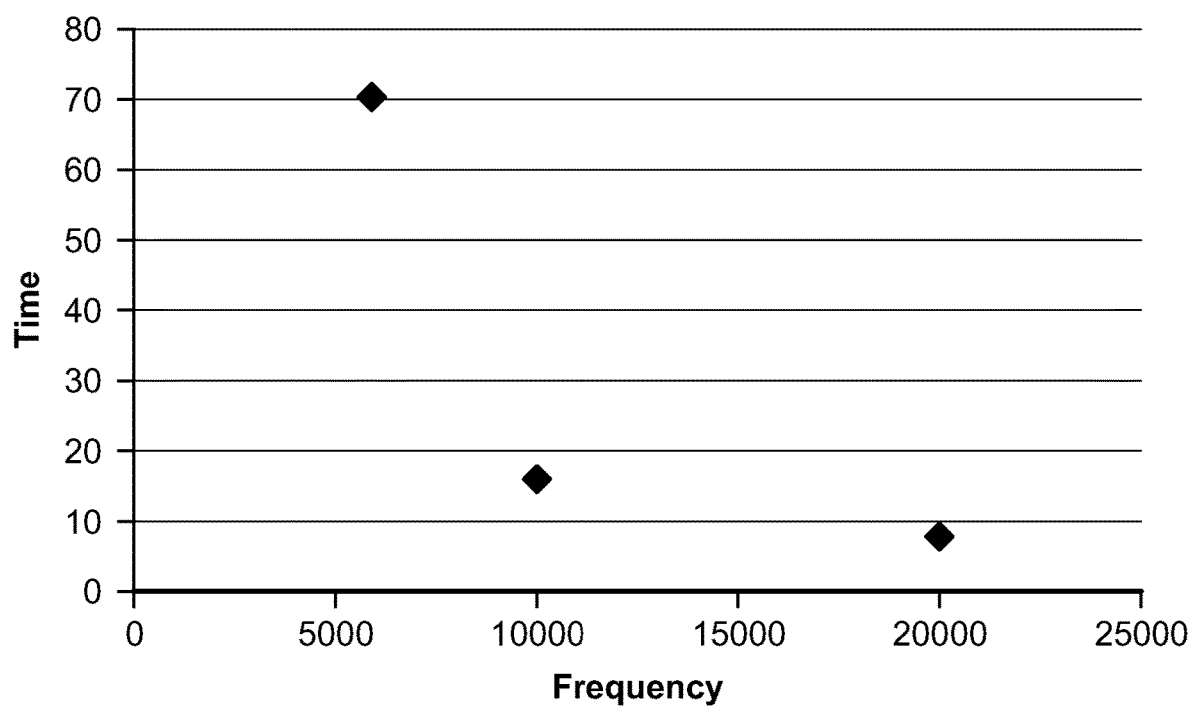
FIG. 10 is a graph depicting the time for the temperature to decay for various microwave frequencies.

With reference to FIG. 10, a graph illustrates the time, in seconds, for the temperature to decay from approximately 10° C. to 1° C. compared to microwave frequencies between 58 MHz and 20000 MHz. The minimum and maximum temperature decay for the preferred range of microwave frequencies are 8 seconds when the microwave frequency is 20 GHz, and 16 seconds when the microwave frequency is 10 GHz.

Utilizing ultrasound as an energy source enables heating of surface tissue, and tissues of varying depths in the body, including rather deep tissue. The absorption length of ultrasound in the body is rather long, as evidenced by its widespread use for imaging. Accordingly, ultrasound can be focused on target regions deep within the body, with the heating of a focused ultrasound beam concentrated mainly in the approximately cylindrical focal region of the beam. The heated region has a volume determined by the focal waist of the airy disc and the length of the focal waist region, that is the confocal parameter. Multiple beams from sources at different angles can also be used, the heating occurring at the overlapping focal regions.

For ultrasound, the relevant parameters for determining tissue temperature are frequency of the ultrasound, total train duration, and transducer power when the focal length and diameter of the ultrasound transducer is given. The frequency, focal length, and diameter determine the volume of the focal region where the ultrasound energy is concentrated. It is the focal volume that comprises the target volume of tissue for treatment. Transducers having a diameter of approximately 5 cm and having a focal length of approximately 10 cm are readily available. Favorable focal dimensions are achieved when the ultrasound frequency is between 1 and 5 MHz, and the total train duration is 0.1 to 0.5 seconds. For example, for a focal length of 10 cm and the transducer diameter of 5 cm, the focal volumes are 0.02 cc at 5 MHz and 2.36 cc at 1 MHz.

Figure 11:
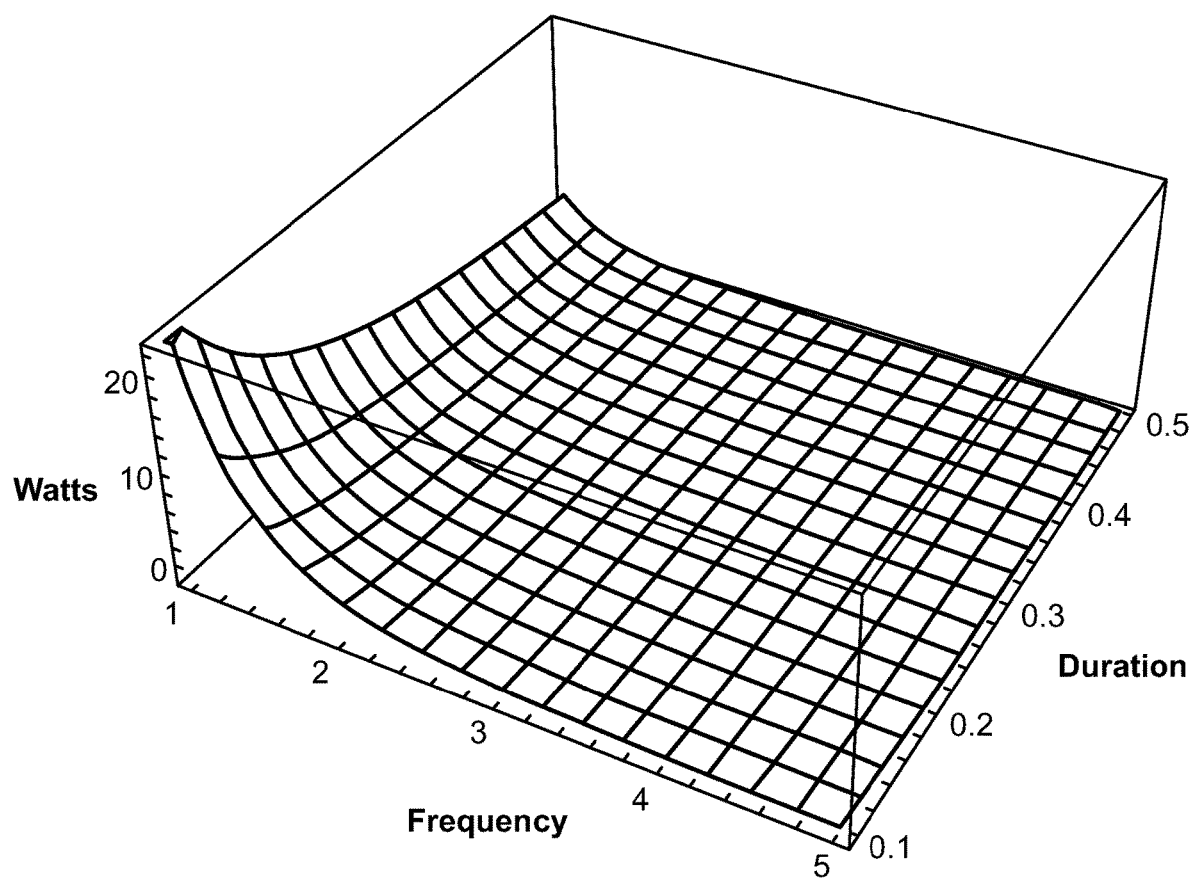
FIG. 11 is a graph depicting the average ultrasound source power compared to frequency and pulse train duration.

With reference now to FIG. 11, a graph illustrates the average source power in watts compared to the frequency (between 1 MHz and 5 MHz), and the pulse train duration (between 0.1 and 0.5 seconds). A transducer focal length of 10 cm and a source diameter of 5 cm have been assumed. The required power to give the Arrhenius integral for HSP activation of approximately 1 decreases monotonically as the frequency increases and as the total train duration increases. Given the preferred parameters, the minimum power for a frequency of 1 GHz and a pulse train duration of 0.5 seconds is 5.72 watts, whereas for the 1 GHz frequency and a pulse train duration of 0.1 seconds the maximum power is 28.6 watts. For a 5 GHz frequency, 0.046 watts is required for a pulse train duration of 0.5 seconds, wherein 0.23 watts is required for a pulse train duration of 0.1 seconds. The corresponding peak power during an individual pulse is obtained simply by dividing by the duty cycle.

Figure 12:
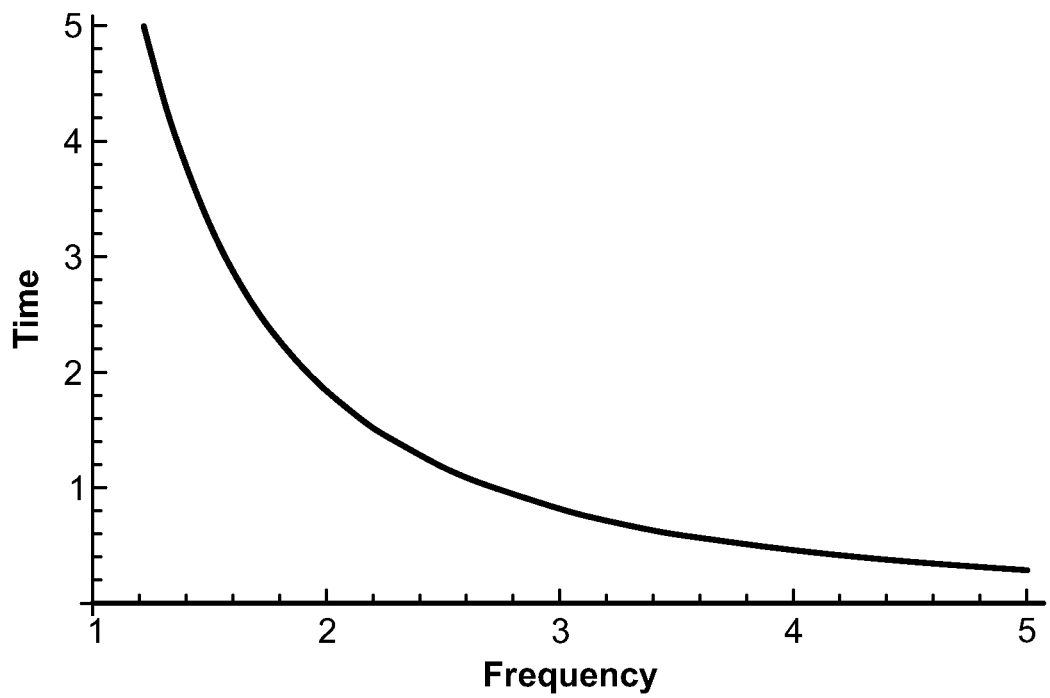
FIGS. 12 and 13 are graphs depicting the time for temperature decay for various ultrasound frequencies.
Figure 13:
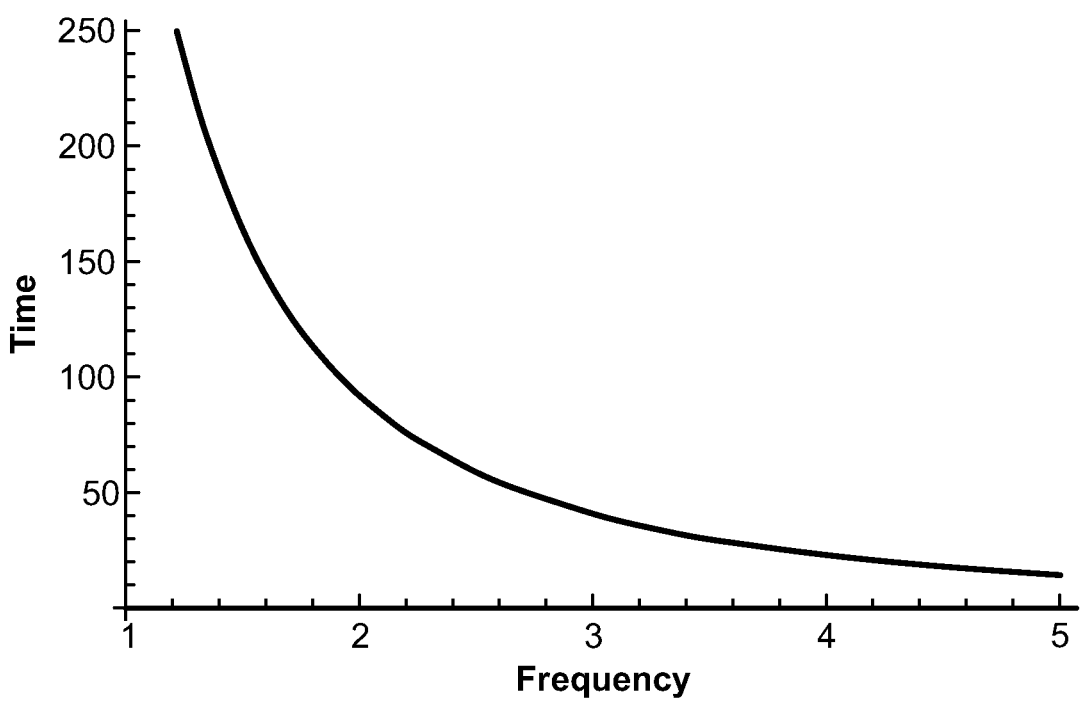

FIG. 12 illustrates the time, in seconds, for the temperature to diffuse or decay from 10° C. to 6° C. when the ultrasound frequency is between 1 and 5 MHz. FIG. 13 illustrates the time, in seconds, to decay from approximately 10° C. to approximately 1° C. for ultrasound frequencies from 1 to 5 MHz. For the preferred focal length of 10 cm and the transducer diameter of 5 cm, the maximum time for temperature decay is 366 seconds when the ultrasound frequency is 1 MHz, and the minimum temperature decay is 15 seconds when the microwave frequency is 5 MHz. As the FDA only requires the temperature rise be less than 6° C. for test times of minutes, the 366 second decay time at 1 MHz to get to a rise of 1° C. over the several minutes is allowable. As can be seen in FIGS. 12 and 13, the decay times to a rise of 6° C. are much smaller, by a factor of approximately 70, than that of 1° C.

Figure 14:
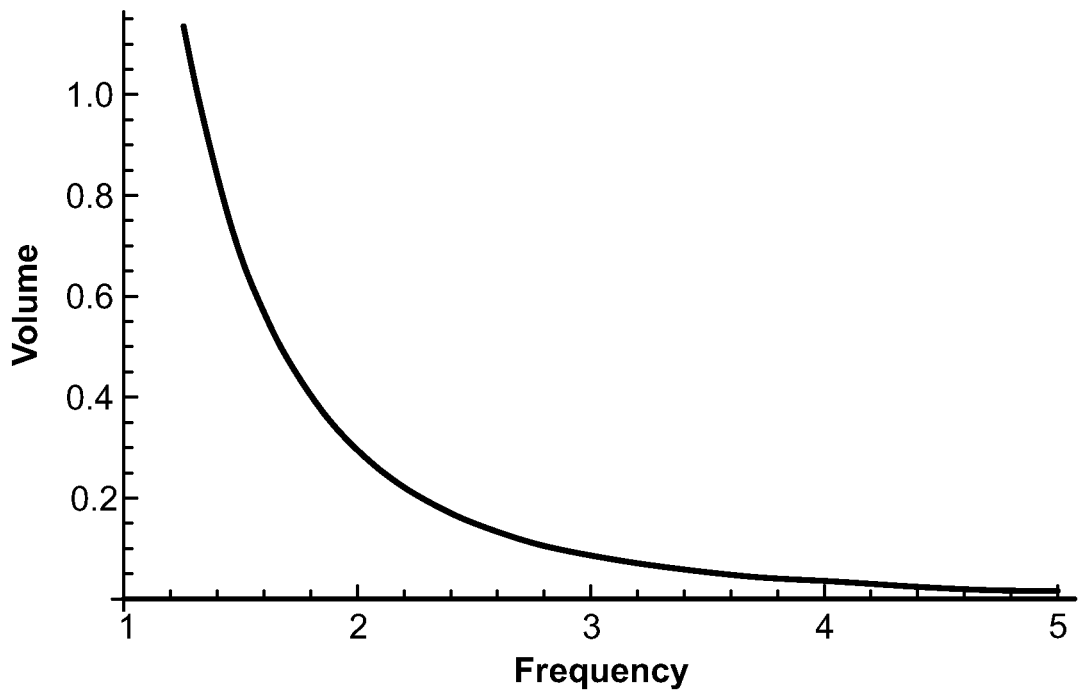
FIG. 14 is a graph depicting the volume of focal heated region compared to ultrasound frequency.

FIG. 14 illustrates the volume of focal heated region, in cubic centimeters, as compared to ultrasound frequencies from between 1 and 5 MHz. Considering ultrasound frequencies in the range of 1 to 5 MHz, the corresponding focal sizes for these frequencies range from 3.7 mm to 0.6 mm, and the length of the focal region ranges from 5.6 cm to 1.2 cm. The corresponding treatment volumes range from between approximately 2.4 cc and 0.02 cc.

Examples of parameters giving a desired HSP activation Arrhenius integral greater than 1 and damage Arrhenius integral less than 1 is a total ultrasound power between 5.8-17 watts, a pulse duration of 0.5 seconds, an interval between pulses of 5 seconds, with total number of pulses 10 within the total pulse stream time of 50 seconds. The target treatment volume would be approximately 1 mm on a side. Larger treatment volumes could be treatable by an ultrasound system similar to a laser diffracted optical system, by applying ultrasound in multiple simultaneously applied adjacent but separated and spaced columns. The multiple focused ultrasound beams converge on a very small treatment target within the body, the convergence allowing for a minimal heating except at the overlapping beams at the target. This area would be heated and stimulate the activation of HSPs and facilitate protein repair by transient high temperature spikes. However, given the pulsating aspect of the invention as well as the relatively small area being treated at any given time, the treatment is in compliance with FDA/FCC requirements for long term (minutes) average temperature rise <1K. An important distinction of the invention from existing therapeutic heating treatments for pain and muscle strain is that there are no high T spikes in existing techniques, and these are required for efficiently activating HSPs and facilitating protein repair to provide healing at the cellular level.

The pulse train mode of energy delivery has a distinct advantage over a single pulse or gradual mode of energy delivery, as far as the activation of remedial HSPs and the facilitation of protein repair is concerned. There are two considerations that enter into this advantage:

First, a big advantage for HSP activation and protein repair in an SDM energy delivery mode comes from producing a spike temperature of the order of 10° C. This large rise in temperature has a big impact on the Arrhenius integrals that describe quantitatively the number of HSPs that are activated and the rate of water diffusion into the proteins that facilitates protein repair. This is because the temperature enters into an exponential that has a big amplification effect.

It is important that the temperature rise not remain at the high value (10° C. or more) for long, because then it would violate the FDA and FCC requirements that over periods of minutes the average temperature rise must be less than 1° C. (or in the case of ultrasound 6° C.).

An SDM mode of energy delivery uniquely satisfies both of these foregoing considerations by judicious choice of the power, pulse time, pulse interval, and the volume of the target region to be treated. The volume of the treatment region enters because the temperature must decay from its high value of the order of 10° C. fairly rapidly in order for the long term average temperature rise not to exceed the long term FDA/FCC limit of 6° C. for ultrasound frequencies and 1° C. or less for electromagnetic radiation energy sources.

For a region of linear dimension L, the time that it takes the peak temperature to e-fold in tissue is roughly $L^2/16 D$, where $D=0.00143$ $cm^2/sec$ is the typical heat diffusion coefficient. For example, if L=1 mm, the decay time is roughly 0.4 sec. Accordingly, for a region 1 mm on a side, a train consisting of 10 pulses each of duration 0.5 seconds, with an interval between pulses of 5 second can achieve the desired momentary high rise in temperature while still not exceeding an average long term temperature rise of 1° C. This is demonstrated further below.

The limitation of heated volume is the reason why RF electromagnetic radiation is not as good of a choice for SDM-type treatment of regions deep with the body as ultrasound. The long skin depths (penetration distances) and Ohmic heating all along the skin depth results in a large heated volume whose thermal inertia does not allow both the attainment of a high spike temperature that activates HSPs and facilitates protein repair, and the rapid temperature decay that satisfies the long term FDA and FCC limit on average temperature rise.

Ultrasound has already been used to therapeutically heat regions of the body to ease pain and muscle strain. However, the heating has not followed the SDM-type protocol and does not have the temperature spikes that are responsible for the excitation of HSPs.

Consider, then, a group of focused ultrasound beams that are directed at a target region deep within the body. To simplify the mathematics, suppose that the beams are replaced by a single source with a spherical surface shape that is focused on the center of the sphere. The absorption lengths of ultrasound can be fairly long. Table 3 below shows typical absorption coefficients for ultrasound at 1 MHz. The absorption coefficients are roughly proportional to the frequency.

TABLE 3

Typical absorption coefficients for 1 MHz ultrasound in body tissue:

| Body Tissue | Attenuation Coefficient at 1 MHz (cm$^{-1}$) |
| --- | --- |
| Water | 0.00046 |
| Blood | 0.0415 |
| Fat | 0.145 |
| Liver | 0.115-0.217 |
| Kidney | 0.23 |
| Muscle | 0.3-0.76 |
| Bone | 1.15 |

Assuming that the geometric variation of the incoming radiation due to the focusing dominates any variation due to attenuation, the intensity of the incoming ultrasound at a distance r from the focus can be written approximately as:

$$I(r) = P/(4\pi r^2) \quad [1]$$

where P denotes the total ultrasound power.
The temperature rise at the end of a short pulse of duration $t_p$ at r is then $$dT(t_p) = P\alpha t_p/(4\pi C_v r^2) \quad [2]$$

where $\alpha$ is the absorption coefficient and $C_v$ is the specific volume heat capacity. This will be the case until the r is reached at which the heat diffusion length at $t_p$ becomes comparable to r, or the diffraction limit of the focused beam is reached. For smaller r, the temperature rise is essentially independent of r. As an example, suppose the diffraction limit is reached at a radial distance that is smaller than that determined by heat diffusion. Then $$r_{dif} = (4Dt_p)^{1/2} \quad [3]$$

where D is the heat diffusion coefficient, and for $r < r_{dif}$, the temperature rise at $t_p$ is $$dT(r_{dif}, t_p) = 3P\alpha/(8\pi C_v D) \text{ when } r < r_{dif} \quad [4]$$

Thus, at the end of the pulse, we can write for the temperature rise:

$$dT_p(r) = \{P\alpha t_p/(4\pi C_v)\}[(6/r_{dif}^2) \cup \{r_{dif}-r\} + (1/r^2) \cup (r-r_{dif})] \quad [5]$$

On applying the Green's function for the heat diffusion equation, $$G(r,t) = (4\Omega Dt)^{-3/2} \exp[-r^2/(4Dt)] \quad [6]$$

to this initial temperature distribution, we find that the temperature dT(t) at the focal point r=0 at a time t is $$dT(t) = [dT_o/\{(\frac{1}{2}) \pm (\pi^{1/2}/6)\}][(\frac{1}{2})(t_p/t)^{3/2} + (\pi^{1/2}/6)(t_p/t)] \quad [7]$$

with $$dT_o = 3P\alpha/(8\pi C_v D) \quad [8]$$

Figure 15:
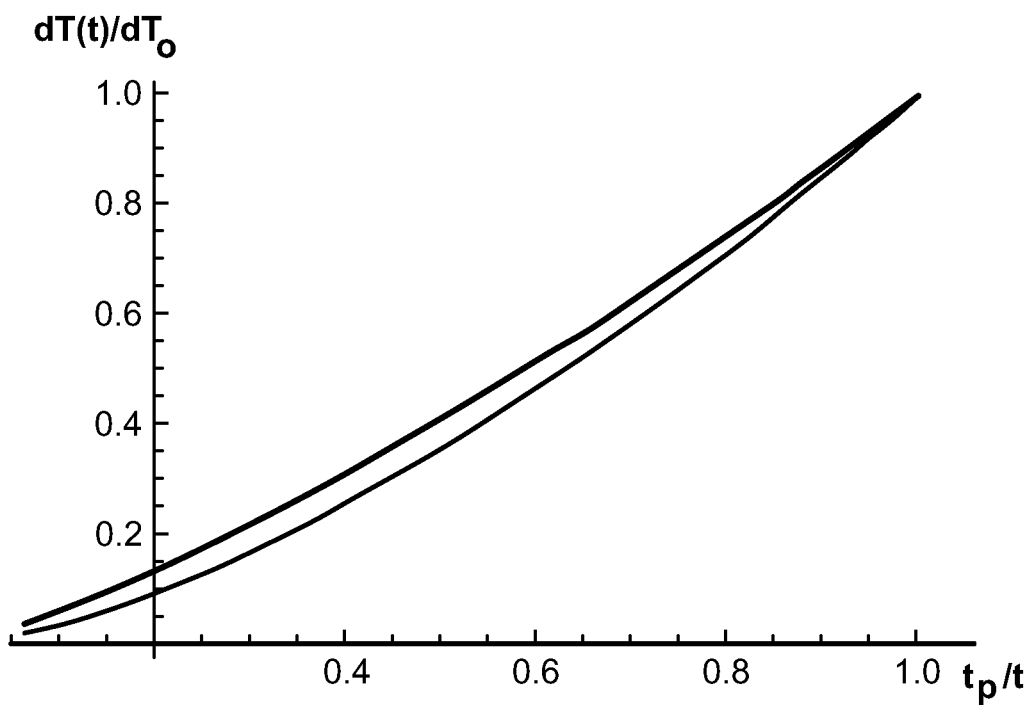
FIG. 15 is a graph comparing equations for temperature over pulse durations for an ultrasound energy source.

A good approximation to eq. [7] is provided by:

$$dT(t) \approx dT_o(t_p/t)^{3/2} \quad [9]$$

as can be seen in FIG. 15, which is a comparison of eqs. [7] and [9] for dT(t)/dT$_o$ at the target treatment zone. The bottom curve is the approximate expression of eq [9].
The Arrhenius integral for a train of N pulses can now be evaluated with the temperature rise given by eq. [9]. In this expression, $$dT_N(t) = \Sigma dT(t - nt_I) \quad [11]$$

where dT(t–nt$_I$) is the expression of eq. [9] with t replaced by t–nt$_I$ and with ti designating the interval between pulses.

The Arrhenius integral can be evaluated approximately by dividing the integration interval into the portion where the temperature spikes occur and the portion where the temperature spike is absent. The summation over the temperature spike contribution can be simplified by applying Laplace's end point formula to the integral over the temperature spike. In addition, the integral over the portion when the spikes are absent can be simplified by noting that the non-spike temperature rise very rapidly reaches an asymptotic value, so that a good approximation is obtained by replacing the varying time rise by its asymptotic value. When these approximations are made, eq. [10] becomes:

$$\Omega = AN[\{t_p(2k_B T_o^2/(3EdT_o)\}\exp[-(E/k_B)1/(T_o+dT_o+dT_N(Nt_I))]+\exp[-(E/k_B)1/(T_o+dT_N(Nt_I))]] \quad [12]$$

where $$dT_N(Nt_I) \approx 2.5 dT_o(t_p/t_I)^{3/2} \quad [13]$$

(The 2.5 in eq. [13] arises from the summation over n of (N–n)$^{-3/2}$ and is the magnitude of the harmonic number (N,3/2) for typical N of interest.)

It is interesting to compare this expression with that for SDM applied to the retina. The first term is very similar to that from the spike contribution in the retina case, except that the effective spike interval is reduced by a factor of 3 for this 3D converging beam case. The second term, involving dT$_N$(Nt$_I$) is much smaller than in the retina case. There the background temperature rise was comparable in magnitude to the spike temperature rise. But here in the converging beam case, the background temperature rise is much smaller by the ratio $(t_p/t_I)^{3/2}$. This points up the importance of the spike contribution to the activation or production of HSP's and the facilitation of protein repair, as the background temperature rise which is similar to the rise in a continuous ultrasound heating case is insignificant compared to the spike contribution. At the end of the pulse train, even this low background temperature rise rapidly disappears by heat diffusion.

Figure 16:
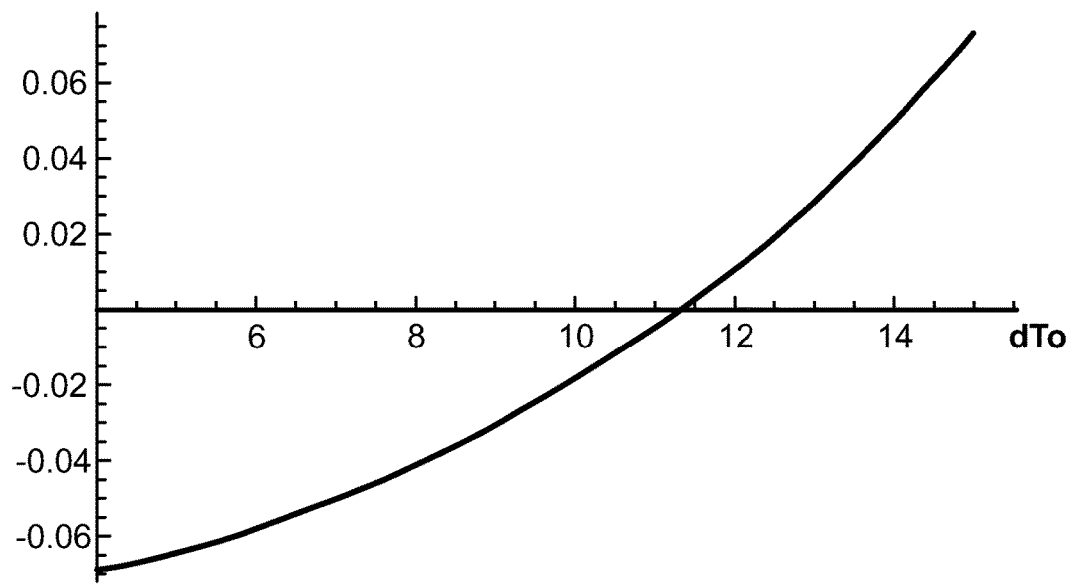
FIGS. 16 and 17 are graphs illustrating the magnitude of the logarithm of damage and HSP activation Arrhenius integrals as a function of temperature and pulse duration.
Figure 17:
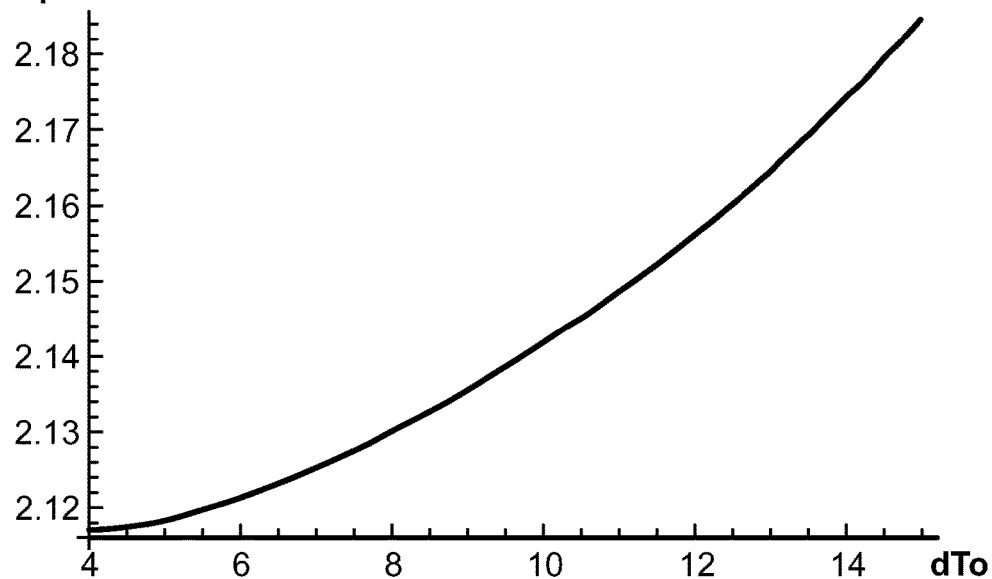

FIGS. 16 and 17 show the magnitude of the logarithm of the Arrhenius integrals for damage and for HSP activation or production as a function of dT$_o$ for a pulse duration t$_o$=0.5 sec, pulse interval t$_I$=10 sec, and total number of pulses N=10. Logarithm of Arrhenius integrals [eq. 12] for damage and for HSP activation as a function of the temperature rise in degrees Kelvin from a single pulse dT$_o$, for a pulse duration t$_o$=0.5 sec., pulse interval t$_I$=10 sec., and a total number of ultrasound pulses N=10. FIG. 16 shows the logarithm of the damage integral with the Arrhenius constants A=8.71×10$^{33}$ sec$^{-1}$ and E=3.55×10$^{-12}$ ergs. FIG. 17 shows the logarithm of the HSP activation integral with the Arrhenius constants A=1.24×10$^{27}$ sec$^{-1}$ and E=2.66×10$^{-12}$ ergs. The graphs in FIGS. 16 and 17 show that $\Omega_{damage}$ does not exceed 1 until dT$_o$ exceeds 11.3 K, whereas $\Omega_{hsp}$ is greater than 1 over the whole interval shown, the desired condition for cellular repair without damage.

Equation [8] shows that when $\alpha$=0.1 cm$^{-1}$, a dT$_o$ of 11.5 K can be achieved with a total ultrasound power of 5.8 watts. This is easily achievable. If $\alpha$ is increased by a factor of 2 or 3, the resulting power is still easily achievable. The volume of the region where the temperature rise is constant (i.e. the volume corresponding to $r=r_d=(4Dt_p)^{1/2}$) is 0.00064 cc. This corresponds to a cube that is 0.86 mm on a side.

This simple example demonstrates that focused ultrasound should be usable to stimulate reparative HSP's deep in the body with easily attainable equipment:

Total ultrasound power: 5.8 watts-17 watts
Pulse time 0.5 sec
Pulse interval 5 sec
Total train duration (N=10) 50 sec To expedite the treatment of larger internal volumes, a SAPRA system can be used.

The pulsed energy source may be directed to an exterior of a body which is adjacent to the target tissue or has a blood supply close to the surface of the exterior of the body. Alternatively, a device may be inserted into a cavity of a body to apply the pulsed energy source to the target tissue. Whether the energy source is applied outside of the body or inside of the body and what type of device is utilized depends upon the energy source selected and used to treat the target tissue.

Photostimulation, in accordance with the present invention, can be effectively transmitted to an internal surface area or tissue of the body utilizing an endoscope, such as a bronchoscope, proctoscope, colonoscope or the like. Each of these consist essentially of a flexible tube that itself contains one or more internal tubes. Typically, one of the internal tubes comprises a light pipe or multi-mode optical fiber which conducts light down the scope to illuminate the region of interest and enable the doctor to see what is at the illuminated end. Another internal tube could consist of wires that carry an electrical current to enable the doctor to cauterize the illuminated tissue. Yet another internal tube might consist of a biopsy tool that would enable the doctor to snip off and hold on to any of the illuminated tissue.

Figure 18:
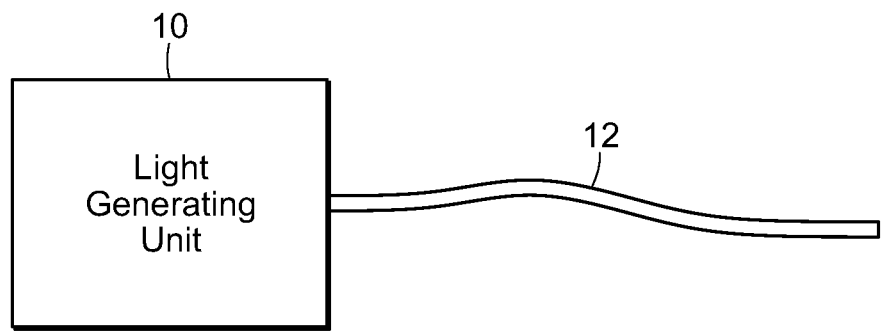
FIG. 18 is a diagrammatic view of a light generating unit that produces timed series of pulses, having a light pipe extending therefrom, in accordance with the present invention.
Figure 19:
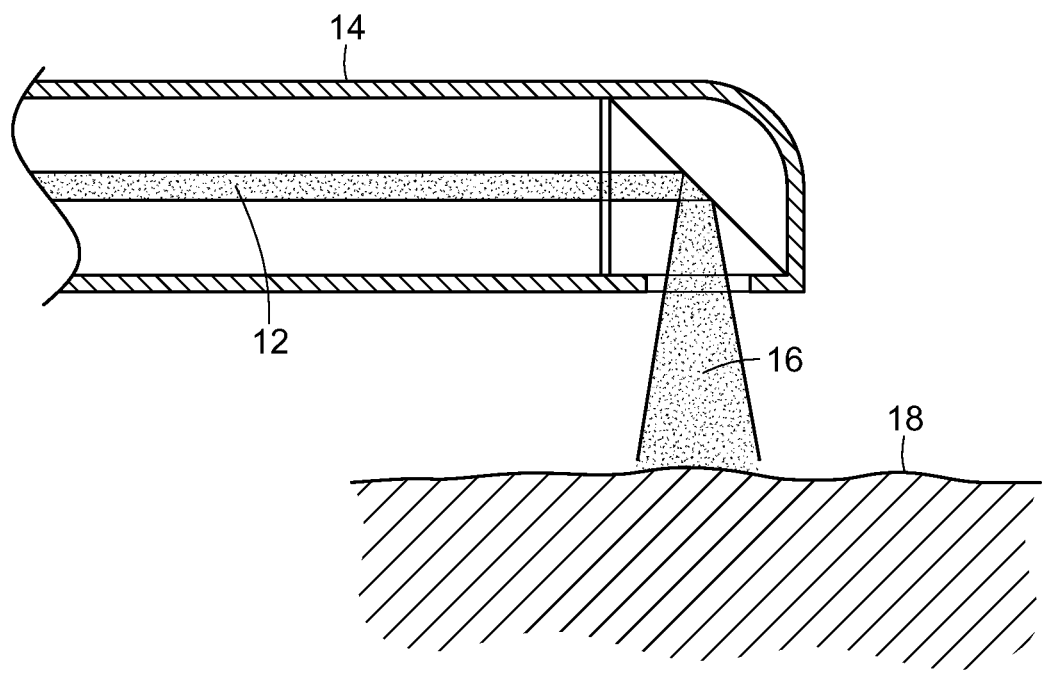
FIG. 19 is a cross-sectional view of a photostimulation delivery device delivering electromagnetic energy to target tissue, in accordance with the present invention.

In the present invention, one of these internal tubes is used as an electromagnetic radiation pipe, such as a multi-mode optical fiber, to transmit the SDM or other electromagnetic radiation pulses that are fed into the scope at the end that the doctor holds. With reference now to FIG. 18, a light generating unit 10, such as a laser having a desired wavelength and/or frequency is used to generate electromagnetic radiation, such as laser light, in a controlled, pulsed manner to be delivered through a light tube or pipe 12 to a distal end of the scope 14, illustrated in FIG. 19, which is inserted into the body and the laser light or other radiation 16 delivered to the target tissue 18 to be treated.

Figure 20:
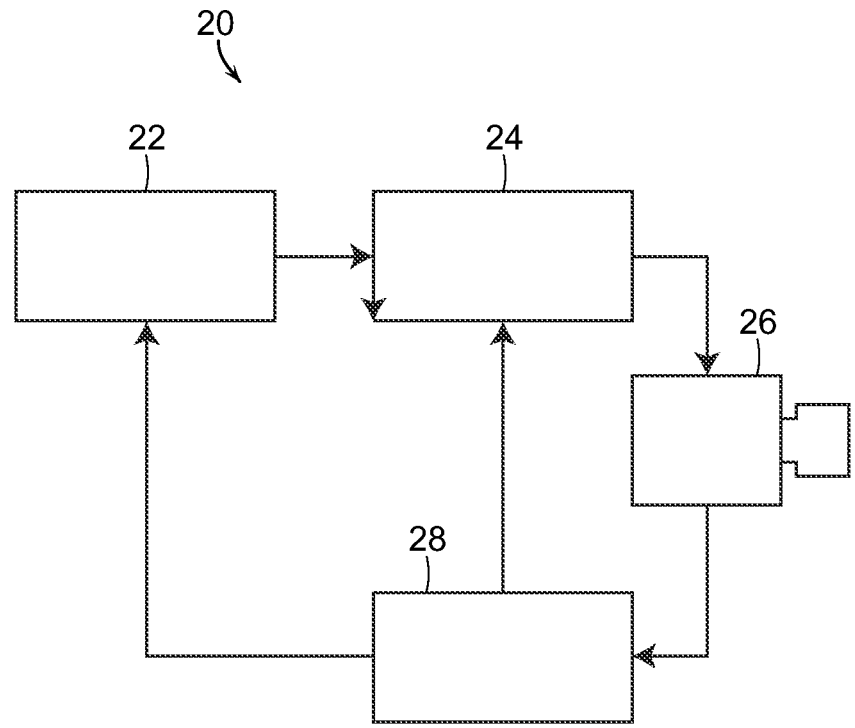
FIG. 20 is a diagrammatic view illustrating a system used to generate a laser light beam, in accordance with the present invention.

With reference now to FIG. 20, a schematic diagram is shown of a system for generating electromagnetic energy radiation, such as laser light, including SDM. The system, generally referred to by the reference number 20, includes a laser console 22, such as for example the 810 nm near infrared micropulsed diode laser in the preferred embodiment. The laser generates a laser light beam which is passed through optics, such as an optical lens or mask, or a plurality of optical lenses and/or masks 24 as needed. The laser projector optics 24 pass the shaped light beam to a delivery device 26, such as an endoscope, for projecting the laser beam light onto the target tissue of the patient. It will be understood that the box labeled 26 can represent both the laser beam projector or delivery device as well as a viewing system/camera, such as an endoscope, or comprise two different components in use. The viewing system/camera 26 provides feedback to a display monitor 28, which may also include the necessary computerized hardware, data input and controls, etc. for manipulating the laser 22, the optics 24, and/or the projection/viewing components 26.

Figure 21:
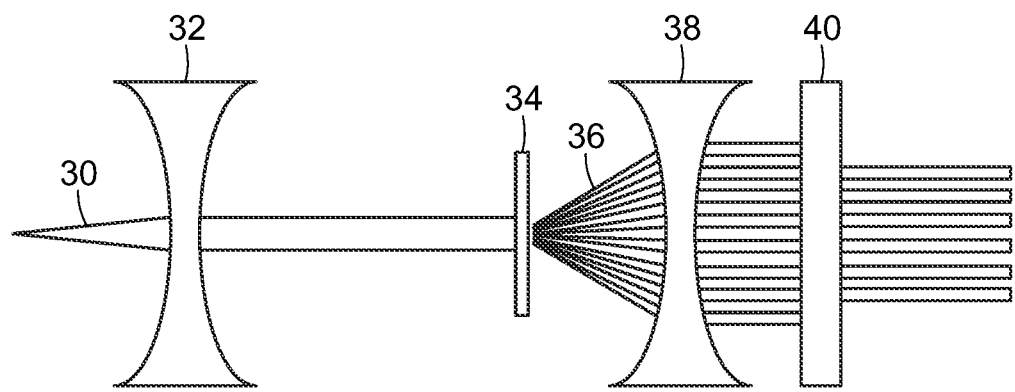
FIG. 21 is a diagrammatic view of optics used to generate a laser light geometric pattern, in accordance with the present invention.

With reference now to FIG. 21, in one embodiment, a plurality of light beams are generated, each of which has parameters selected so that a target tissue temperature may be controllably raised to therapeutically treat the target tissue without destroying or permanently damaging the target tissue. This may be done, for example, by passing the laser light beam 30 through optics which diffract or otherwise generate a plurality of laser light beams from the single laser light beam 30 having the selected parameters. For example, the laser light beam 30 may be passed through a collimator lens 32 and then through a mask 34. In a particularly preferred embodiment, the mask 34 comprises a diffraction grating. The mask/diffraction grating 34 produces a geometric object, or more typically a geometric pattern of simultaneously produced multiple laser spots or other geometric objects. This is represented by the multiple laser light beams labeled with reference number 36. Alternatively, the multiple laser spots may be generated by a plurality of fiber optic waveguides. Either method of generating laser spots allows for the creation of a very large number of laser spots simultaneously over a very wide treatment field. In fact, a very high number of laser spots, perhaps numbering in the hundreds even thousands or more could be simultaneously generated to cover a given area of the target tissue, or possibly even the entirety of the target tissue. A wide array of simultaneously applied small separated laser spot applications may be desirable as such avoids certain disadvantages and treatment risks known to be associated with large laser spot applications.

Using optical features with a feature size on par with the wavelength of the laser employed, for example using a diffraction grating, it is possible to take advantage of quantum mechanical effects which permits simultaneous application of a very large number of laser spots for a very large target area. The individual spots produced by such diffraction gratings are all of a similar optical geometry to the input beam, with minimal power variation for each spot. The result is a plurality of laser spots with adequate irradiance to produce harmless yet effective treatment application, simultaneously over a large target area. The present invention also contemplates the use of other geometric objects and patterns generated by other diffractive optical elements.

The laser light passing through the mask 34 diffracts, producing a periodic pattern a distance away from the mask 34, shown by the laser beams labeled 36 in FIG. 21. The single laser beam 30 has thus been formed into hundreds or even thousands of individual laser beams 36 so as to create the desired pattern of spots or other geometric objects. These laser beams 36 may be passed through additional lenses, collimators, etc. 38 and 40 in order to convey the laser beams and form the desired pattern. Such additional lenses, collimators, etc. 38 and 40 can further transform and redirect the laser beams 36 as needed.

Arbitrary patterns can be constructed by controlling the shape, spacing and pattern of the optical mask 34. The pattern and exposure spots can be created and modified arbitrarily as desired according to application requirements by experts in the field of optical engineering. Photolithographic techniques, especially those developed in the field of semiconductor manufacturing, can be used to create the simultaneous geometric pattern of spots or other objects.

The present invention can use a multitude of simultaneously generated therapeutic light beams or spots, such as numbering in the dozens or even hundreds, as the parameters and methodology of the present invention create therapeutically effective yet non-destructive and non-permanently damaging treatment. Although hundreds or even thousands of simultaneous laser spots could be generated and created and formed into patterns to be simultaneously applied to the tissue, due to the requirements of not overheating the tissue, there are constraints on the number of treatment spots or beams which can be simultaneously used in accordance with the present invention. Each individual laser beam or spot requires a minimum average power over a train duration to be effective. However, at the same time, tissue cannot exceed certain temperature rises without becoming damaged. For example, using an 810 nm wavelength laser, the number of simultaneous spots generated and used could number from as few as 1 and up to approximately 100 when a 0.04 (4%) duty cycle and a total train duration of 0.3 seconds (300 milliseconds) is used. The water absorption increases as the wavelength is increased. For shorter wavelengths, e.g., 577 nm, the laser power can be lower. For example, at 577 nm, the power can be lowered by a factor of 4 for the invention to be effective. Accordingly, there can be as few as a single laser spot or up to approximately 400 laser spots when using the 577 nm wavelength laser light, while still not harming or damaging the tissue.

Typically, the system of the present invention incorporates a guidance system to ensure complete and total retinal treatment with retinal photostimulation. Fixation/tracking/registration systems consisting of a fixation target, tracking mechanism, and linked to system operation can be incorporated into the present invention. In a particularly preferred embodiment, the geometric pattern of simultaneous laser spots is sequentially offset so as to achieve confluent and complete treatment of the surface.

Figure 22:
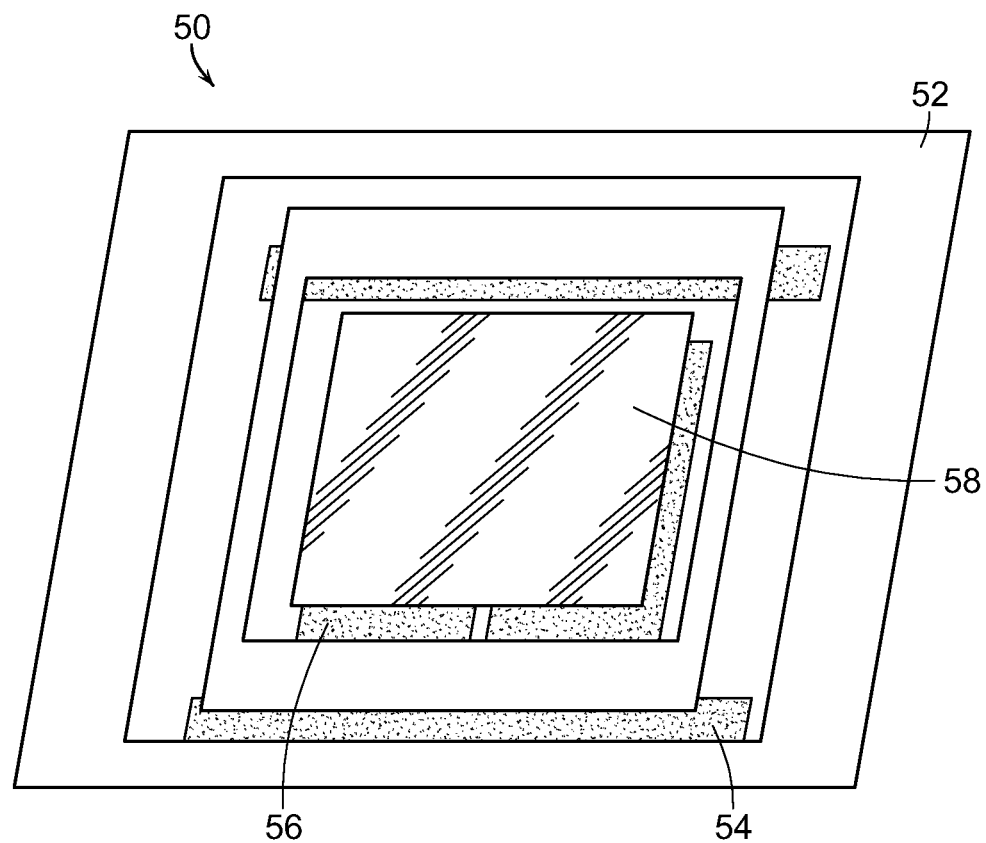
FIG. 22 is a top plan view of an optical scanning mechanism, used in accordance with the present invention.
Figure 23:
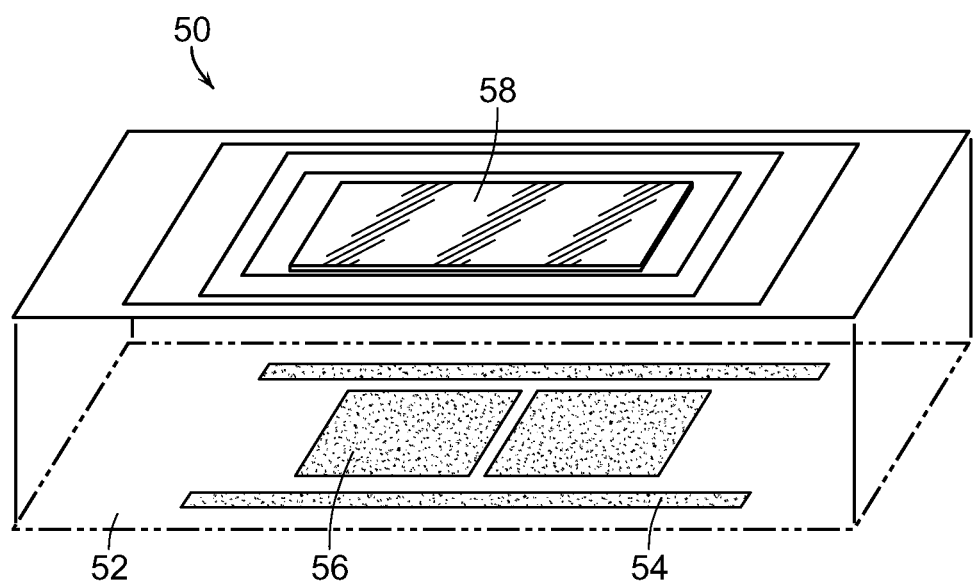
FIG. 23 is a partially exploded view of the optical scanning mechanism of FIG. 22, illustrating the various component parts thereof.

This can be done in a controlled manner using an optical scanning mechanism 50. FIGS. 22 and 23 illustrate an optical scanning mechanism 50 in the form of a MEMS mirror, having a base 52 with electronically actuated controllers 54 and 56 which serve to tilt and pan the mirror 58 as electricity is applied and removed thereto. Applying electricity to the controller 54 and 56 causes the mirror 58 to move, and thus the simultaneous pattern of laser spots or other geometric objects reflected thereon to move accordingly on the retina of the patient. This can be done, for example, in an automated fashion using electronic software program to adjust the optical scanning mechanism 50 until complete coverage of the retina, or at least the portion of the retina desired to be treated, is exposed to the phototherapy. The optical scanning mechanism may also be a small beam diameter scanning galvo mirror system, or similar system, such as that distributed by Thorlabs. Such a system is capable of scanning the lasers in the desired offsetting pattern.

Figure 24:
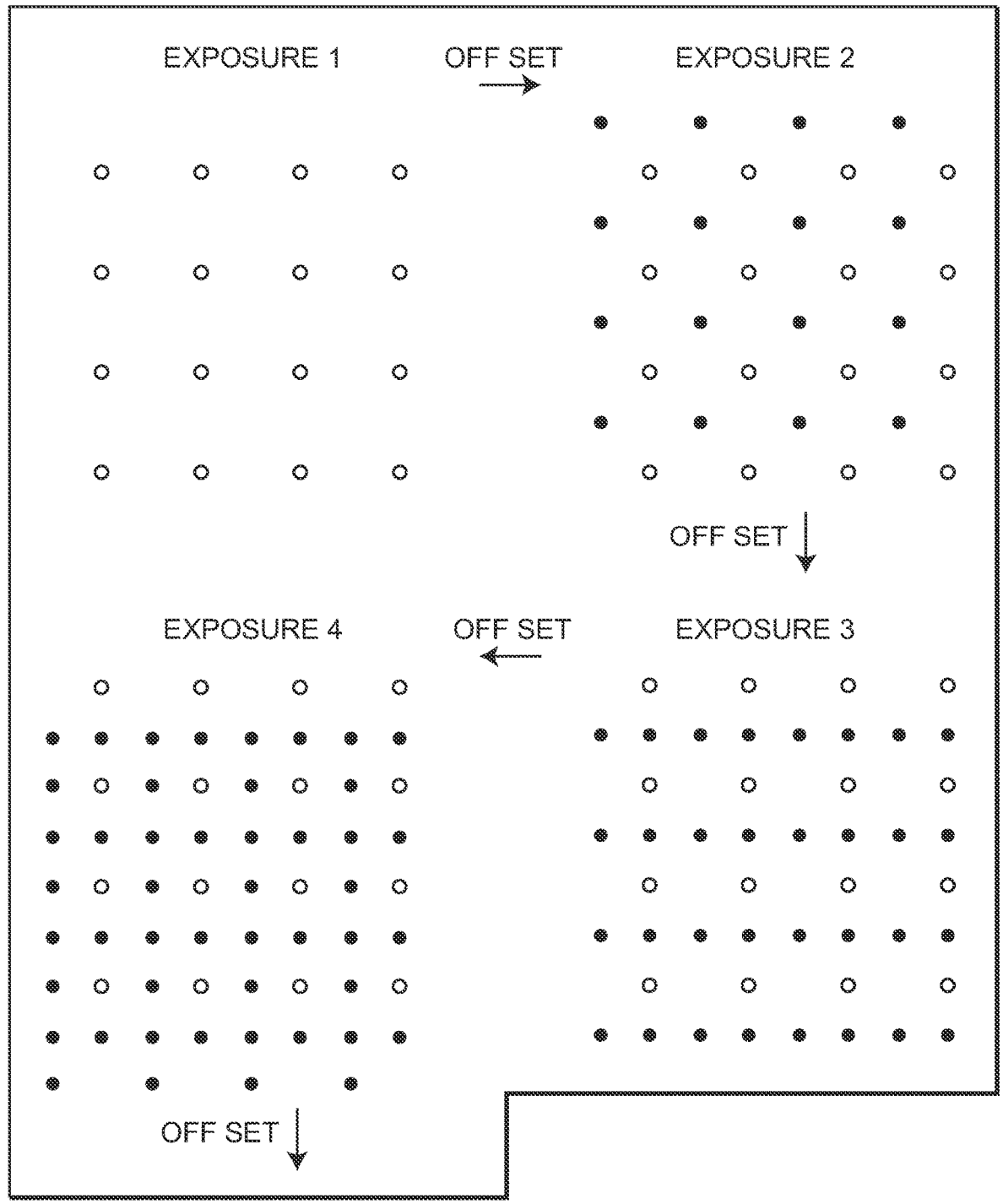
FIG. 24 illustrates controlled offsets of exposure of an exemplary geometric pattern grid of laser spots to treat the target tissue, in accordance with an embodiment of the present invention.

The pattern of spots are offset at each exposure so as to create space between the immediately previous exposure to allow heat dissipation and prevent the possibility of heat damage or tissue destruction. Thus, as illustrated in FIG. 24, the pattern, illustrated for exemplary purposes as a grid of sixteen spots, is offset each exposure such that the laser spots occupy a different space than previous exposures. It will be understood that the diagrammatic use of circles or empty dots as well as filled dots are for diagrammatic purposes only to illustrate previous and subsequent exposures of the pattern of spots to the area, in accordance with the present invention. The spacing of the laser spots prevents overheating and damage to the tissue. It will be understood that this occurs until the entire target tissue to be treated has received phototherapy, or until the desired effect is attained. This can be done, for example, by applying electrostatic torque to a micromachined mirror, as illustrated in FIGS. 22 and 23. By combining the use of small laser spots separated by exposure free areas, prevents heat accumulation, and grids with a large number of spots per side, it is possible to atraumatically and invisibly treat large target areas with short exposure durations far more rapidly than is possible with current technologies.

By rapidly and sequentially repeating redirection or offsetting of the entire simultaneously applied grid array of spots or geometric objects, complete coverage of the target, can be achieved rapidly without thermal tissue injury. This offsetting can be determined algorithmically to ensure the fastest treatment time and least risk of damage due to thermal tissue, depending on laser parameters and desired application.

The following has been modeled using the Fraunhoffer Approximation. With a mask having a nine by nine square lattice, with an aperture radius 9 µm, an aperture spacing of 600 µm, using a 890 nm wavelength laser, with a mask-lens separation of 75 mm, and secondary mask size of 2.5 mm by 2.5 mm, the following parameters will yield a grid having nineteen spots per side separated by 133 µm with a spot size radius of 6 µm. The number of exposures "m" required to treat (cover confluently with small spot applications) given desired area side-length "A", given output pattern spots per square side "n", separation between spots "R", spot radius "r" and desired square side length to treat area "A", can be given by the following formula:

$$m = \frac{A}{nR} \text{ floor } \left(\frac{R}{2r}\right)^2$$

With the foregoing setup, one can calculate the number of operations m needed to treat different field areas of exposure. For example, a 3 mm×3 mm area, which is useful for treatments, would require 98 offsetting operations, requiring a treatment time of approximately thirty seconds. Another example would be a 3 cm×3 cm area, representing the entire human retinal surface. For such a large treatment area, a much larger secondary mask size of 25 mm by 25 mm could be used, yielding a treatment grid of 190 spots per side separated by 133 µm with a spot size radius of 6 µm. Since the secondary mask size was increased by the same factor as the desired treatment area, the number of offsetting operations of approximately 98, and thus treatment time of approximately thirty seconds, is constant.

Of course, the number and size of spots produced in a simultaneous pattern array can be easily and highly varied such that the number of sequential offsetting operations required to complete treatment can be easily adjusted depending on the therapeutic requirements of the given application.

Furthermore, by virtue of the small apertures employed in the diffraction grating or mask, quantum mechanical behavior may be observed which allows for arbitrary distribution of the laser input energy. This would allow for the generation of any arbitrary geometric shapes or patterns, such as a plurality of spots in grid pattern, lines, or any other desired pattern. Other methods of generating geometric shapes or patterns, such as using multiple fiber optical fibers or microlenses, could also be used in the present invention. Time savings from the use of simultaneous projection of geometric shapes or patterns permits the treatment fields of novel size, such as the 1.2 cm^2 area to accomplish whole-retinal treatment, in a single clinical setting or treatment session.

Figure 25:
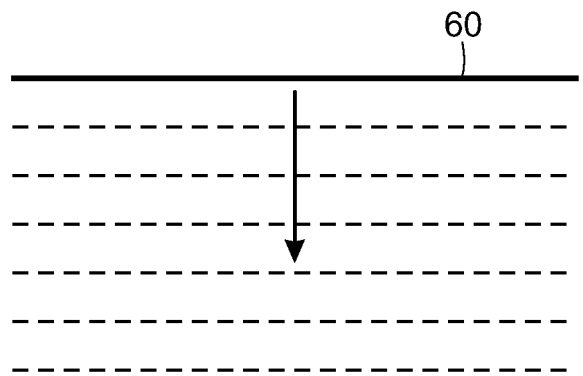
FIG. 25 is a diagrammatic view illustrating the use of a geometric object in the form of a line controllably scanned to treat an area of the target tissue.

With reference now to FIG. 25, instead of a geometric pattern of small laser spots, the present invention contemplates use of other geometric objects or patterns. For example, a single line 60 of laser light, formed by the continuously or by means of a series of closely spaced spots, can be created. An offsetting optical scanning mechanism can be used to sequentially scan the line over an area, illustrated by the downward arrow in FIG. 25.

Figure 26:
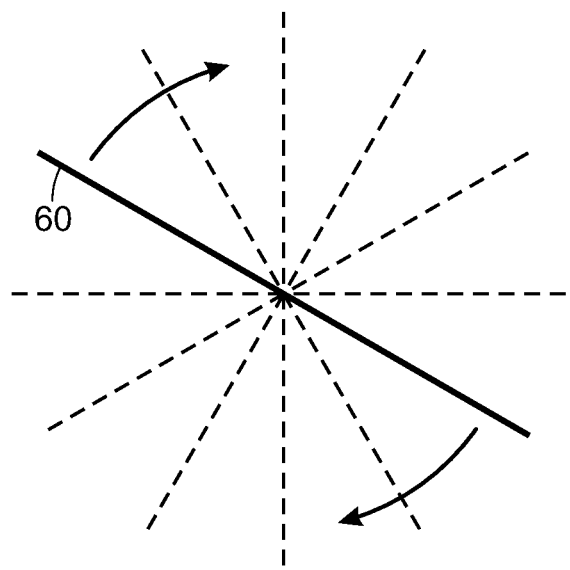
FIG. 26 is a diagrammatic view similar to FIG. 25, but illustrating the geometric line or bar rotated to treat the target tissue.

With reference now to FIG. 26, the same geometric object of a line 60 can be rotated, as illustrated by the arrows, so as to create a circular field of phototherapy. The potential negative of this approach, however, is that the central area will be repeatedly exposed, and could reach unacceptable temperatures. This could be overcome, however, by increasing the time between exposures, or creating a gap in the line such that the central area is not exposed.

The field of photobiology reveals that different biologic effects may be achieved by exposing target tissues to lasers of different wavelengths. The same may also be achieved by consecutively applying multiple lasers of either different or the same wavelength in sequence with variable time periods of separation and/or with different irradiant energies. The present invention anticipates the use of multiple laser, light or radiant wavelengths (or modes) applied simultaneously or in sequence to maximize or customize the desired treatment effects. This method also minimizes potential detrimental effects. The optical methods and systems illustrated and described above provide simultaneous or sequential application of multiple wavelengths.

Figure 27:
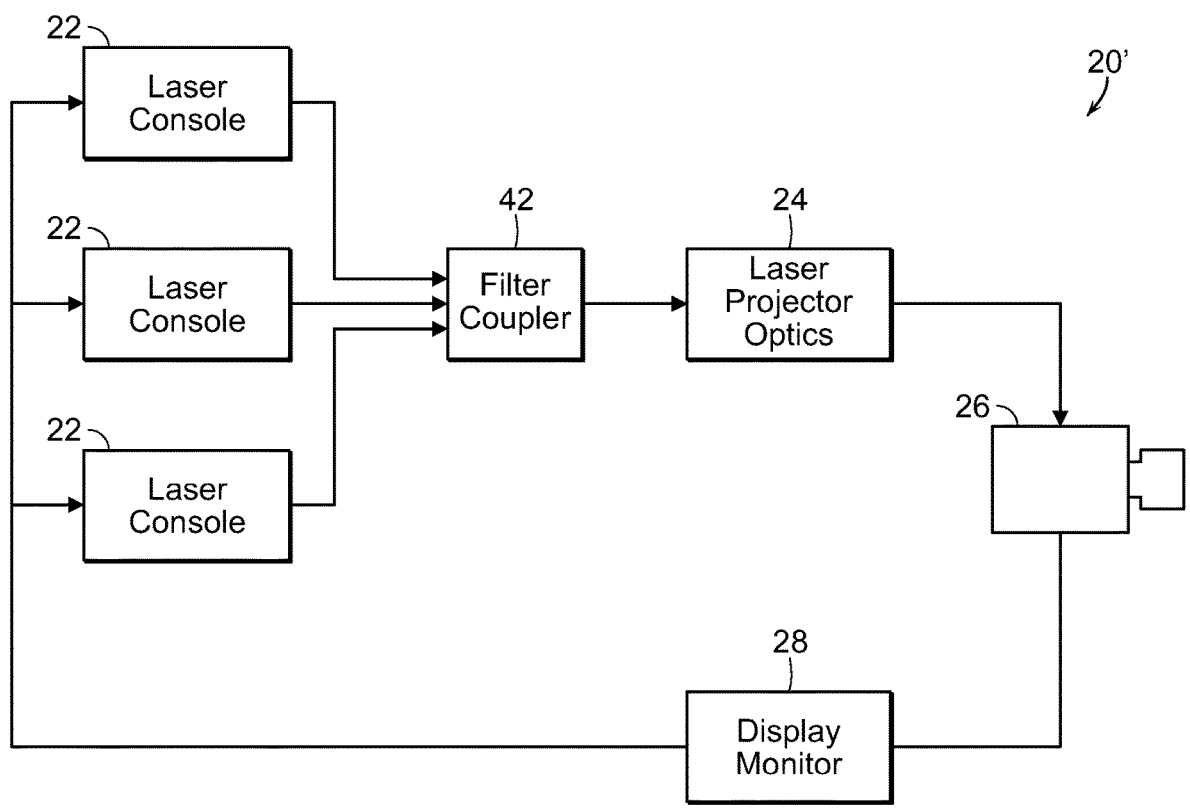
FIG. 27 is a diagrammatic view illustrating an alternate embodiment of the system used to generate laser light beams for treating tissue, in accordance with the present invention.

FIG. 27 illustrates diagrammatically a system which couples multiple treatment light sources into the pattern-generating optical subassembly described above. Specifically, this system 20' is similar to the system 20 described in FIG. 20 above. The primary differences between the alternate system 20' and the earlier described system 20 is the inclusion of a plurality of laser consoles, the outputs of which are each fed into a fiber coupler 42. Each laser console may supply a laser light beam having different parameters, such as of a different wavelength. The fiber coupler produces a single output that is passed into the laser projector optics 24 as described in the earlier system. The coupling of the plurality of laser consoles 22 into a single optical fiber is achieved with a fiber coupler 42 as is known in the art. Other known mechanisms for combining multiple light sources are available and may be used to replace the fiber coupler described herein.

In this system 20' the multiple light sources 22 follow a similar path as described in the earlier system 20, i.e., collimated, diffracted, recollimated, and directed to the projector device and/or tissue. In this alternate system 20' the diffractive element must function differently than described earlier depending upon the wavelength of light passing through, which results in a slightly varying pattern. The variation is linear with the wavelength of the light source being diffracted. In general, the difference in the diffraction angles is small enough that the different, overlapping patterns may be directed along the same optical path through the projector device 26 to the tissue for treatment.

Since the resulting pattern will vary slightly for each wavelength, a sequential offsetting to achieve complete coverage will be different for each wavelength. This sequential offsetting can be accomplished in two modes. In the first mode, all wavelengths of light are applied simultaneously without identical coverage. An offsetting steering pattern to achieve complete coverage for one of the multiple wavelengths is used. Thus, while the light of the selected wavelength achieves complete coverage of the tissue, the application of the other wavelengths achieves either incomplete or overlapping coverage of the tissue. The second mode sequentially applies each light source of a varying wavelength with the proper steering pattern to achieve complete coverage of the tissue for that particular wavelength. This mode excludes the possibility of simultaneous treatment using multiple wavelengths, but allows the optical method to achieve identical coverage for each wavelength. This avoids either incomplete or overlapping coverage for any of the optical wavelengths.

These modes may also be mixed and matched. For example, two wavelengths may be applied simultaneously with one wavelength achieving complete coverage and the other achieving incomplete or overlapping coverage, followed by a third wavelength applied sequentially and achieving complete coverage.

Figure 28:
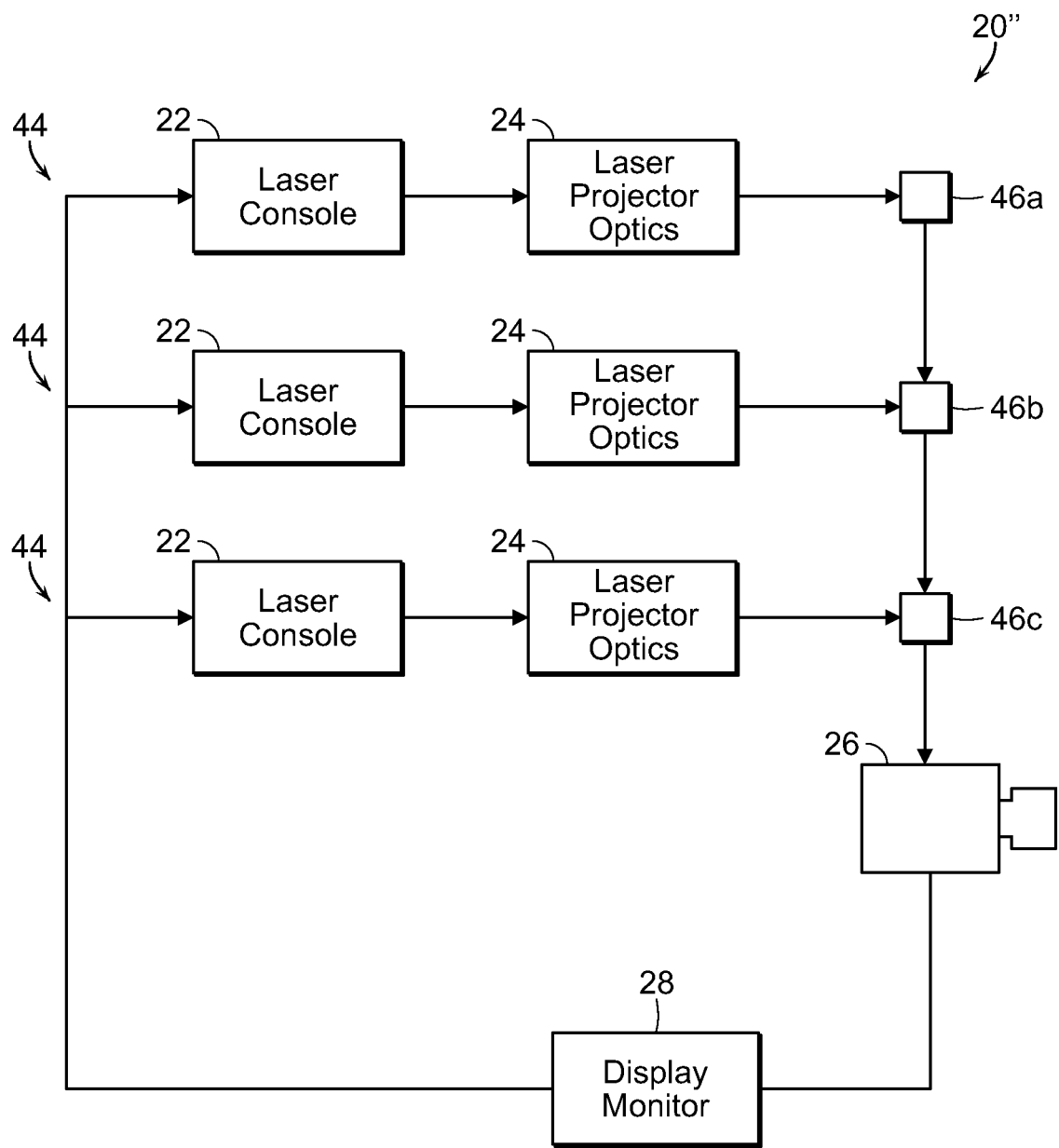
FIG. 28 is a diagrammatic view illustrating yet another embodiment of a system used to generate laser light beams to treat tissue in accordance with the present invention.

FIG. 28 illustrates diagrammatically yet another alternate embodiment of the inventive system 20". This system 20" is configured generally the same as the system 20 depicted in FIG. 20. The main difference resides in the inclusion of multiple pattern-generating subassembly channels tuned to a specific wavelength of the light source. Multiple laser consoles 22 are arranged in parallel with each one leading directly into its own laser projector optics 24. The laser projector optics of each channel 44a, 44b, 44c comprise a collimator 32, mask or diffraction grating 34 and recollimators 38, 40 as described in connection with FIG. 21 above—the entire set of optics tuned for the specific wavelength generated by the corresponding laser console 22. The output from each set of optics 24 is then directed to a beam splitter 46 for combination with the other wavelengths. It is known by those skilled in the art that a beam splitter used in reverse can be used to combine multiple beams of light into a single output. The combined channel output from the final beam splitter 46c is then directed through the projector device 26.

In this system 20" the optical elements for each channel are tuned to produce the exact specified pattern for that channel's wavelength. Consequently, when all channels are combined and properly aligned a single steering pattern may be used to achieve complete coverage of the tissue for all wavelengths. The system 20" may use as many channels 44a, 44b, 44c, etc. and beam splitters 46a, 46b, 46c, etc. as there are wavelengths of light being used in the treatment.

Implementation of the system 20" may take advantage of different symmetries to reduce the number of alignment constraints. For example, the proposed grid patterns are periodic in two dimensions and steered in two dimensions to achieve complete coverage. As a result, if the patterns for each channel are identical as specified, the actual pattern of each channel would not need to be aligned for the same steering pattern to achieve complete coverage for all wavelengths. Each channel would only need to be aligned optically to achieve an efficient combination.

In system 20", each channel begins with a light source 22, which could be from an optical fiber as in other embodiments of the pattern-generating subassembly. This light source 22 is directed to the optical assembly 24 for collimation, diffraction, recollimation and directed into the beam splitter which combines the channel with the main output.

It will be understood that the laser light generating systems illustrated in FIGS. 20-28 are exemplary. Other devices and systems can be utilized to generate a source of SDM laser light which can be operably passed through to a projector device, typically in the form of an endoscope having a light pipe or the like. Also, other forms of electromagnetic radiation may also be generated and used, including ultraviolet waves, microwaves, other radiofrequency waves, and laser light at predetermined wavelengths. Moreover, ultrasound waves may also be generated and used to create a thermal time-course temperature spike in the target tissue sufficient to activate or produce heat shock proteins in the cells of the target tissue without damaging the target tissue itself. In order to do so, typically, a pulsed source of ultrasound or electromagnetic radiation energy is provided and applied to the target tissue in a manner which raises the target tissue temperature, such as between 6° C. and 11° C., transiently while only 6° C. or 1° C. or less for the long term, such as over several minutes.

Figure 29:
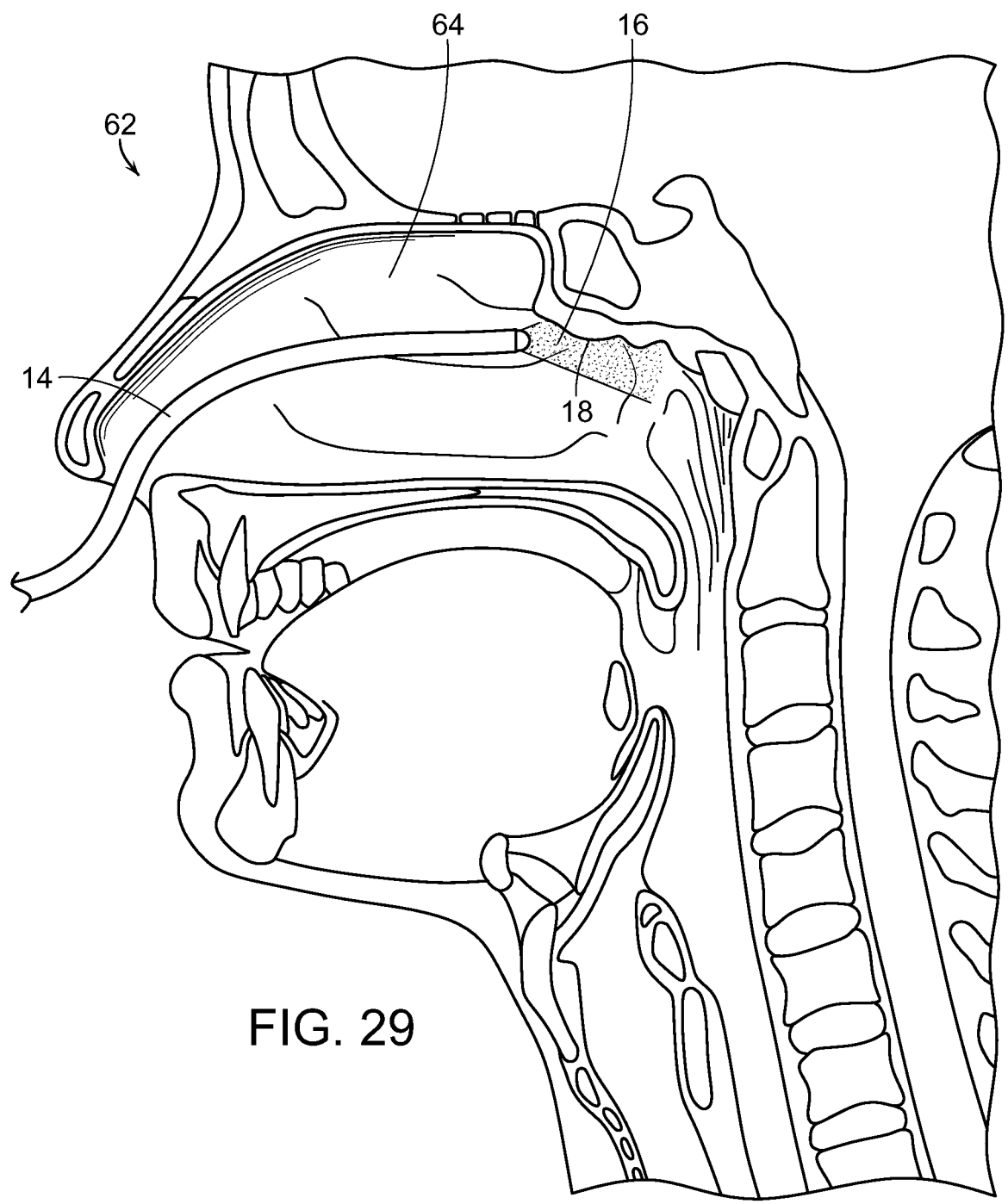
FIG. 29 is a cross-sectional and diagrammatic view of an end of an endoscope inserted into the nasal cavity and treating tissue therein, in accordance with the present invention.

It is believed that stimulating HSP production in accordance with the present invention can be effectively utilized in treating a wide array of tissue abnormalities, ailments, and even infections. For example, the viruses that cause colds primarily affect a small port of the respiratory epithelium in the nasal passages and nasopharynx. Similar to the retina, the respiratory epithelium is a thin and clear tissue. With reference to FIG. 29, a cross-sectional view of a human head 62 is shown with an endoscope 14 inserted into the nasal cavity 64 and energy 16, such as laser light or the like, being directed to tissue 18 to be treated within the nasal cavity 64. The tissue 18 to be treated could be within the nasal cavity 64, including the nasal passages, and nasopharynx.

To assure absorption of the laser energy, or other energy source, the wavelength can be adjusted to an infrared (IR) absorption peak of water, or an adjuvant dye can be used to serve as a photosensitizer. In such a case, treatment would then consist of drinking, or topically applying, the adjuvant, waiting a few minutes for the adjuvant to permeate the surface tissue, and then administering the laser light or other energy source 16 to the target tissue 18 for a few seconds, such as via optical fibers in an endoscope 14, as illustrated in FIG. 29. To provide comfort of the patient, the endoscope 14 could be inserted after application of a topical anesthetic. If necessary, the procedure could be repeated periodically, such as in a day or so.

The treatment would stimulate the activation or production of heat shock proteins and facilitate protein repair without damaging the cells and tissues being treated. As discussed above, certain heat shock proteins have been found to play an important role in the immune response as well as the well-being of the targeted cells and tissue. The source of energy could be monochromatic laser light, such as 810 nm wavelength laser light, administered in a manner similar to that described in the above-referenced patent applications, but administered through an endoscope or the like, as illustrated in FIG. 29. The adjuvant dye would be selected so as to increase the laser light absorption. While this comprises a particularly preferred method and embodiment of performing the invention, it will be appreciated that other types of energy and delivery means could be used to achieve the same objectives in accordance with the present invention.

Figure 30:
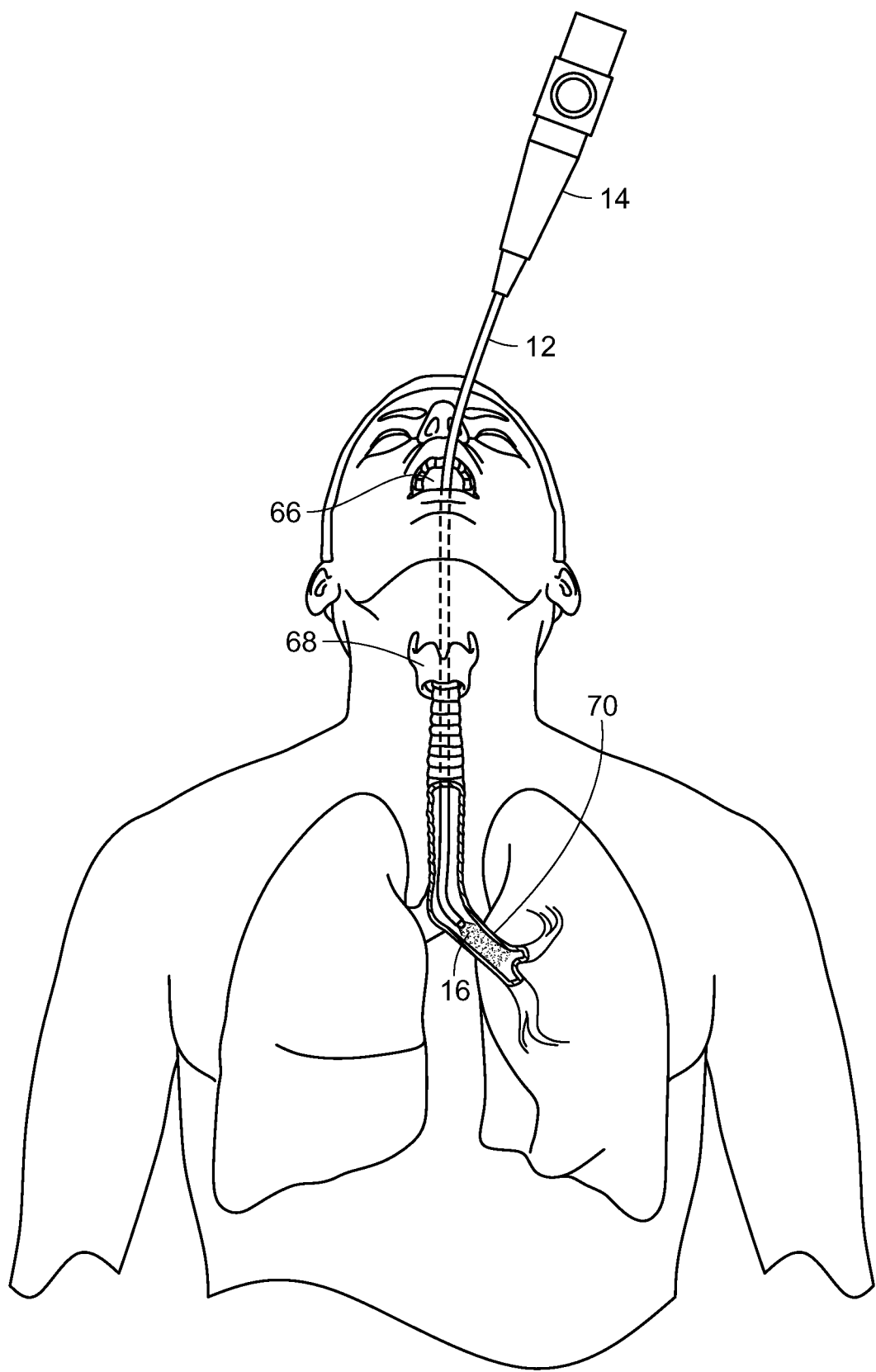
FIG. 30 is a diagrammatic and partially cross-sectioned view of a bronchoscope extending through the trachea and into the bronchus of a lung and providing treatment thereto, in accordance with the present invention.

With reference now to FIG. 30, a similar situation exists for the flu virus, where the primary target is the epithelium of the upper respiratory tree, in segments that have diameters greater than about 3.3 mm, namely, the upper six generations of the upper respiratory tree. A thin layer of mucous separates the targeted epithelial cells from the airway lumen, and it is in this layer that the antigen-antibody interactions occur that result in inactivation of the virus.

With continuing reference to FIG. 30, the flexible light tube 12 of a bronchoscope 14 is inserted through the individual's mouth 66 through the throat and trachea 68 and into a bronchus 70 of the respiratory tree. There the laser light or other energy source 16 is administered and delivered to the tissue in this area of the uppermost segments to treat the tissue and area in the same manner described above with respect to FIG. 29. It is contemplated that a wavelength of laser or other energy would be selected so as to match an IR absorption peak of the water resident in the mucous to heat the tissue and stimulate HSP activation or production and facilitate protein repair, with its attendant benefits.

Figure 31:
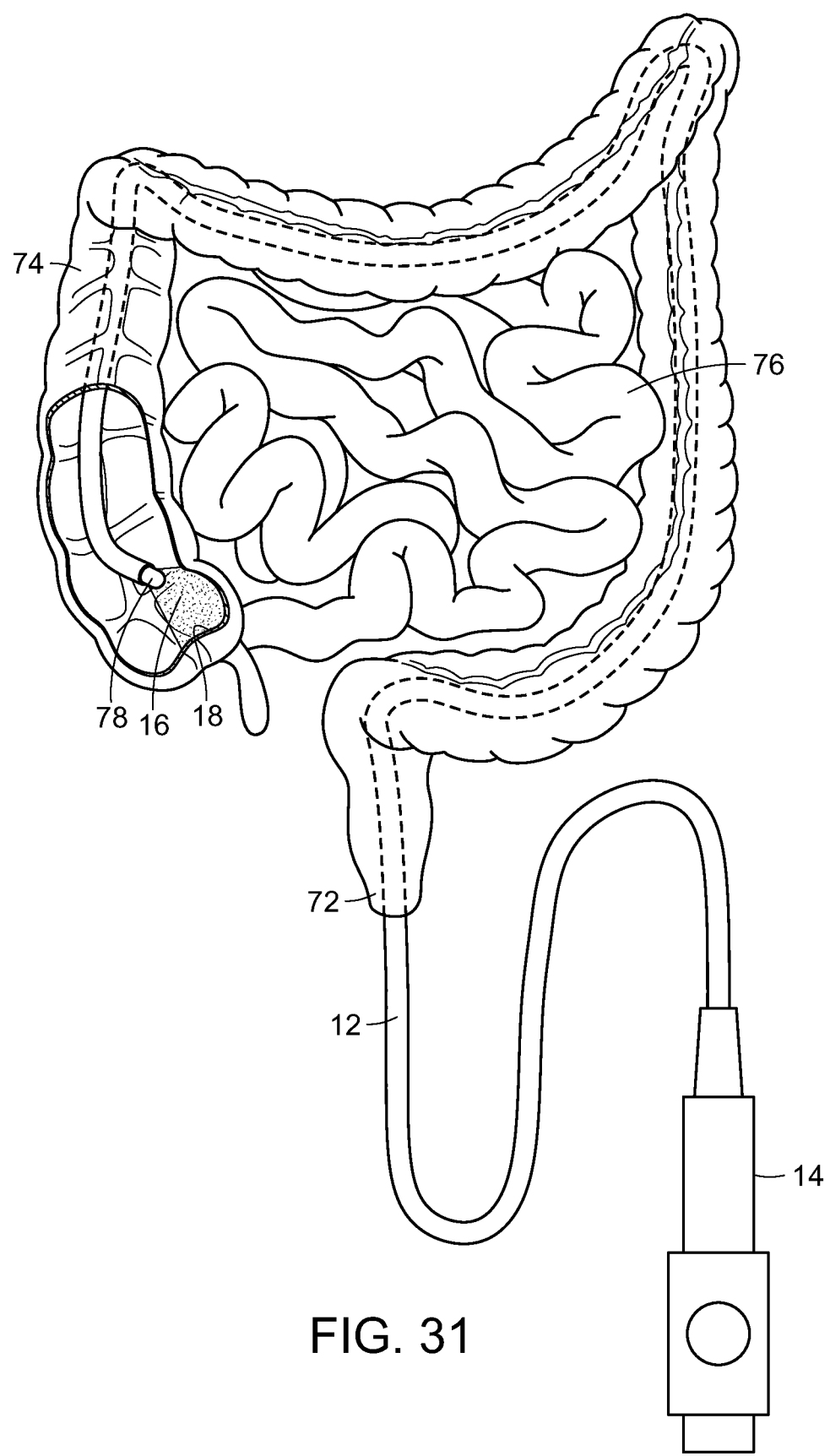
FIG. 31 is a diagrammatic view of a colonoscope providing photostimulation to an intestinal or colon area of the body, in accordance with the present invention.

With reference now to FIG. 31, a colonoscope 14 could have flexible optical tube 12 thereof inserted into the anus and rectum 72 and into either the large intestine 74 or small intestine 76 so as to deliver the selected laser light or other energy source 16 to the area and tissue to be treated, as illustrated. This could be used to assist in treating colon cancer as well as other gastrointestinal issues.

Typically, the procedure could be performed similar to a colonoscopy in that the bowel would be cleared of all stool, and the patient would lie on his/her side and the physician would insert the long, thin light tube portion 12 of the colonoscope 14 into the rectum and move it into the area of the colon, large intestine 74 or small intestine 76 to the area to be treated. The physician could view through a monitor the pathway of the inserted flexible member 12 and even view the tissue at the tip of the colonoscope 14 within the intestine, so as to view the area to be treated. Using one of the other fiber optic or light tubes, the tip 78 of the scope would be directed to the tissue to be treated and the source of laser light or other radiation 16 would be delivered through one of the light tubes of the colonoscope 14 to treat the area of tissue to be treated, as described above, in order to stimulate HSP activation or production in that tissue 18.

Figure 32:
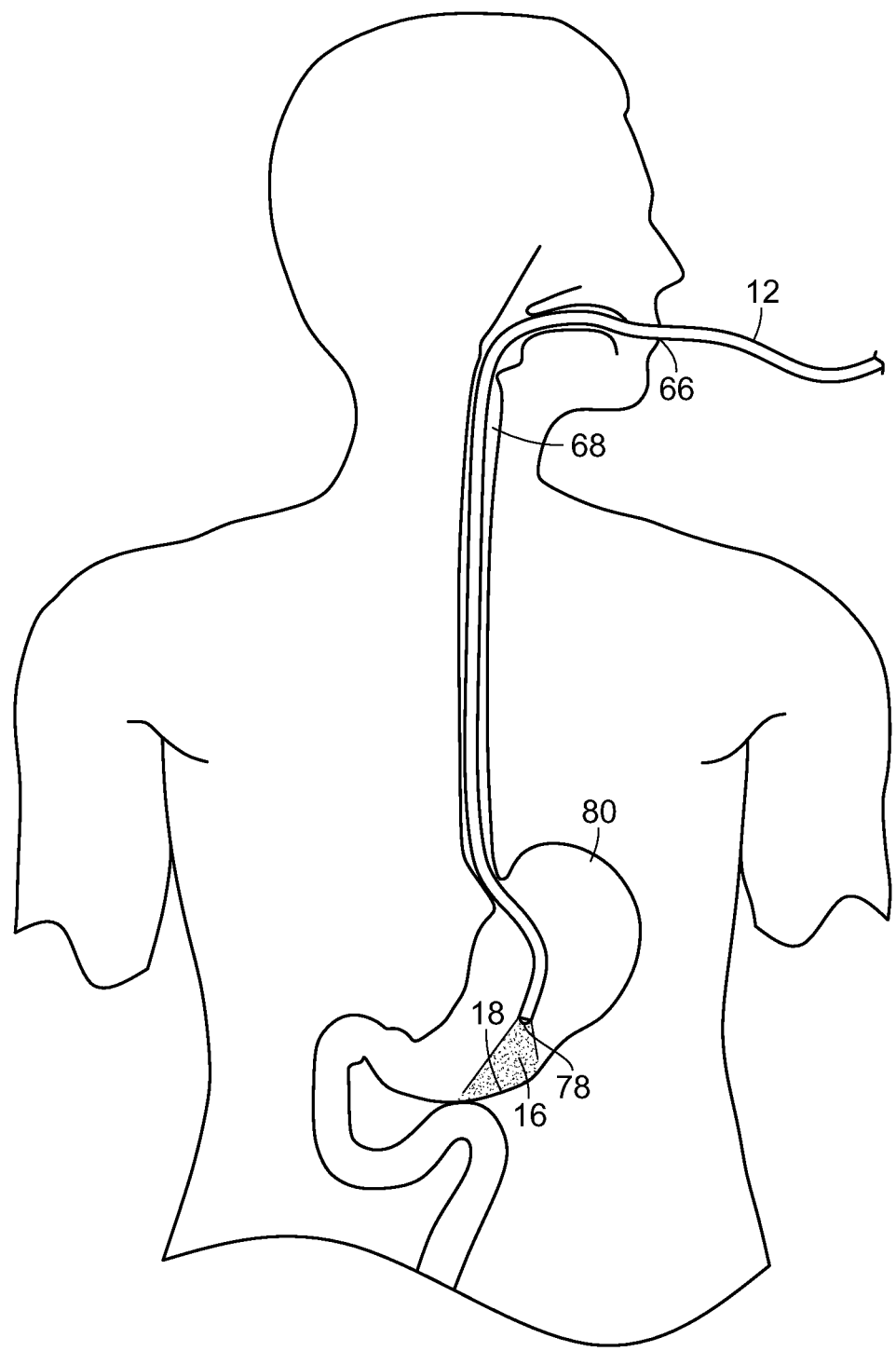
FIG. 32 is a diagrammatic view of an endoscope inserted into a stomach and providing treatment thereto, in accordance with the present invention.

With reference now to FIG. 32, another example in which the present invention can be advantageously used is what is frequently referred to as "leaky gut" syndrome, a condition of the gastrointestinal (GI) tract marked by inflammation and other metabolic dysfunction. Since the GI tract is susceptible to metabolic dysfunction similar to the retina, it is anticipated that it will respond well to the treatment of the present invention. This could be done by means of subthreshold, diode micropulse laser (SDM) treatment, as discussed above, or by other energy sources and means as discussed herein and known in the art.

With continuing reference to FIG. 32, the flexible light tube 12 of an endoscope or the like is inserted through the patient's mouth 66 through the throat and trachea area 68 and into the stomach 80, where the tip or end 78 thereof is directed towards the tissue 18 to be treated, and the laser light or other energy source 16 is directed to the tissue 18. It will be appreciated by those skilled in the art that a colonoscope could also be used and inserted through the rectum 72 and into the stomach 80 or any tissue between the stomach and the rectum.

If necessary, a chromophore pigment could be delivered to the GI tissue orally to enable absorption of the radiation. If, for instance, unfocused 810 nm radiation from a laser diode or LED were to be used, the pigment would have an absorption peak at or near 810 nm. Alternatively, the wavelength of the energy source could be adjusted to a slightly longer wavelength at an absorption peak of water, so that no externally applied chromophore would be required.

Figure 33:
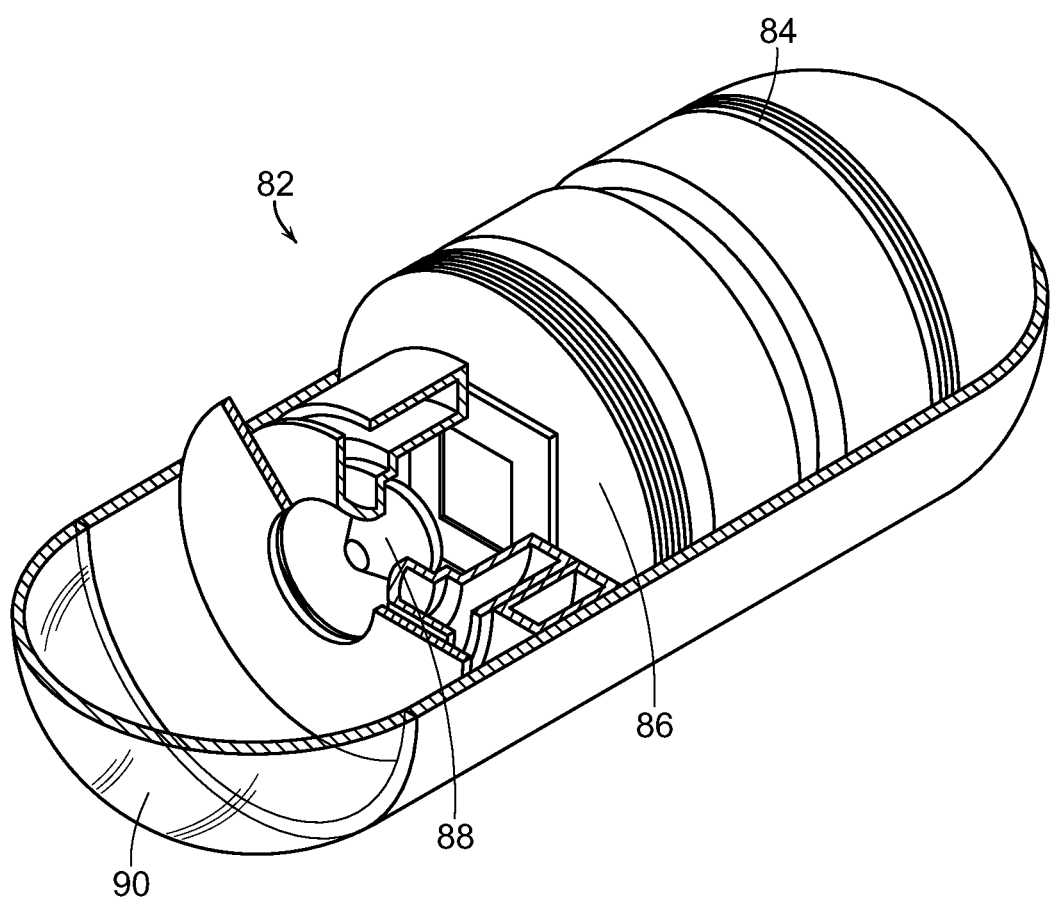
FIG. 33 is a partially sectioned perspective view of a capsule endoscope, used in accordance with the present invention.

It is also contemplated by the present invention that a capsule endoscope 82, such as that illustrated in FIG. 33, could be used to administer the radiation and energy source in accordance with the present invention. Such capsules are relatively small in size, such as approximately one inch in length, so as to be swallowed by the patient. As the capsule or pill 82 is swallowed and enters into the stomach and passes through the GI tract, when at the appropriate location, the capsule or pill 82 could receive power and signals, such as via antenna 84, so as to activate the source of energy 86, such as a laser diode and related circuitry, with an appropriate lens 88 focusing the generated laser light or radiation through a radiation-transparent cover 90 and onto the tissue to be treated. It will be understood that the location of the capsule endoscope 82 could be determined by a variety of means such as external imaging, signal tracking, or even by means of a miniature camera with lights through which the doctor would view images of the GI tract through which the pill or capsule 82 was passing through at the time. The capsule or pill 82 could be supplied with its own power source, such as by virtue of a battery, or could be powered externally via an antenna, such that the laser diode 86 or other energy generating source create the desired wavelength and pulsed energy source to treat the tissue and area to be treated.

As in the treatment of the retina in previous applications, the radiation would be pulsed to take advantage of the micropulse temperature spikes and associated safety, and the power could be adjusted so that the treatment would be completely harmless to the tissue. This could involve adjusting the peak power, pulse times, and repetition rate to give spike temperature rises on the order of 10° C., while maintaining the long term rise in temperature to be less than the FDA mandated limit of 1° C. If the pill form 82 of delivery is used, the device could be powered by a small rechargeable battery or over wireless inductive excitation or the like. The heated/stressed tissue would stimulate activation or production of HSP and facilitate protein repair, and the attendant benefits thereof.

From the foregoing examples, the technique of the present invention is limited to the treatment of conditions at near body surfaces or at internal surfaces easily accessible by means of fiber optics or other optical delivery means. The reason that the application of SDM to activate HSP activity is limited to near surface or optically accessibly regions of the body is that the absorption length of IR or visible radiation in the body is very short. However, there are conditions deeper within tissue or the body which could benefit from the present invention. Thus, the present invention contemplates the use of ultrasound and/or radio frequency (RF) and even shorter wavelength electromagnetic (EM) radiation such as microwave which have relatively long absorption lengths in body tissue. The use of pulsed ultrasound is preferable to RF electromagnetic radiation to activate remedial HSP activity in abnormal tissue that is inaccessible to surface SDM or the like.

For deep tissue that is not near an internal orifice, a light pipe may not be an effective means of delivering the pulsed energy. In that case, pulsed low frequency electromagnetic energy or preferably pulsed ultrasound can be used to cause a series of temperature spikes in the target tissue.

Thus, in accordance with the present invention, a source of pulsed ultrasound or electromagnetic radiation is applied to the target tissue in order to stimulate HSP production or activation and to facilitate protein repair in the living animal tissue. In general, electromagnetic radiation may be ultraviolet waves, microwaves, other radiofrequency waves, laser light at predetermined wavelengths, etc. On the other hand, if electromagnetic energy is to be used for deep tissue targets away from natural orifices, absorption lengths restrict the wavelengths to those of microwaves or radiofrequency waves, depending on the depth of the target tissue. However, ultrasound is to be preferred to long wavelength electromagnetic radiation for deep tissue targets away from natural orifices.

The ultrasound or electromagnetic radiation is pulsed so as to create a thermal time-course in the tissue that stimulates HSP production or activation and facilitates protein repair without causing damage to the cells and tissue being treated. The area and/or volume of the treated tissue is also controlled and minimized so that the temperature spikes are on the order of several degrees, e.g. approximately 10° C., while maintaining the long-term rise in temperature to be less than the FDA mandated limit, such as 1° C. It has been found that if too large of an area or volume of tissue is treated, the increased temperature of the tissue cannot be diffused sufficiently quickly enough to meet the FDA requirements. However, limiting the area and/or volume of the treated tissue as well as creating a pulsed source of energy accomplishes the goals of the present invention of stimulating HSP activation or production by heating or otherwise stressing the cells and tissue, while allowing the treated cells and tissues to dissipate any excess heat generated to within acceptable limits.

Figure 34:
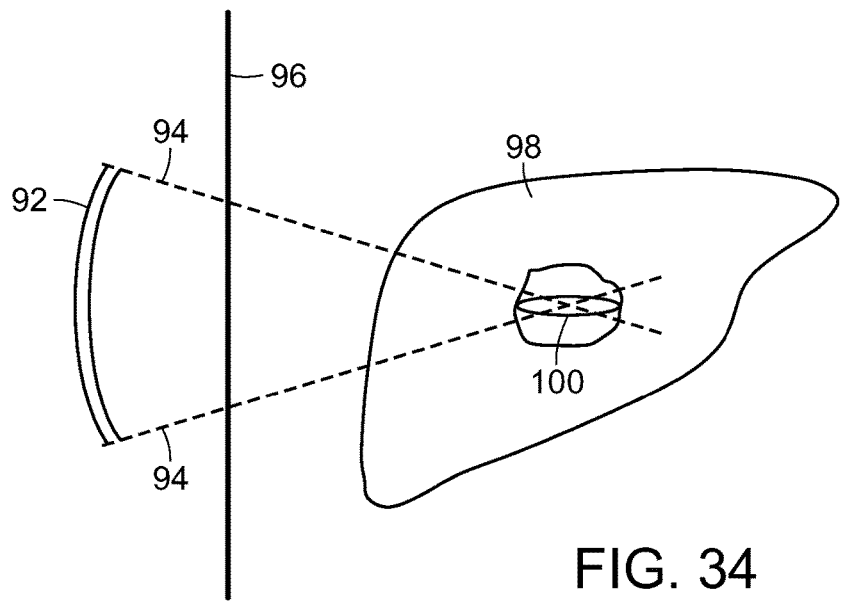
FIG. 34 is a diagrammatic view of a pulsed high intensity focused ultrasound for treating tissue internal the body, in accordance with the present invention.

With reference now to FIG. 34, with ultrasound, a specific region deep in the body can be specifically targeted by using one or more beams that are each focused on the target site. The pulsating heating will then be largely only in the targeted region where the beams are focused and overlap. Pulsed ultrasound sources can also be used for abnormalities at or near surfaces as well.

As illustrated in FIG. 34, an ultrasound transducer 92 or the like generates a plurality of ultrasound beams 94 which are coupled to the skin via an acoustic-impedance-matching gel, and penetrate through the skin 96 and through undamaged tissue in front of the focus of the beams 94 to a target organ 98, such as the illustrated liver, and specifically to a target tissue 100 to be treated where the ultrasound beams 94 are focused. As mentioned above, the pulsating heating will then only be at the targeted, focused region 100 where the focused beams 94 overlap. The tissue in front of and behind the focused region 100 will not be heated or affected appreciably.

The present invention contemplates not only the treatment of surface or near surface tissue, such as using the laser light or the like, deep tissue using, for example, focused ultrasound beams or the like, but also treatment of blood diseases, such as sepsis. As indicated above, focused ultrasound treatment could be used both at surface as well as deep body tissue, and could also be applied in this case in treating blood. However, it is also contemplated that the SDM and similar treatment options which are typically limited to surface or near surface treatment of epithelial cells and the like be used in treating blood diseases at areas where the blood is accessible through a relatively thin layer of tissue, such as the earlobe.

Figure 35:
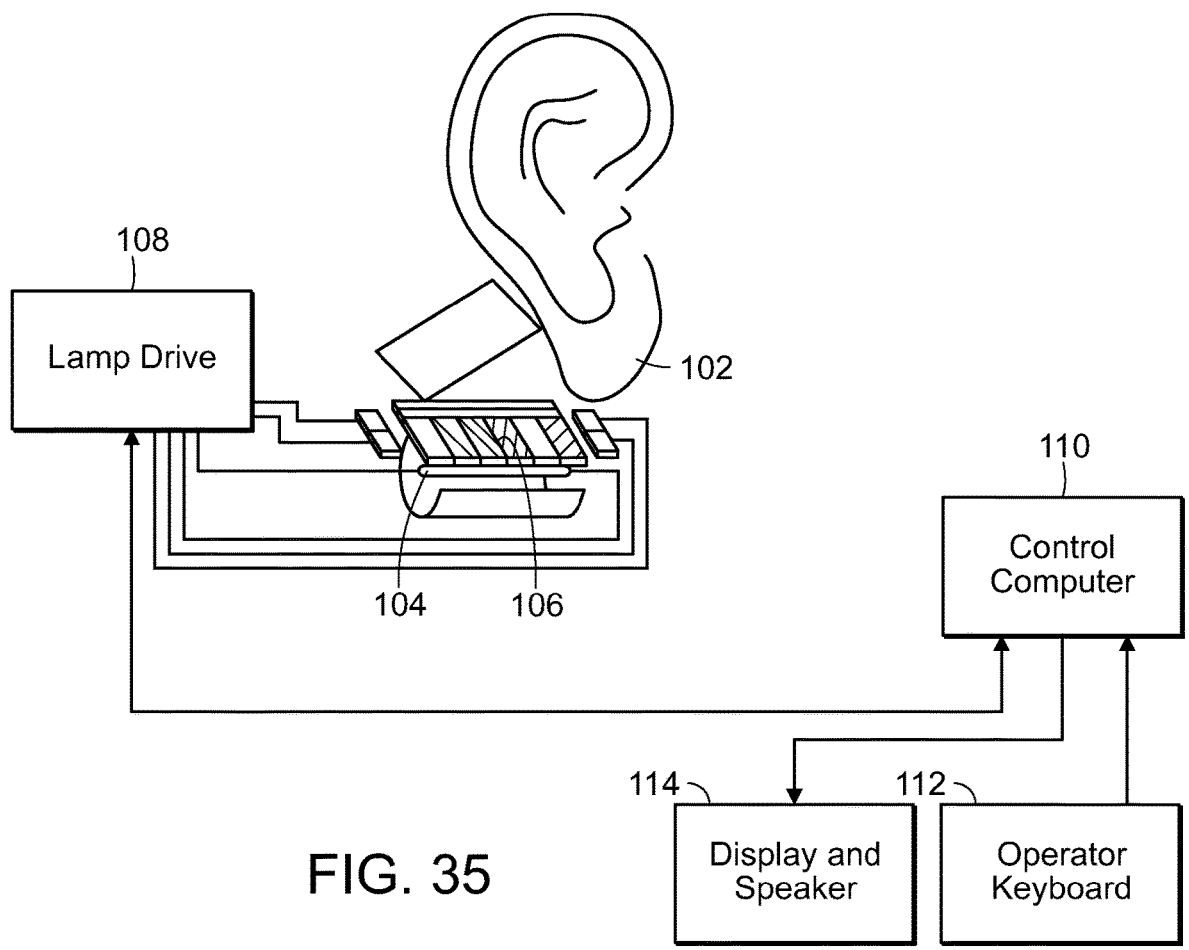
FIG. 35 is a diagrammatic view for delivering therapy to the bloodstream of a patient, through an earlobe, in accordance with the present invention.
Figure 36:
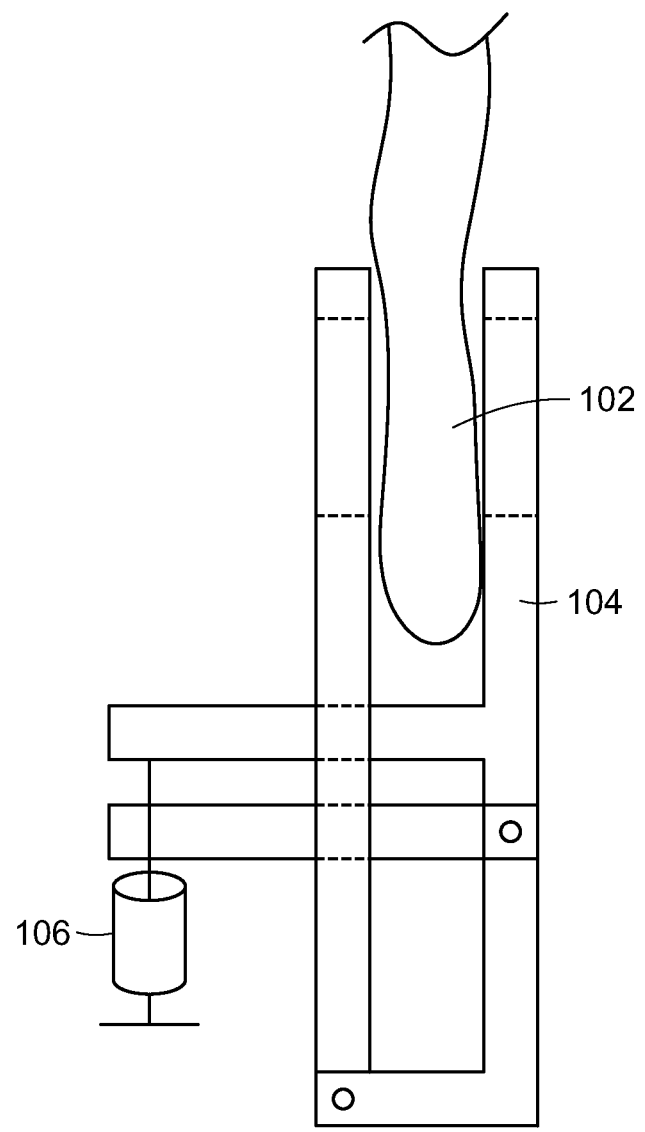
FIG. 36 is a cross-sectional view of a stimulating therapy device of the present invention used in delivering photostimulation to the blood, via an earlobe, in accordance with the present invention.

With reference now to FIGS. 35 and 36, treatment of blood disorders simply requires the transmission of SDM or other electromagnetic radiation or ultrasound pulses to the earlobe 102, where the SDM or other radiation source of energy could pass through the earlobe tissue and into the blood which passes through the earlobe. It would be appreciated that this approach could also take place at other areas of the body where the blood flow is relatively high and/or near the tissue surface, such as fingertips, inside of the mouth or throat, etc.

With reference again to FIGS. 35 and 36, an earlobe 102 is shown adjacent to a clamp device 104 configured to transmit SDM radiation or the like. This could be, for example, by means of one or more laser diodes 106 which would transmit the desired frequency at the desired pulse and pulse train to the earlobe 102. Power could be provided, for example, by means of a lamp drive 108. Alternatively, the lamp drive 108 could be the actual source of laser light, which would be transmitted through the appropriate optics and electronics to the earlobe 102. The clamp device 104 would merely be used to clamp onto the patient's earlobe and cause that the radiation be constrained to the patient's earlobe 102. This may be by means of mirrors, reflectors, diffusers, etc. This could be controlled by a control computer 110, which would be operated by a keyboard 112 or the like. The system may also include a display and speakers 114, if needed, for example if the procedure were to be performed by an operator at a distance from the patient.

The proposed treatment with a train of electromagnetic or ultrasound pulses has two major advantages over earlier treatments that incorporate a single short or sustained (long) pulse. First, the short (preferably subsecond) individual pulses in the train activate cellular reset mechanisms like HSP activation with larger reaction rate constants than those operating at longer (minute or hour) time scales. Secondly, the repeated pulses in the treatment provide large thermal spikes (on the order of 10,000) that allow the cell's repair system to more rapidly surmount the activation energy barrier that separates a dysfunctional cellular state from the desired functional state. The net result is a "lowered therapeutic threshold" in the sense that a lower applied average power and total applied energy can be used to achieve the desired treatment goal.

Power limitations in current micropulsed diode lasers require fairly long exposure duration. The longer the exposure, the more important the center-spot heat dissipating ability toward the unexposed tissue at the margins of the laser spot. Thus, the micropulsed laser light beam of an 810 nm diode laser should have an exposure envelope duration of 500 milliseconds or less, and preferably approximately 300 milliseconds. Of course, if micropulsed diode lasers become more powerful, the exposure duration should be lessened accordingly.

Aside from power limitations, another parameter of the present invention is the duty cycle, or the frequency of the train of micropulses, or the length of the thermal relaxation time between consecutive pulses. It has been found that the use of a 10% duty cycle or higher adjusted to deliver micropulsed laser at similar irradiance at similar MPE levels significantly increase the risk of lethal cell injury. However, duty cycles of less than 10%, and preferably 5% or less demonstrate adequate thermal rise and treatment at the level of the MPE cell to stimulate a biological response, but remain below the level expected to produce lethal cell injury. The lower the duty cycle, however, the exposure envelope duration increases, and in some instances can exceed 500 milliseconds.

Each micropulse lasts a fraction of a millisecond, typically between 50 microseconds to 100 microseconds in duration. Thus, for the exposure envelope duration of 300-500 milliseconds, and at a duty cycle of less than 5%, there is a significant amount of wasted time between micropulses to allow the thermal relaxation time between consecutive pulses. Typically, a delay of between 1 and 3 milliseconds, and preferably approximately 2 milliseconds, of thermal relaxation time is needed between consecutive pulses. For adequate treatment, the cells are typically exposed or hit between 50-200 times, and preferably between 75-150 at each location, and with the 1-3 milliseconds of relaxation or interval time, the total time in accordance with the embodiments described above to treat a given area which is being exposed to the laser spots is usually less than one second, such as between 100 milliseconds and 600 milliseconds on average. The thermal relaxation time is required so as not to overheat the cells within that location or spot and so as to prevent the cells from being damaged or destroyed. While time periods of 100-600 milliseconds do not seem long, given the small size of the laser spots and the need to treat a relatively large area of the target tissue, treating the entire target tissue take a significant amount of time, particularly for a patient who is undergoing treatment.

Other pulsed energy sources, including microwave, radio frequency and ultrasound is also preferably pulsed in nature and have duty cycles and/or pulse trains and thus lag time or intervals between micropulse energy applications to the target tissue. Moreover, the target tissue previously treated with the micropulse of the energy must be allowed to dissipate the heat created by the energy application in order not to exceed a predetermined upper temperature level which could permanently damage or even destroy the cells of the target tissue. Typically, the area or volume of target tissue to be treated is much larger than the area or volume of target tissue which is treated at any given moment by the energy sources, even if multiple beams of energy are created and applied to the target tissue.

Accordingly, the present invention may utilize the interval between consecutive applications to the same location to apply energy to a second treatment area, or additional areas, of the target tissue that is spaced apart from the first treatment area. The pulsed energy is returned to the first treatment location, or previous treatment locations, within the predetermined interval of time so as to provide sufficient thermal relaxation time between consecutive pulses, yet also sufficiently treat the cells in those locations or areas properly by sufficiently increasing the temperature of those cells over time by repeatedly applying the energy to that location in order to achieve the desired therapeutic benefits of the invention.

It is important to return to a previously treated location within a predetermined amount of time to allow the area to cool down sufficiently during that time, but also to treat it within the necessary window of time. In the case of the laser light pulsed energy applications, the laser light is returned to the previously treated location within one to three milliseconds, and preferably approximately two milliseconds, as one cannot wait one or two seconds and then return to a previously treated area that has not yet received the full treatment necessary, as the treatment will not be as effective or perhaps not effective at all. However, during that interval of time, typically approximately 2 milliseconds, at least one other area, and typically multiple areas, can be treated with a laser light application as the laser light pulses are typically 50 seconds to 100 microseconds in duration. This is referred to herein as microshifting. The number of additional areas which can be treated is limited only by the micopulse duration and the ability to controllably move the light beams from one area to another.

Currently, approximately four additional areas which are sufficiently spaced apart from one another can be treated during the thermal relaxation intervals beginning with a first treatment area when using laser light. Thus, multiple areas can be treated, at least partially, during the 200-500 millisecond exposure envelope for the first area. Thus, in a single interval of time, instead of only 100 simultaneous light spots being applied to a treatment area, approximately 500 light spots can be applied during that interval of time in different treatment areas. This would be the case, for example, for a laser light beam having a wavelength of 810 nm. For shorter wavelengths, such as 572 nm, even a greater number of individual locations can be exposed to the laser beams to create light spots. Thus, instead of a maximum of approximately 400 simultaneous spots, approximately 2,000 spots could be covered during the interval between micropulse treatments to a given area or location. Typically each location has between 50-200, and more typically between 75-150, light applications applied thereto over the course of the exposure envelope duration (typically 200-500 milliseconds) to achieve the desired treatment. In accordance with an embodiment of the present invention, the laser light would be reapplied to previously treated areas in sequence during the relaxation time intervals for each area or location. This would occur repeatedly until a predetermined number of laser light applications to each area to be treated have been achieved.

Similarly, the one or more beams of microwave, radiofrequency and/or ultrasound could be applied to second, or additional treatment areas of the target tissue that is spaced apart from the first treatment area, and after a predetermined interval of time returning, if necessary, to the first treatment area of the target tissue to reapply the pulsed energy thereto. The pulsed energy could be reapplied to a previously treated area in sequence during the relaxation time intervals for each area or location until a desired number of applications has been achieved to each treatment area. The treatment areas must be separated by at least a predetermined minimum distance to enable thermal relaxation and dissipation and avoid thermal tissue damage. The pulsed energy parameters including wavelength or frequency, duty cycle and pulse train duration are selected so as to raise the target tissue temperature up to 11° C., such as between approximately 6°–11° C., during application of the pulsed energy source to the target tissue to achieve a therapeutic effect, such as by stimulating HSP production within the cells. However, the cells of the target tissue must be given a period of time to dissipate the heat such that the average temperature rise of the tissue over several minutes is maintained at or below a predetermined level, such as 6° C. or less, or even 1° C. or less, over several minutes so as not to permanently damage the target tissue.

Figure 37A:
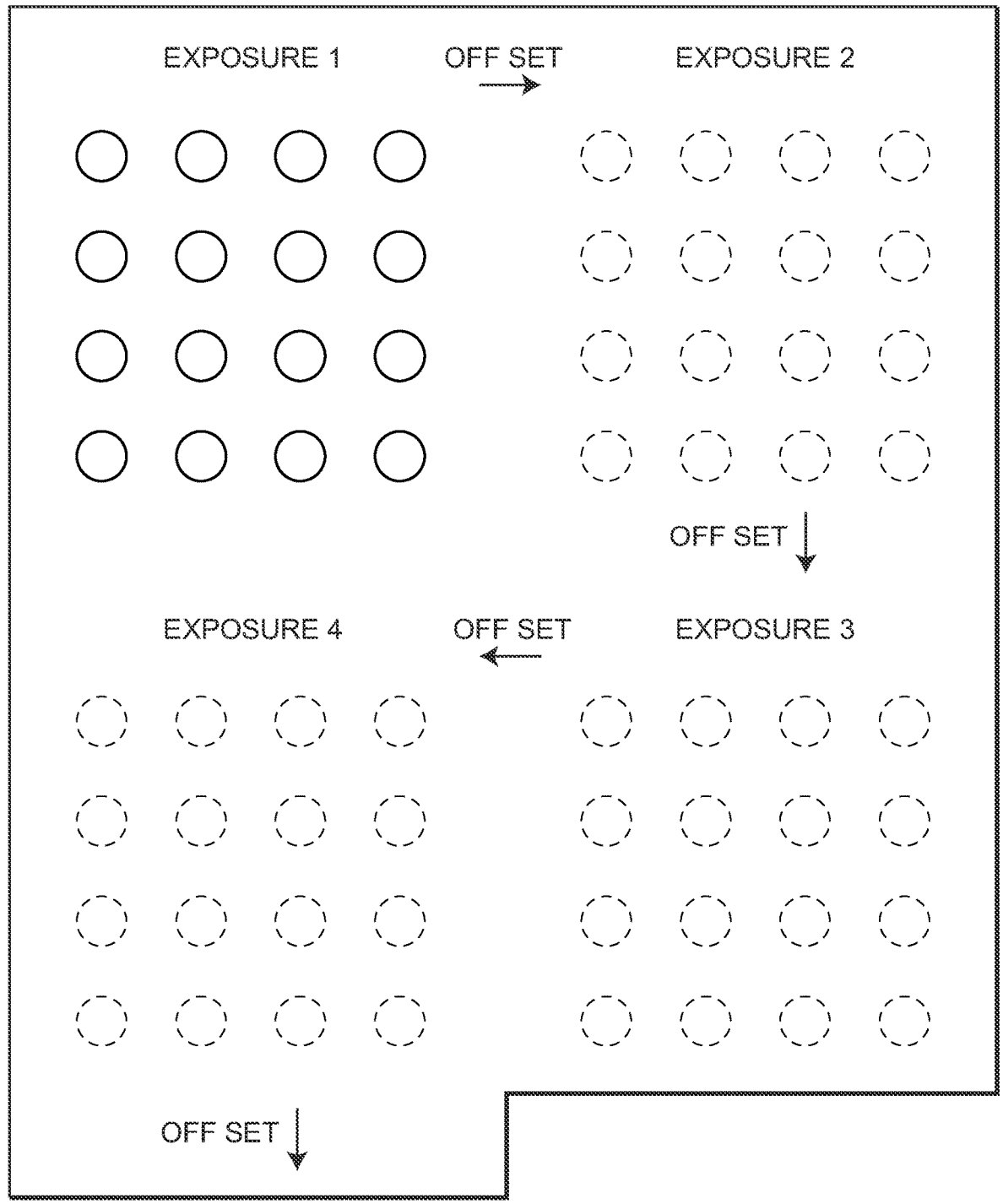
FIGS. 37A-37D are diagrammatic views illustrated in the application of micropulsed energy to different treatment areas during a predetermined interval of time, within a single treatment session, and reapplying the energy to previously treated areas, in accordance with the present invention.
Figure 37B:
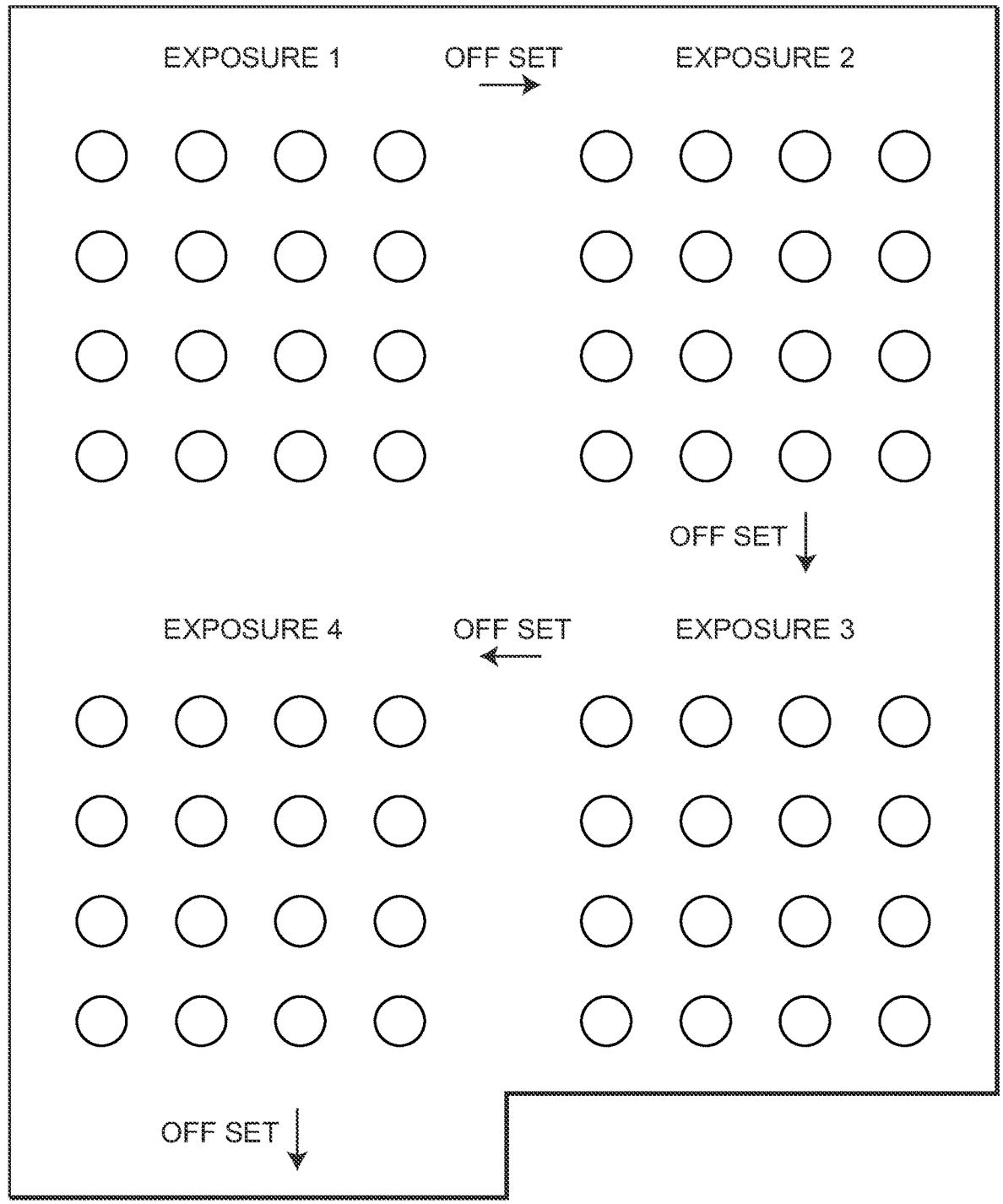
Figure 37C:
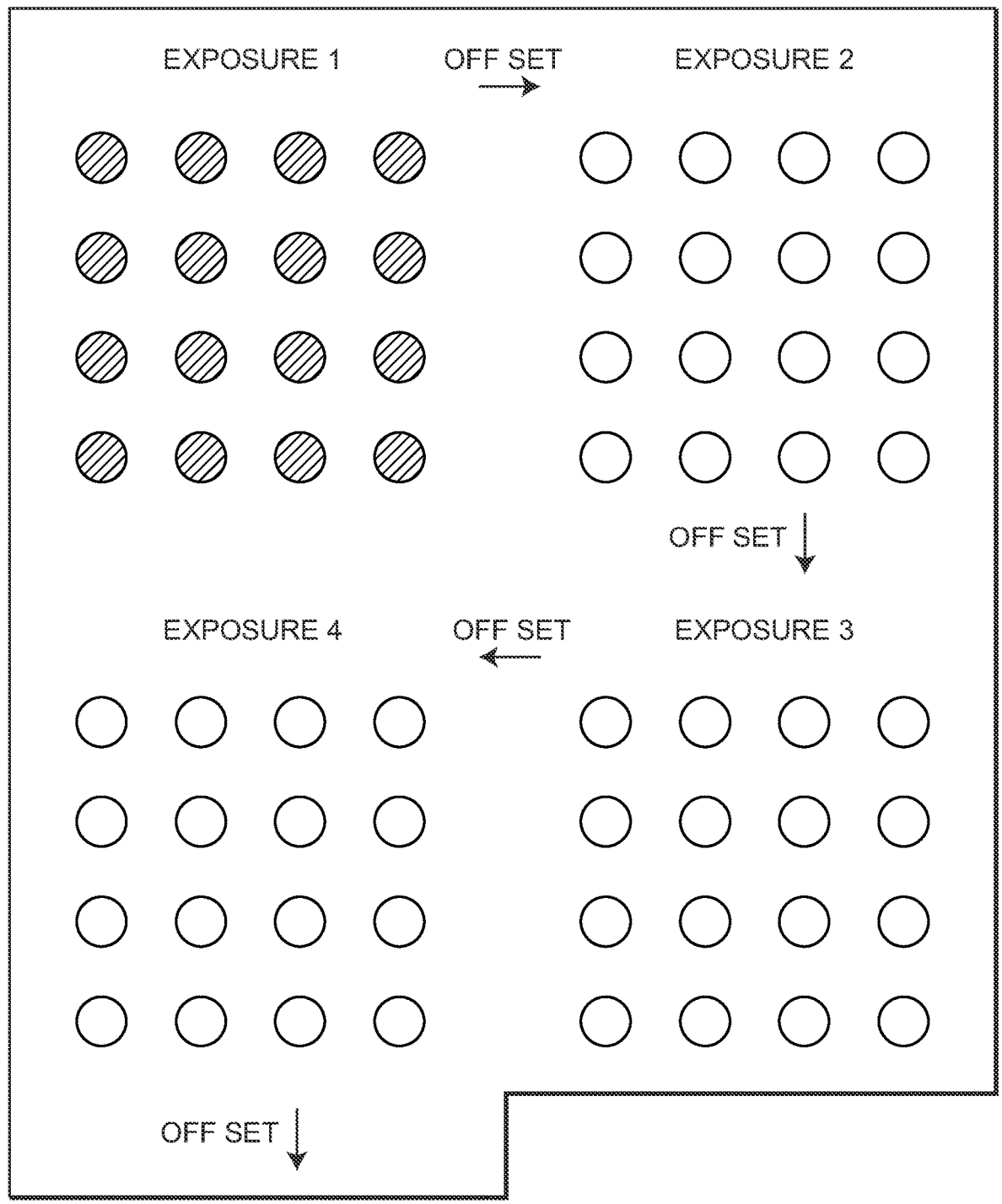
Figure 37D:
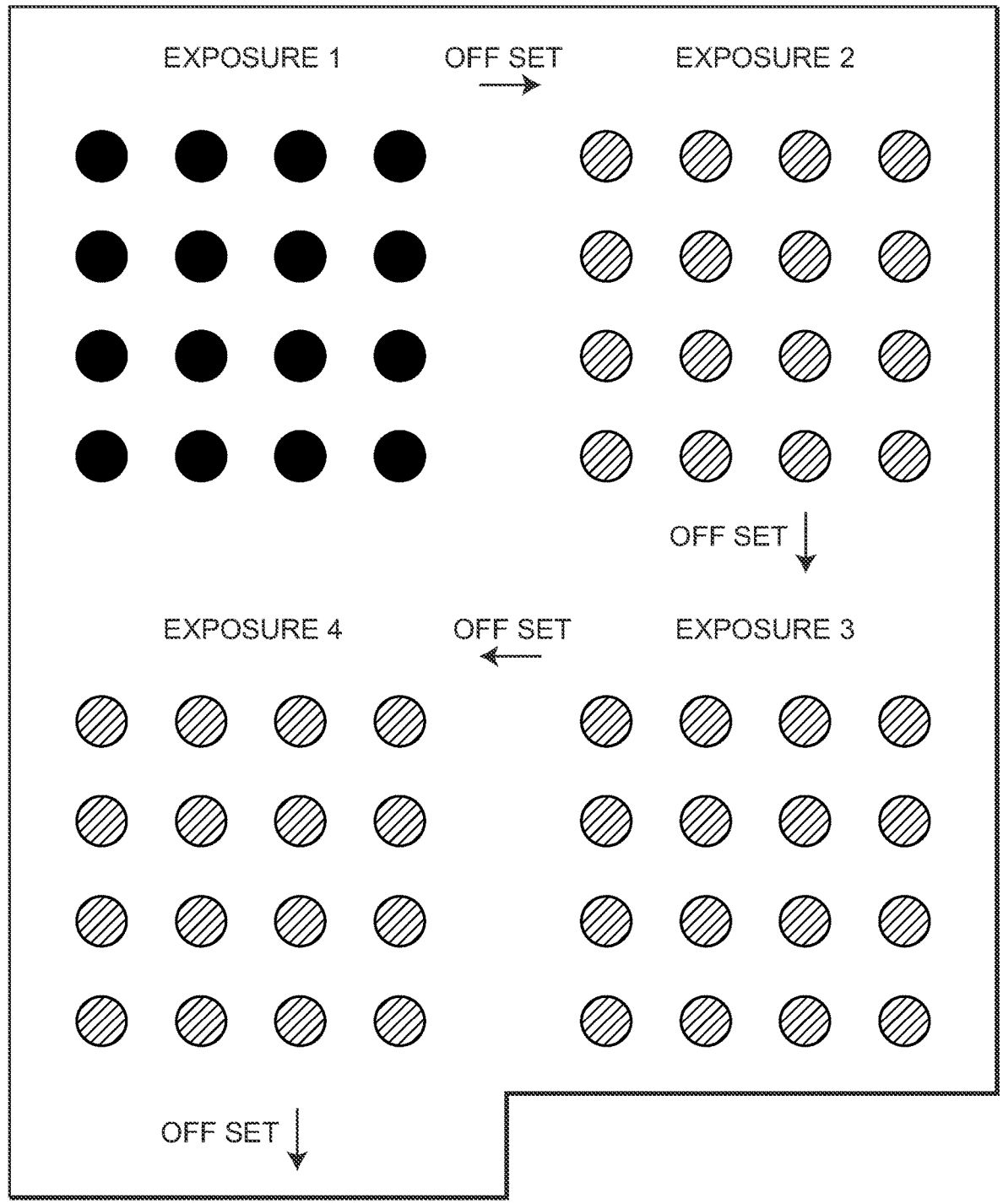

This is diagrammatically illustrated in FIGS. 37A-37D. FIG. 37A illustrates with solid circles a first area having energy beams, such as laser light beams, applied thereto as a first application. The beams are controllably offset or microshifted to a second exposure area, followed by a third exposure area and a fourth exposure area, as illustrated in FIG. 37B, until the locations in the first exposure area need to be re-treated by having beams applied thereto again within the thermal relaxation time interval. The locations within the first exposure area would then have energy beams reapplied thereto, as illustrated in FIG. 37C. Secondary or subsequent exposures would occur in each exposure area, as illustrated in FIG. 37D by the increasingly shaded dots or circles until the desired number of exposures or hits or applications of energy to the target tissue area has been achieved to therapeutically treat these areas, diagrammatically illustrated by the blackened circles in exposure area 1 in FIG. 37D. When a first or previous exposure area has been completed treated, this enables the system to add an additional exposure area, which process is repeated until the entire area to be treated has been fully treated. It should be understood that the use of solid circles, broken line circles, partially shaded circles, and fully shaded circles are for explanatory purposes only, as in fact the exposure of the energy or laser light in accordance with the present invention is invisible and non-detectable to both the human eye as well as known detection devices and techniques, including ophthalmoscopically and angiographically.

Adjacent exposure areas must be separated by at least a predetermined minimum distance to avoid thermal tissue damage. Such distance is at least 0.5 diameter away from the immediately preceding treated location or area, and more preferably between 1-2 diameters away. Such spacing relates to the actually treated locations in a previous exposure area. It is contemplated by the present invention that a relatively large area may actually include multiple exposure areas therein which are offset in a different manner than that illustrated in FIG. 37. For example, the exposure areas could comprise the thin lines illustrated in FIGS. 25 and 26, which would be repeatedly exposed in sequence until all of the necessary areas were fully exposed and treated. In accordance with the present invention, the time required to treat that area to be treated is significantly reduced, such as by a factor of 4 or 5 times, such that a single treatment session takes much less time for the medical provider and the patient need not be in discomfort for as long of a period of time.

Figure 38:
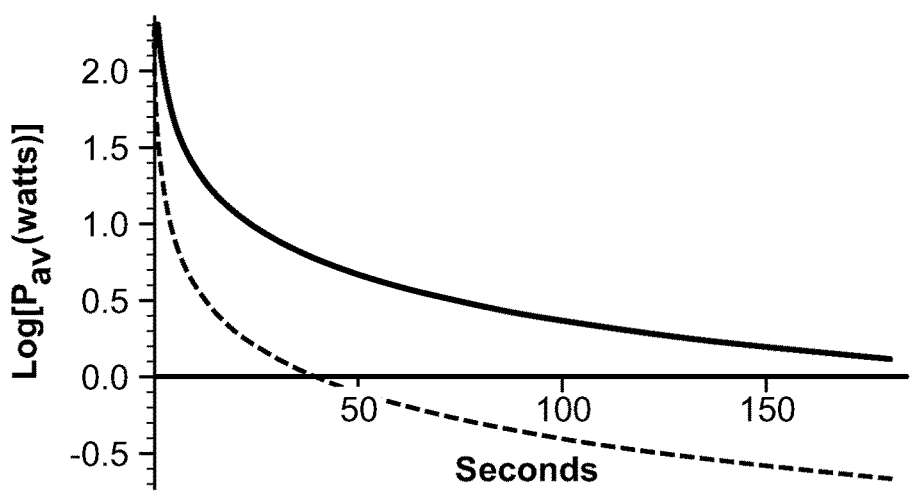
FIGS. 38-40 are graphs depicting the relationship of treatment power and time in accordance with the embodiments of the present invention.
Figure 39:
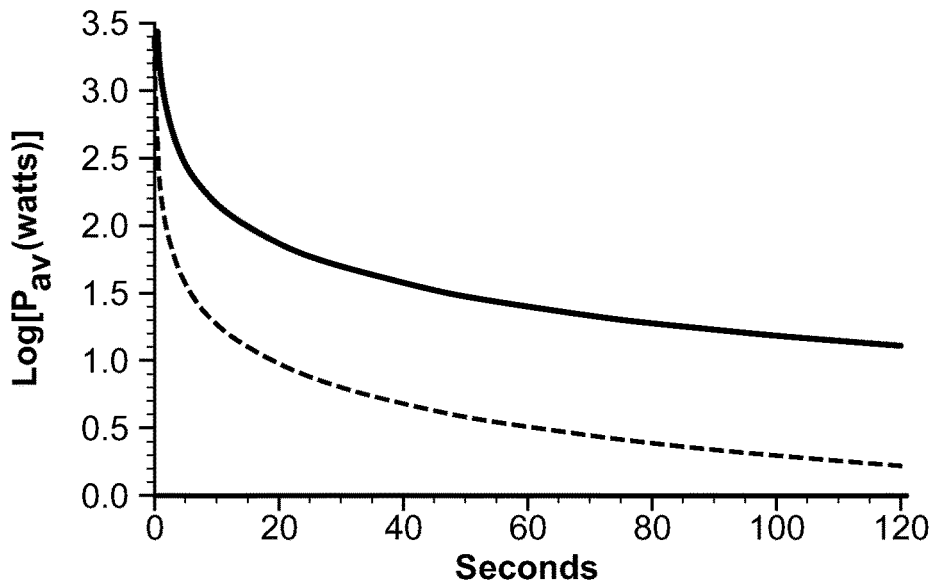
Figure 40:
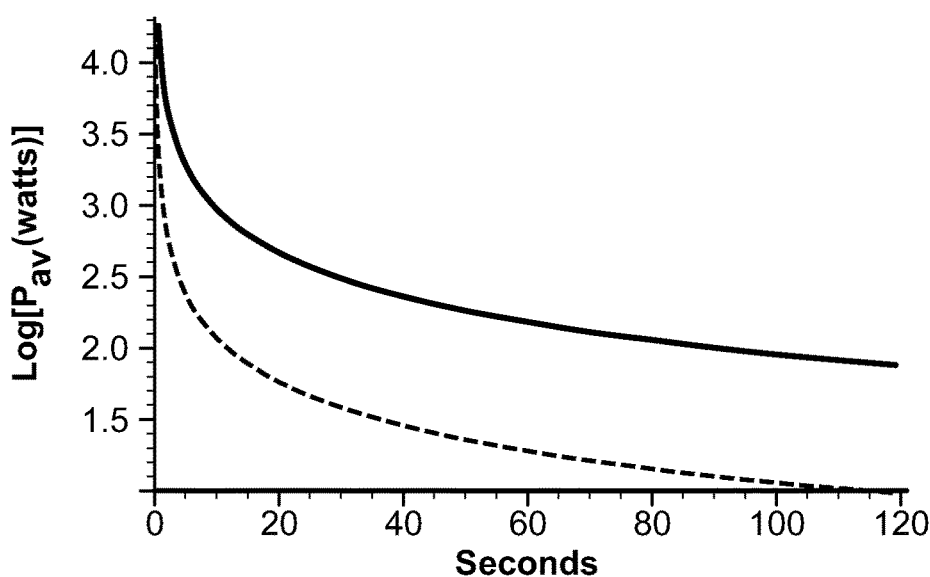

In accordance with this embodiment of the invention of applying one or more treatment beams at once, and moving the treatment beams to a series of new locations, then bringing the beams back to re-treat the same location or area repeatedly has been found to also require less power compared to the methodology of keeping the beams in the same locations or area during the entire exposure envelope duration. With reference to FIGS. 38-40, there is a linear relationship between the pulse length and the power necessary, but there is a logarithmic relationship between the heat generated.

With reference to FIG. 38, a graph is provided wherein the x-axis represents the Log of the average power in watts of a laser and the y-axis represents the treatment time, in seconds. The lower curve is for panmacular treatment and the upper curve is for panretinal treatment. This would be for a laser light beam having a micropulse time of 50 microseconds, a period of 2 milliseconds of time between pulses, and duration of train on a spot of 300 milliseconds. The areas of each retinal spot are 100 microns, and the laser power for these 100 micron retinal spots is 0.74 watts. The panmacular area is $0.55^2$, requiring 7,000 panmacular spots total, and the panretinal area is $3.30^2$, requiring 42,000 laser spots for full coverage. Each RPE spot requires a minimum energy in order for its reset mechanism to be adequately activated, in accordance with the present invention, namely, 38.85 joules for panmacular and 233.1 joules for panretinal. As would be expected, the shorter the treatment time, the larger the required average power. However, there is an upper limit on the allowable average power, which limits how short the treatment time can be.

As mentioned above, there are not only power constraints with respect to the laser light available and used, but also the amount of power that can be applied to the eye without damaging eye tissue. For example, temperature rise in the lens of the eye is limited, such as between 4° C. so as not to overheat and damage the lens, such as causing cataracts. Thus, an average power of 7.52 watts could elevate the lens temperature to approximately 4° C. This limitation in power increases the minimum treatment time.

However, with reference to FIG. 39, the total power per pulse required is less in the microshift case of repeatedly and sequentially moving the laser spots and returning to prior treated locations, so that the total energy delivered and the total average power during the treatment time is the same. FIGS. 39 and 40 show how the total power depends on treatment time. This is displayed in FIG. 39 for panmacular treatment, and in FIG. 40 for panretinal treatment. The upper, solid line or curve represents the embodiment where there are no microshifts taking advantage of the thermal relaxation time interval, such as described and illustrated in FIG. 24, whereas the lower dashed line represents the situation for such microshifts, as described and illustrated in FIG. 37. FIGS. 39 and 40 show that for a given treatment time, the peak total power is less with microshifts than without microshifts. This means that less power is required for a given treatment time using the microshifting embodiment of the present invention. Alternatively, the allowable peak power can be advantageously used, reducing the overall treatment time.

Thus, in accordance with FIGS. 38-40, a log power of 1.0 (10 watts) would require a total treatment time of 20 seconds using the microshifting embodiment of the present invention, as described herein. It would take more than 2 minutes of time without the microshifts, and instead leaving the micropulsed light beams in the same location or area during the entire treatment envelope duration. There is a minimum treatment time according to the wattage. However, this treatment time with microshifting is much less than without microshifting. As the laser power required is much less with the microshifting, it is possible to increase the power in some instances in order to reduce the treatment time for a given desired retinal treatment area. The product of the treatment time and the average power is fixed for a given treatment area in order to achieve the therapeutic treatment in accordance with the present invention. This could be implemented, for example, by applying a higher number of therapeutic laser light beams or spots simultaneously at a reduced power. Of course, since the parameters of the laser light are selected to be therapeutically effective yet not destructive or permanently damaging to the cells, no guidance or tracking beams are required, only the treatment beams as all areas can be treated in accordance with the present invention.

Although the present invention is described for use in connection with a micropulsed laser, theoretically a continuous wave laser could potentially be used instead of a micropulsed laser. However, with the continuous wave laser, there is concern of overheating as the laser is moved from location to location in that the laser does not stop and there could be heat leakage and overheating between treatment areas. Thus, while it is theoretically possible to use a continuous wave laser, in practice it is not ideal and the micropulsed laser is preferred.

While the information provided in connection with graphs 38-40 is derived from observations and calculations of laser light beams as the energy source applied to retinal eye tissue, it is believed that applying such pulsed light beams to other tissue will achieve similar results in that moving the treatment beams to a series of new locations, then bringing the beams back to re-treat the same location or area repeatedly will not only save time but also require less power compared to the methodology of keeping the beams in the same location or area during the entire exposure envelope duration. Similarly, it is believed that such power conservation will also be achieved with other sources of pulsed energy, including coherent and non-coherent light, microwave, radiofrequency and ultrasound energy sources.

In accordance with the microshifting technique described above, the shifting or steering of the pattern of light beams may be done by use of an optical scanning mechanism, such as that illustrated and described in connection with FIGS. 22 and 23. For situations where the wavelength of the illumination or energy is much less than the distance to the volume to be illuminated or exposed, the steering can be accomplished by using phased arrays. The illumination or energy in this case is said to be the "far field". Phased arrays can be used for the microwave and ultrasound illumination application or even for the laser light beam source.

Figure 41:
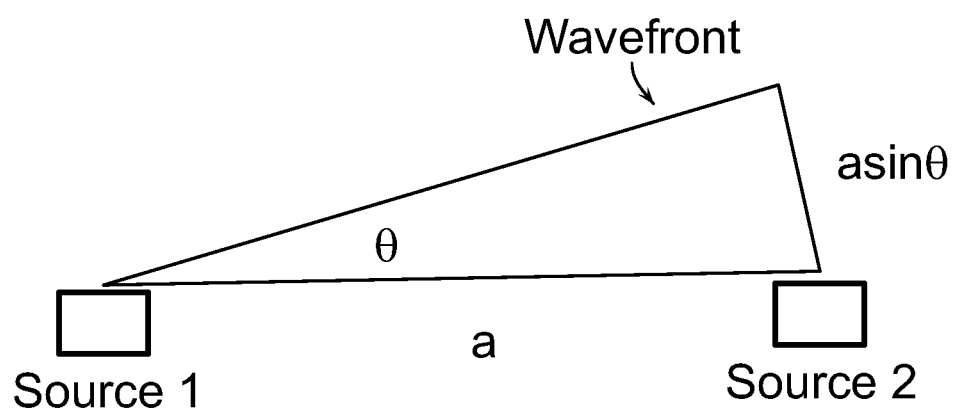
FIG. 41 is a graph depicting wavefront from two sources separated by a distance.

Steering for microwave, ultrasound and even for laser energy sources may be done by use of multiple sources which provide an "array". The basic idea for steering the illumination radiation pattern of an array is constructive (and destructive) interference between the radiation from the individual members of the array of sources. With reference to FIG. 41, to illustrate this, it is only necessary to consider two adjacent members of the array. FIG. 41 depicts the wavefront originating from two adjacent sources.

It is evident that for a wavefront that is depicted at an angle $\theta$ with respect to the distance a between the two sources, the amplitude of the wave from the source on the left is proportional to $\exp[i\omega t]$ whereas the amplitude of the wave from the source on the right is proportional to $\exp[i\omega t - ka \sin\theta - \phi)]$, where $\omega$ is the angular frequency of the radiation, and $k=2\pi/\lambda$.

For constructive interference, these two waves should be "in phase", i.e.

$$\phi\text{constructive}=ka \sin\theta+2n\pi \qquad [14]$$

For destructive interference, these two waves should be "out of phase", i.e.

$$\phi\text{destructive}=ka \sin\theta+(2n+1)\pi \qquad [15]$$

Accordingly, the illumination will be large in the directions $\theta$ given by $$\sin\theta=(1/ka)[\phi\text{constructive}-2n\pi] \qquad [16]$$

In other words, the radiation can be steered to different desired directions $\theta$ simply by choosing different delays $\phi$.

The delays can be introduced electronically into the circuits for exciting the radiation sources. The means for doing this have also been well discussed in the published literature: analog delay circuits are available as well as digital delay circuits.

Radiation patterns for microwave, ultrasound, and laser sources are quite well-directed. If we estimate the divergence of the radiation beam from a source of transverse dimension 2b by the Airy disc expression $$\Theta 1/2=0.6\lambda/b \qquad [17]$$

Then at a target distance D from the source, the half-width w of the illuminated region is roughly $$w=0.6\lambda D/b \qquad [18]$$

If we require the separation of the illuminated regions to be 2w, then the separation of the source s is roughly 3w:

$$a=1.8\lambda D/b \qquad [19]$$

This can be a small separation if the source size is chosen to be much larger than the radiation wavelength.

For example, for ultrasound, suppose we have a 5 MHz source with a transverse dimension of 1 cm, and suppose the desired target distance is 10 cm. Then the separation distance is a≈0.5 cm.

As another example, a commercially available microwave standard gain horn source, operating at 140-220 GHz has transverse dimensions of 13.9 mm by 10.8 mm and a depth dimension of 32.2 mm. For 200 GHz, the wavelength is 0.15 cm, and for a target distance of 10 cm, the target width given by the equation [18] is 1.2×0.15×10/0.6=3 cm. For the spacing a of the horns, eq. [19] then gives 9 cm.

Next, apply eqs. [17]-[19] to obtain rough estimates for a steerable array of 810 nm laser radiation. Suppose b=2×810 nm, and suppose D=1 mm. Then eqs. [17]-[19] give $\Theta 1/2=0.3$, w=0.3 mm, and a=0.9 mm.

For the radiofrequency application, however, the wavelength of the radiofrequency radiation is typically much larger than a human body dimensions. In that case, the treatment volume is said to be in the "near field" of the radiofrequency source. Phased arrays are not useful in near field, and a different method of steering is required.

For radio frequency treatment, the wavelength of the radiation is much larger than body dimensions. Thus, for 3-6 MHz, the wavelengths range from 10,000 cm to 5000 cm. Accordingly, the target region in the body is in the "near field" of the source, i.e. the target distance and dimensions are much less than the wavelength of the RF radiation. This means that the relevant treatment fields are not radiation fields (as they were in the case of microwave, ultrasound, and laser treatments), but are instead induction fields.

The induction field from an RF coil is only large over dimensions comparable to the coil dimension. The induction magnetic fields drop off rapidly as 1/r3 for distances larger than this. Accordingly, for a coil at the surface of the body, we can picture the treatment volume as roughly a hemisphere with radius equal to that of the coil.

For coils with radii between 2 and 6 mm, the treatment volumes for these coils are rather close to the surface (distances comparable to the coil dimensions). Larger coils can be used for deeper targets. In keeping with the spacing criteria discussed earlier, the spacing between the coils in a surface array would be chosen to be comparable to the individual coil dimensions.

For the laser or other light beam and ultrasound sources, the wavelengths are much less than the distances from the sources to the target tissue. For these sources, then, the intensity distributions from the arrays can be calculated in the "far field" approximation. However, for the RF sources, the wavelength is much larger than the distances between the sources to the target tissue. For these sources, the intensity distribution be calculated in the "near field" approximation. For microwaves, at high frequencies, the wavelengths are much less than the distance between the sources and target tissue; however, at low microwave frequencies, the wavelengths can be larger than the distance between the sources and the target tissues. (Thus, at 1 and 100 GHz, the wavelengths are 30 cm and 3 mm, respectively). Accordingly, at high microwave frequencies, the "far field" approximation applies, while at low microwave frequencies, the "near field" approximation applies.

In the far field approximation, the expressions treat $kR \gg 1$, where $k=2\pi/\lambda$ is the wavenumber, $\lambda$ is the wavelength, and R is a typical distance between the source and target: In this approximation, the energy is "radiated" from the source to the target. In the near field approximation, the expressions treat $kR \ll 1$: In this approximation, the fields are not radiation fields, but are "induction" fields. The array behaviors are markedly different in the two approximations.

Figure 42:
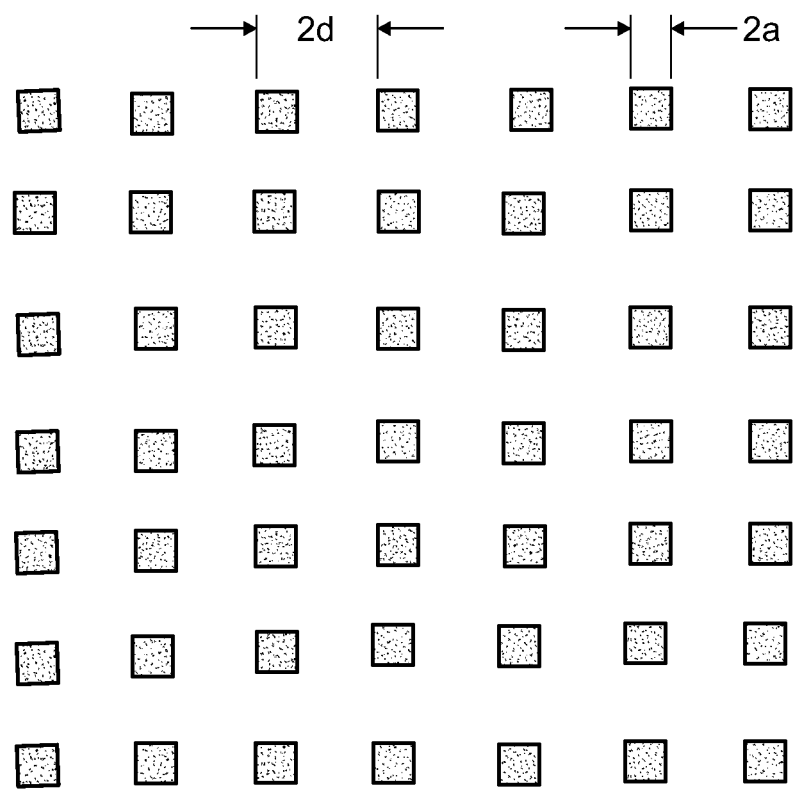
FIG. 42 is a depiction of a square array of square antennas or sources, which can be used in accordance with the present invention.

For far field "radiation" arrays, the following is taken into account. With reference now to FIG. 42, a square array of square antennas or radiation sources is shown. Each antenna has a side of length 2a, and the shortest distance between the centers of adjacent antennas is 2d. There are a total of N antennas along a line in the x direction and N antennas along the y-direction, for a total of $N^2$ antennas.

On using the far field approximation, we find for the intensity $I_p$ at a distant observation point P:

$$I_p/I_o = \{4k^2a^4/(\pi^2R_o^2)\}\text{Sinc}^2\{k\alpha a\}\text{Sinc}^2(k\beta a)\{\text{Sin}(Nk\alpha d)/\text{Sin}(k\alpha d)\}^2\{\text{Sin}(Nk\beta d)/\text{Sin}(k\beta d)\}^2 \quad [20]$$

In this expression, it is assumed that the observation point is located a distance $R_o$ from the antenna array and that the intensity from a single antenna is $I_o$. In addition, $\alpha$ and $\beta$ are the deflection angles in the x and y directions, respectively, and $$\text{Sinc}(v)=\text{Sin}(v)/v \quad [21]$$

Equation [20] can also be written in terms of the coordinates X and Y along the x and y directions in the observation plane by using the approximate relations $$\alpha = X/R_o \quad [22]$$

$$\beta = Y/R_o \quad [23]$$

Figure 43:
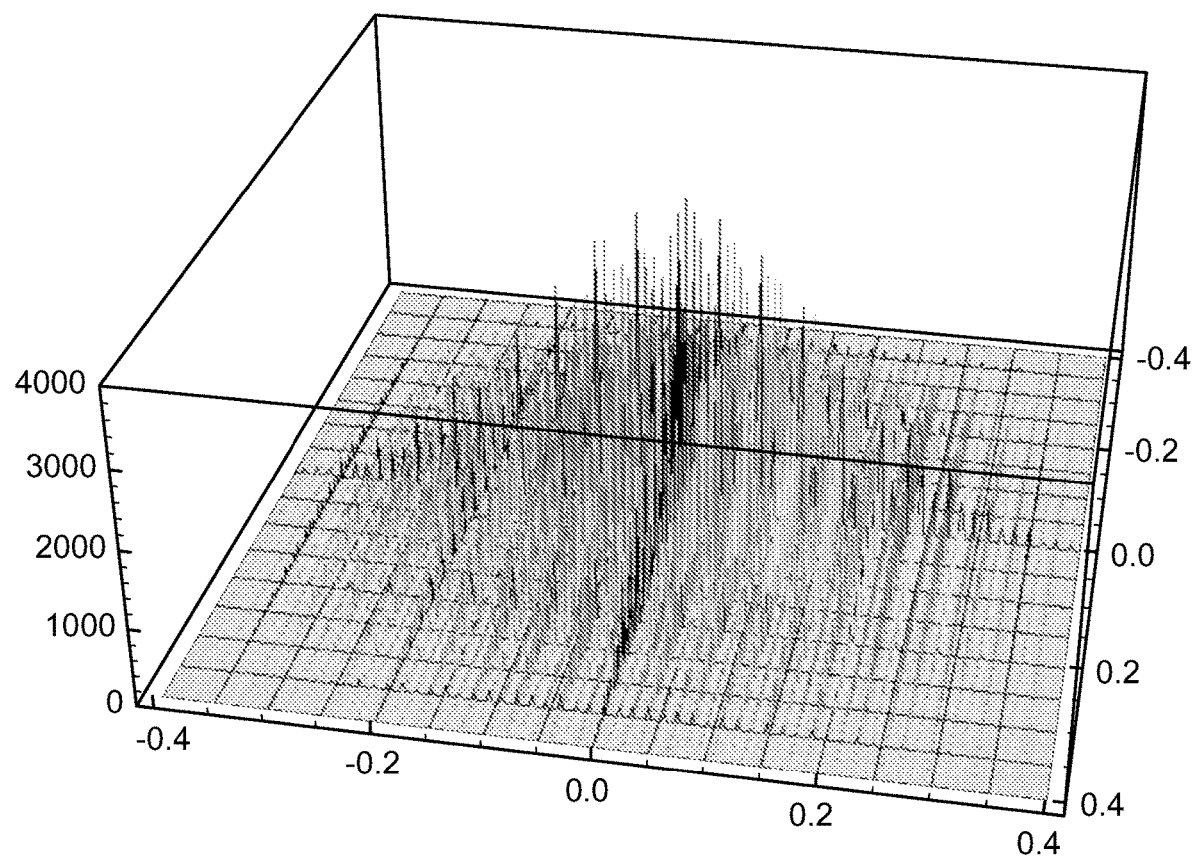
FIG. 43 is a graph depicting the shape of radiation pattern from a square antenna array.

From eq. [20], we can see what the specific form of the radiation pattern from the array is. FIG. 43 is a plot of a typical radiation pattern from a square array. (Anomalies in the plot appear due to the plotting routine employed. Because of plotting inaccuracies, there is randomness in the height of some of the peaks which should not be present, and not all of the peaks are actually shown.) The X and Z dimensions are shown in centimeters, but these dimensions can be changed easily in the equations below.

Figure 44:
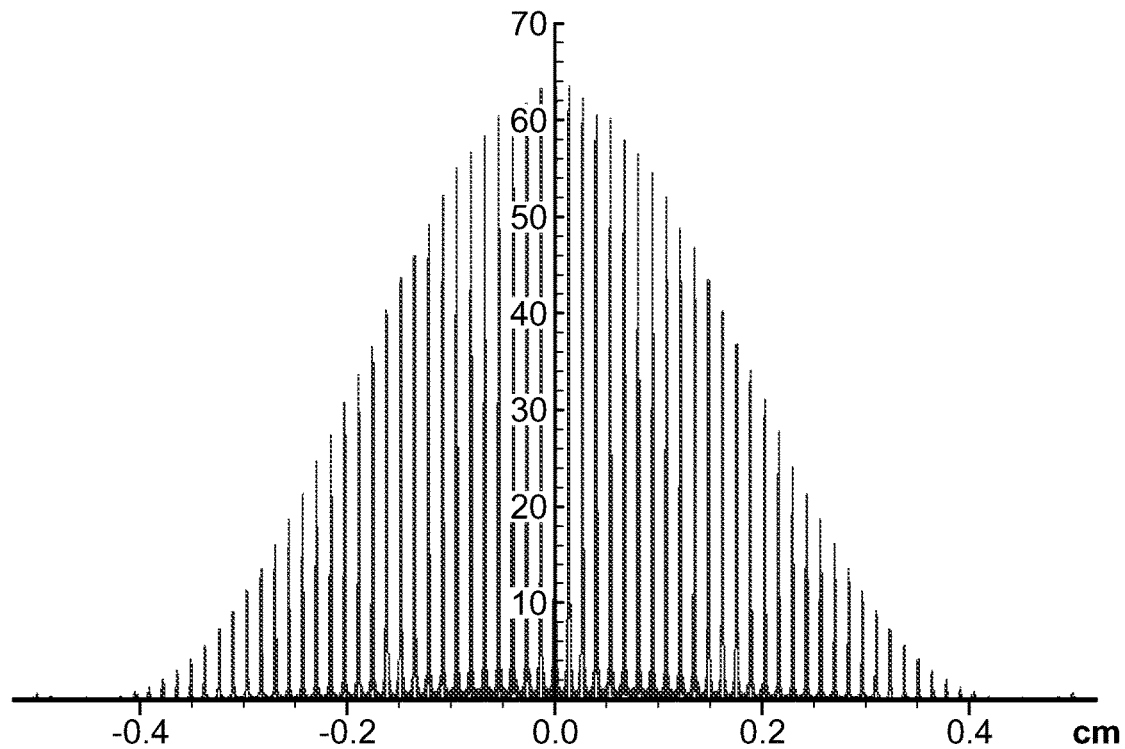
FIG. 44 is a graph depicting a form of typical radiation pattern along an X-axis from a far field array.

FIG. 44 is the form of a typical radiation pattern along the X-axis for a typical radiation pattern from a "far field" array. The pattern results from the individual features shown in FIGS. 45-47.

Specifically, it is plot of $$\text{Sinc}^2\{k(X/R_o)a\}\{\text{Sin}(NkX/R_o)d)/\text{Sin}(k(X/R_o)d)\}^2$$

Figure 45:
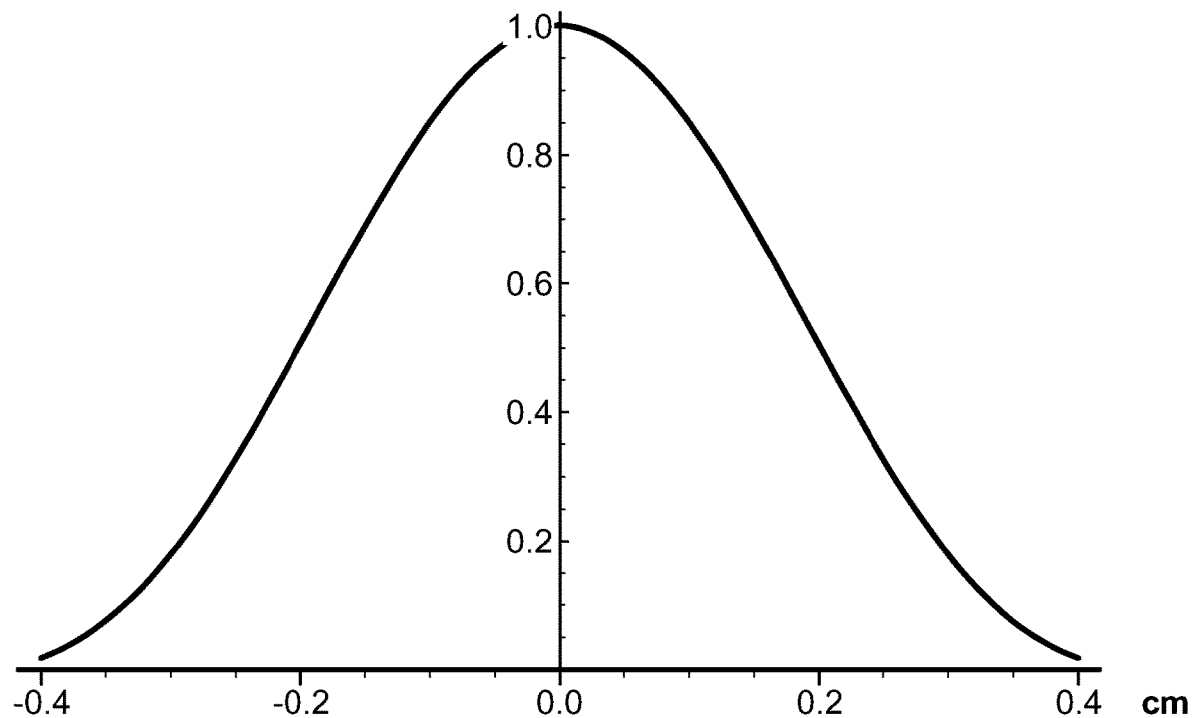
FIG. 45 is a graph depicting an envelope of the pattern of FIG. 44.
Figure 46:
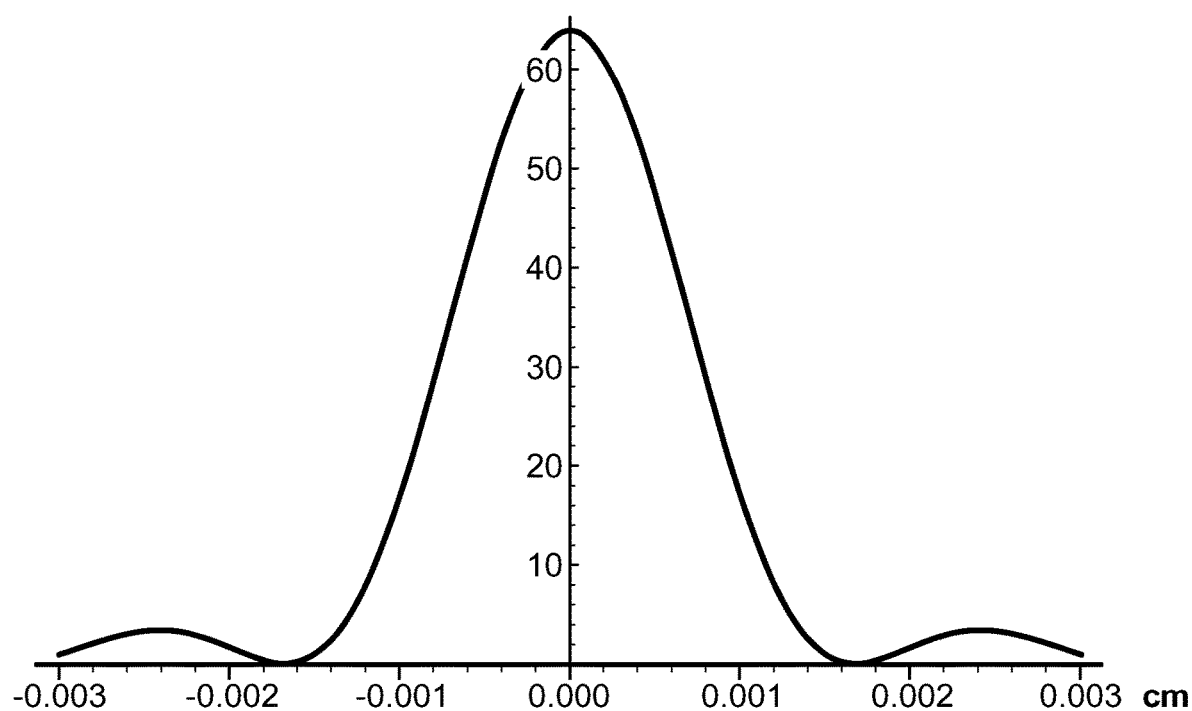
FIG. 46 is another graph depicting the width of individual lines of the pattern of FIG. 44.
Figure 47:
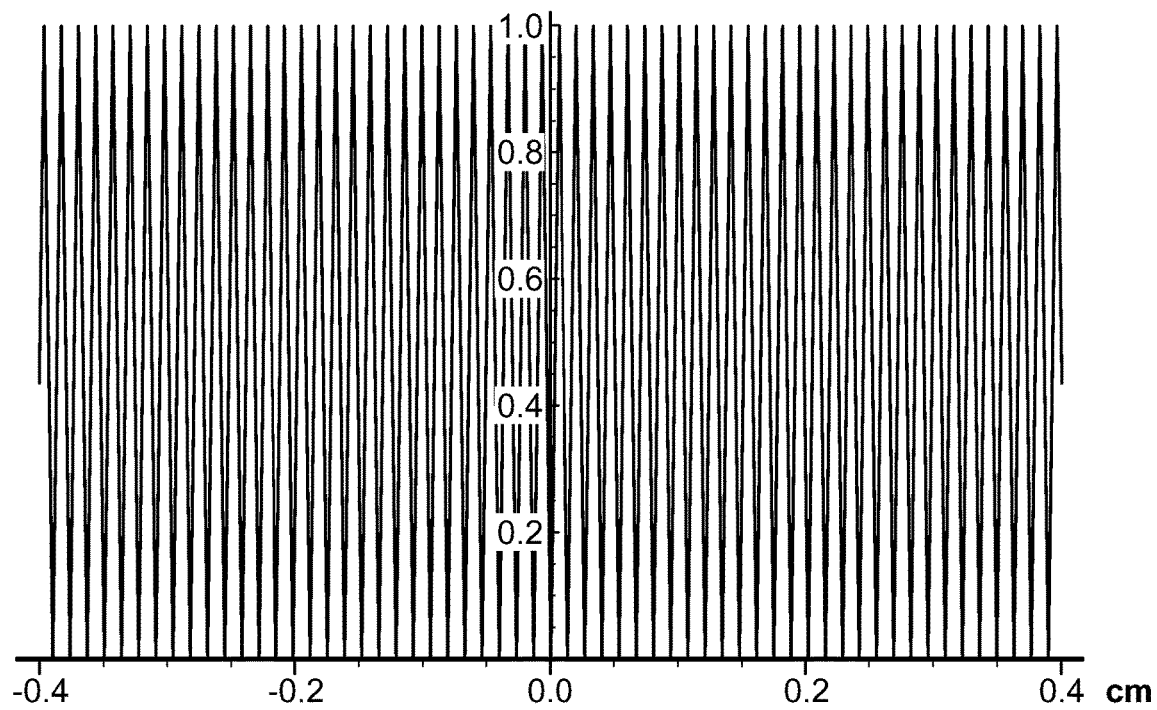
FIG. 47 is a plot graph depicting the determinant of the line separation.

The envelope of the pattern is determined by the $\text{Sinc}^2\{k(X/R_o)a\}$ function. This is shown in FIG. 45. The width of the individual lines is determined by the $\text{Sin}^2(NkX/R_o)d)$ function. This is shown in FIG. 46. Finally, the separation of the lines is determined by the $\text{Sin}^2(kX/R_o)d)$ in the denominator. The lines occur every time the function has a zero, i.e. whenever the argument of the function is some multiple of π. The function is plotted in FIG. 47.

With continuing reference to FIGS. 42-47, the widths of the individual lines and the envelope are determined by the half-widths of the $\text{Sin}^2(Nk\alpha d)$ and $\text{Sinc}^2(k\alpha a)$ functions, respectively, and the spacing between the lines is determined by the zeros of the $\text{Sin}^2((k\alpha d)$ function.

Thus, we can write directly:

| | | |
|---|---|---|
| Width of envelope: | $\Delta_{env} \alpha = \xi(\lambda/a)$ | [24] |
| Spacing between lines (spots): | $\Delta_{sep} \alpha = \lambda/(2d)$ | [25] |
| Width of a single line (spot): | $\Delta_{line} \alpha = \xi(\lambda/Nd)$ | [26] |
| Number of lines (spots) along X-axis: | $N = 2\xi(d/a)$ | [27a] |
| Number of spots in square pattern | $N^2 = 4\xi^2(d/a)^2$ | [27b] |

In these expressions $\xi$ is a fraction on the order of ½ that describes where the corresponding Sinc or Sin function is about half-max. (If it is desired to observe only where these functions are larger and more uniform in magnitude, then $\xi$ can be chosen smaller.)

A far field array, such as that illustrated in FIG. 42, can be selectively and controllably steered. The position of the peaks can be changed by introducing a phase delay in the excitation of the antennas. Thus, the direction in the X direction can be changed by introducing a phase delay $\phi_n$ in the nth antenna in the X-direction, that is proportional to n. To change the direction from $\alpha=0$ to an arbitrary $\alpha_o$, the phase delay of the nth antenna in the X direction is $$\phi_n = -\alpha_o nkd. \quad [28a]$$

In a similar manner the maximum peak direction in the Y direction can be shifted from $\beta=0$ to an arbitrary $\beta_o$. To change the direction from β=0 to an arbitrary $\beta_o$, an additional phase delay is introduced to the mth antenna in the Y direction is $$\phi_m = -\beta_o mkd \quad [28b]$$

Figure 48:
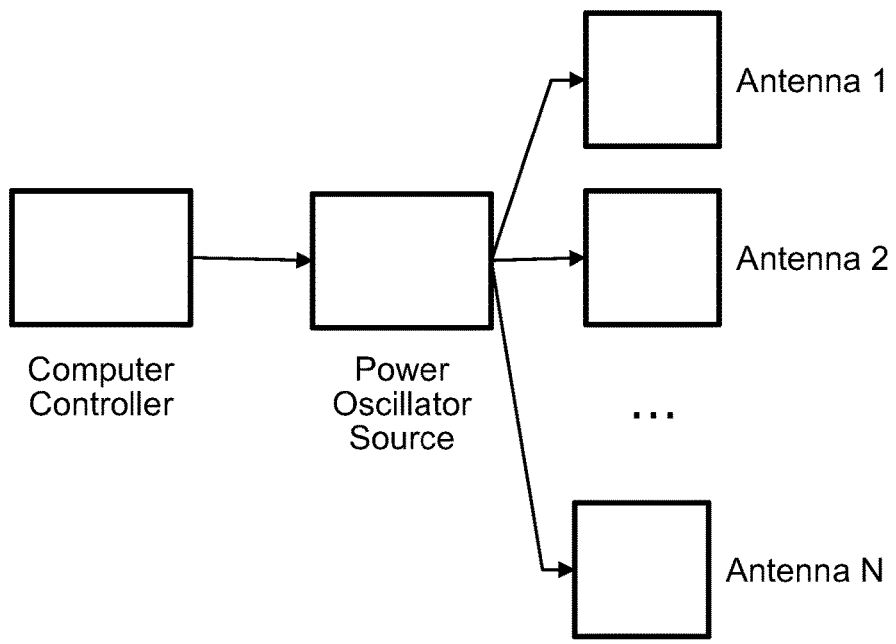
FIG. 48 is a block diagram of components of a steerable array system.

With reference now to FIG. 48, a block diagram of its system for exciting the antennas in the array, such as that illustrated in FIG. 42, to irradiate a target tissue is shown. The array system of FIG. 48 is applicable for the light beam, ultrasound and high frequency microwave arrays. The computer controller provides the desired power excitation and phase delays for steering the array. The computer-controlled oscillator source activates the antennas with appropriate phase delays to steer the antenna array peaks, as described above.

A near field (induction) array, and particularly the steering of such near field arrays, for low frequency microwaves and RF differs markedly from the far field arrays discussed above.

As an example, consider the near field (induction electric field) from a circular coil carrying an alternating current I. If the coil lies in the X-Y plane with its axis along the Z-direction, then the vector potential A is in the azimuthal direction, and is given by $$A_\phi = (\mu I/\pi k)(a/\rho)^{1/2}[\{1-(k^2/2)\}K(k^2)-E(k^2)] \quad [29]$$

with $$k^2 = 4a\rho[(a+\rho)^2+Z^2]^{-1} \quad [30]$$

Here
μ is the magnetic permeability of free space
a is the radius of the current carrying coil $$\rho = (X^2+Y^2)^{1/2}$$

E is the complete elliptic integral of the second kind
K is the complete elliptic integral of the first kind
The induction electric field is also in the azimuthal direction, and is given by $$E_\phi = -i\omega A_\phi \quad [31]$$

where
ω is the angular frequency of the alternating current I.
The objective of the induction field is to heat the tissue to activate heat shock proteins. The heating is achieved by dielectric or Ohmic heating: Accordingly, the temperature rise in the tissue is proportional to $\text{Im}(\epsilon)(\omega A_\phi)^2$.

Figure 49:
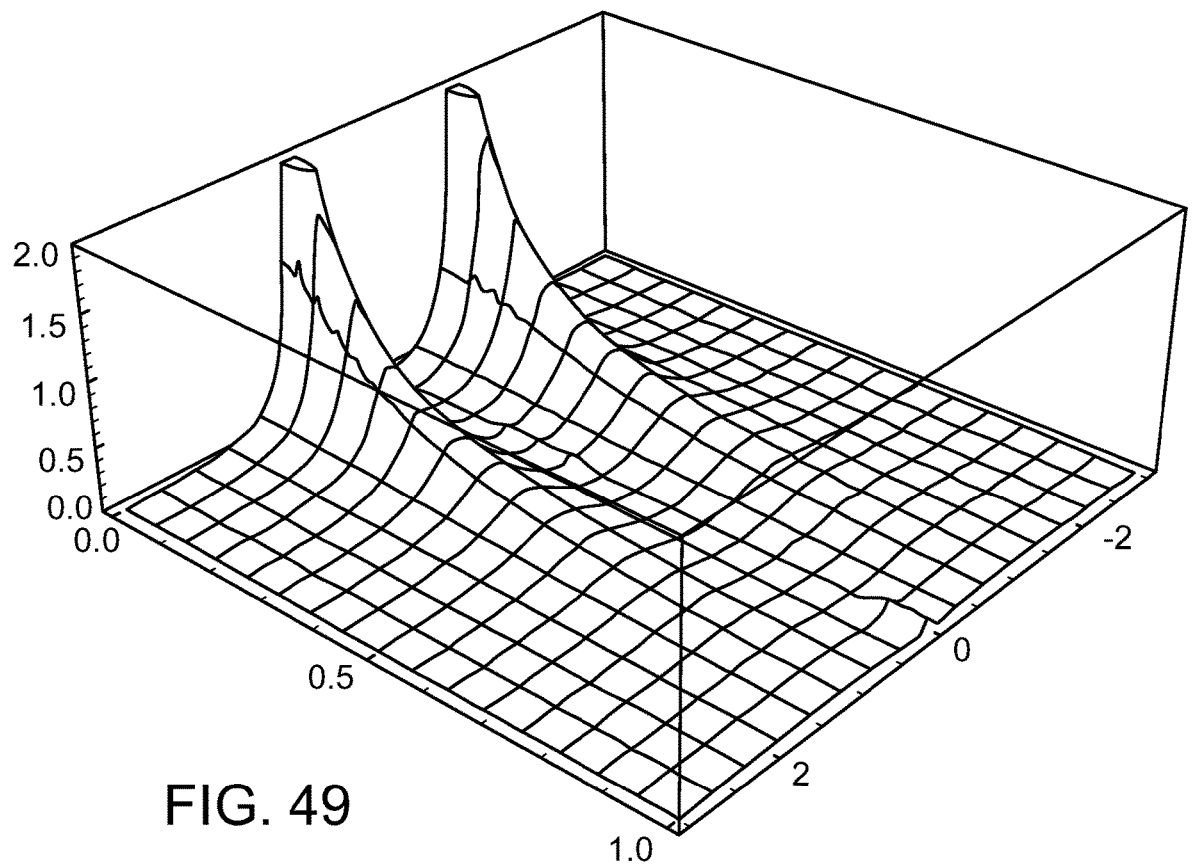
FIG. 49 is a plot graph showing induced tissue temperature rise and drops.

FIG. 49 is a plot of $(\pi A_\phi/\mu I)^2$ vs the dimensionless variables x'=X/a and z'=Z/a for a coil of radius a in the Z=0 plane with its center at X=Y=0. In the figure, x' ranges from −3 to +3, and z' ranges from 0 to 1.

With continuing reference to FIG. 49, it is shown that the induced tissue temperature rise drops off rapidly as the axial distance from the coil increases. The tissue between the coil and about an axial distance equal to the radius of the coil divided by 2 can be expected to experience a temperature rise. Thus, if it is desired to heat a tissue that is 5 cm from the surface, where the coil sits, the coil should be approximately 10 cm in diameter. FIG. 49 also shows that the main heating will occur in a circular ring equal in radius to the coil radius.

Figure 50:
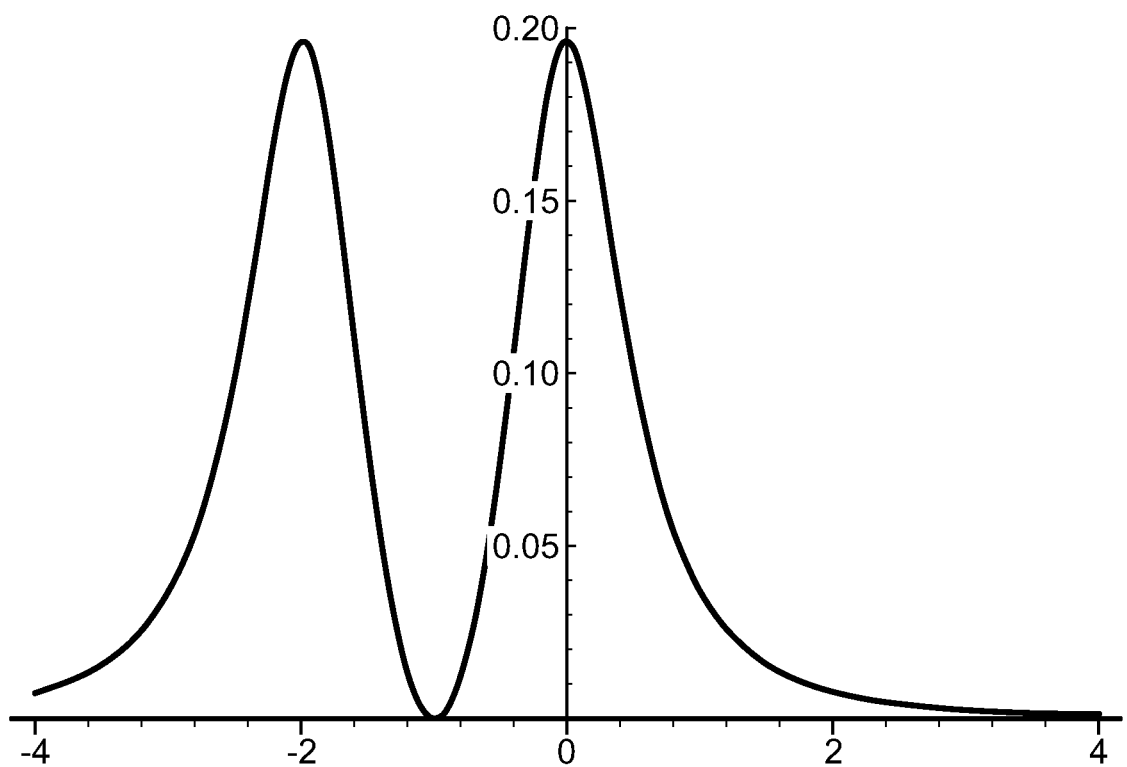
FIGS. 50-52 are graphs depicting variables of three different coils, in accordance with the present invention.
Figure 51:
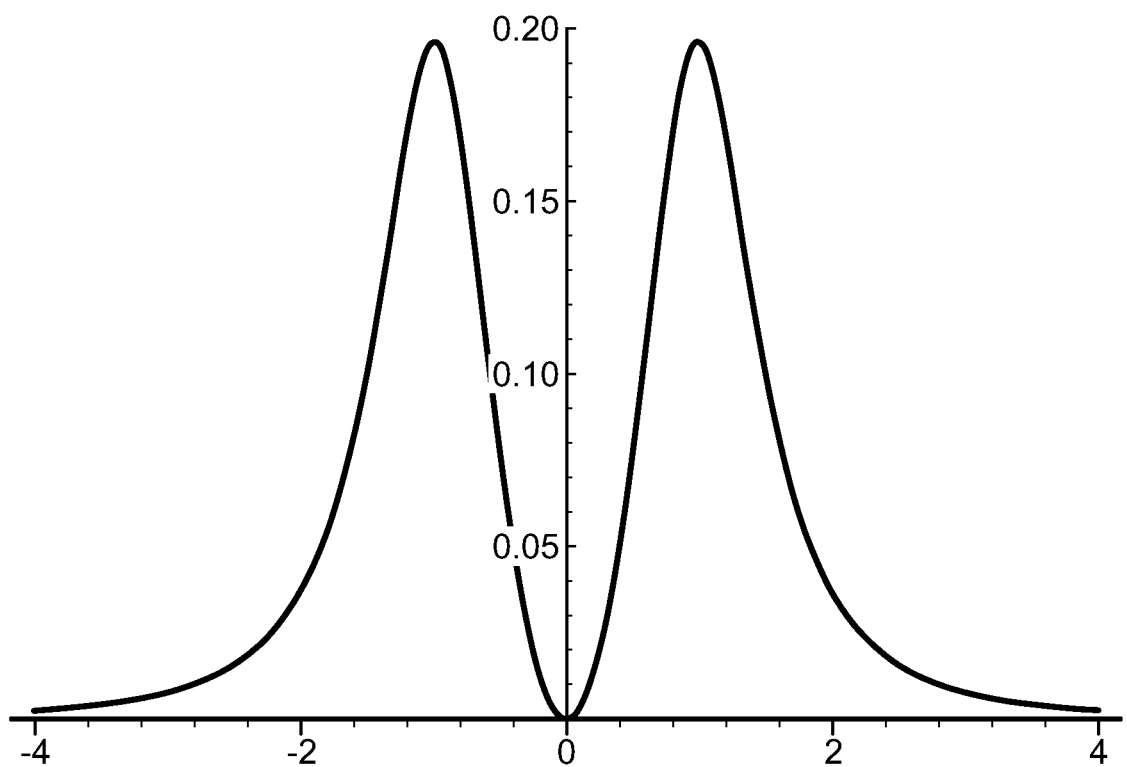
Figure 52:
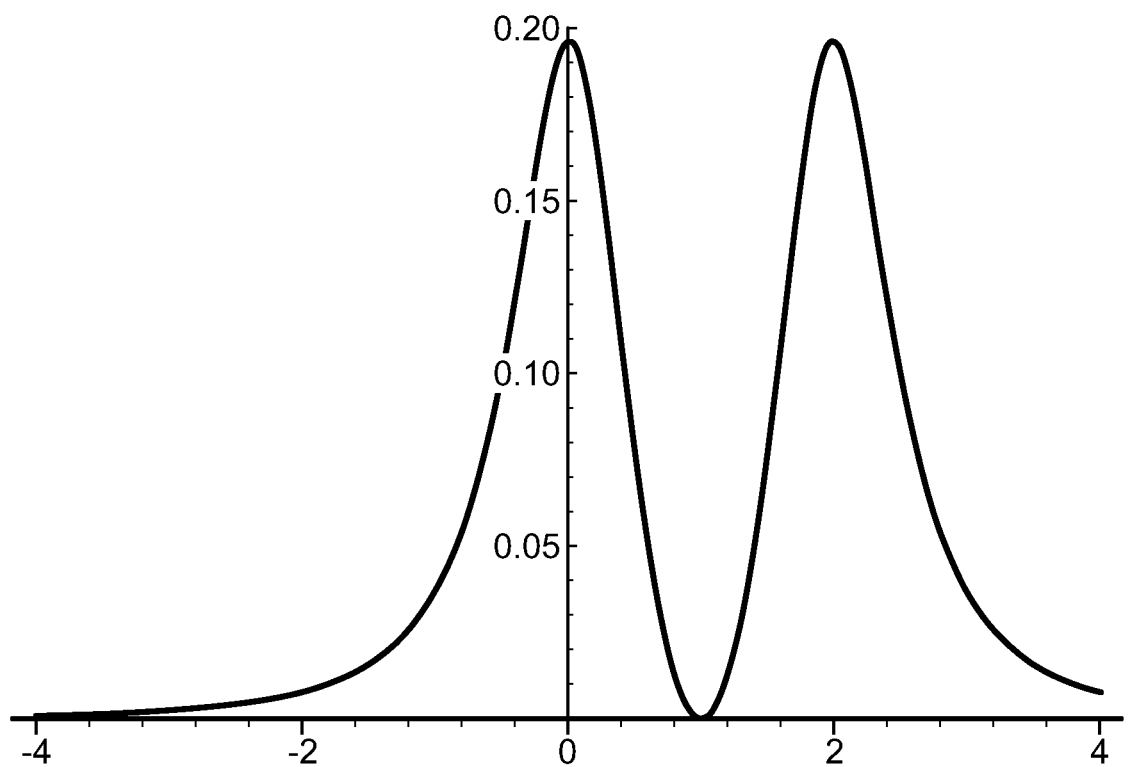

To illustrate the latter point, FIGS. 50-52 show $(\pi A_\phi/\mu I)^2$ vs the dimensionless variables x'=X/a at z'=0.5 for three different coils of the same radius a. FIG. 50 is for a coil with its center at X=−a. FIG. 51 is for a coil with its center at X=0, and FIG. 52 is for a coil with its center at X=+a. FIG. 50 illustrates $(\pi A_\phi/\mu I)^2$ vs the dimensionless variable x'=X/a at z'=Z/a=0.5 for a coil of radius a in the Z=0 plane with its center at X=−a, Y=0. FIG. 51 illustrates $(\pi A_\phi/\mu I)^2$ vs the dimensionless variable x'=X/a at z'=Z/a=0.5 for a coil of radius a in the Z=0 plane with its center at X=Y=0. FIG. 52 illustrates $(\pi A_\phi/\mu I)^2$ vs the dimensionless variable x'=X/a at z'=Z/a=0.5 for a coil of radius a in the Z=0 plane with its center at X=+a and Y=0.

Figure 53:
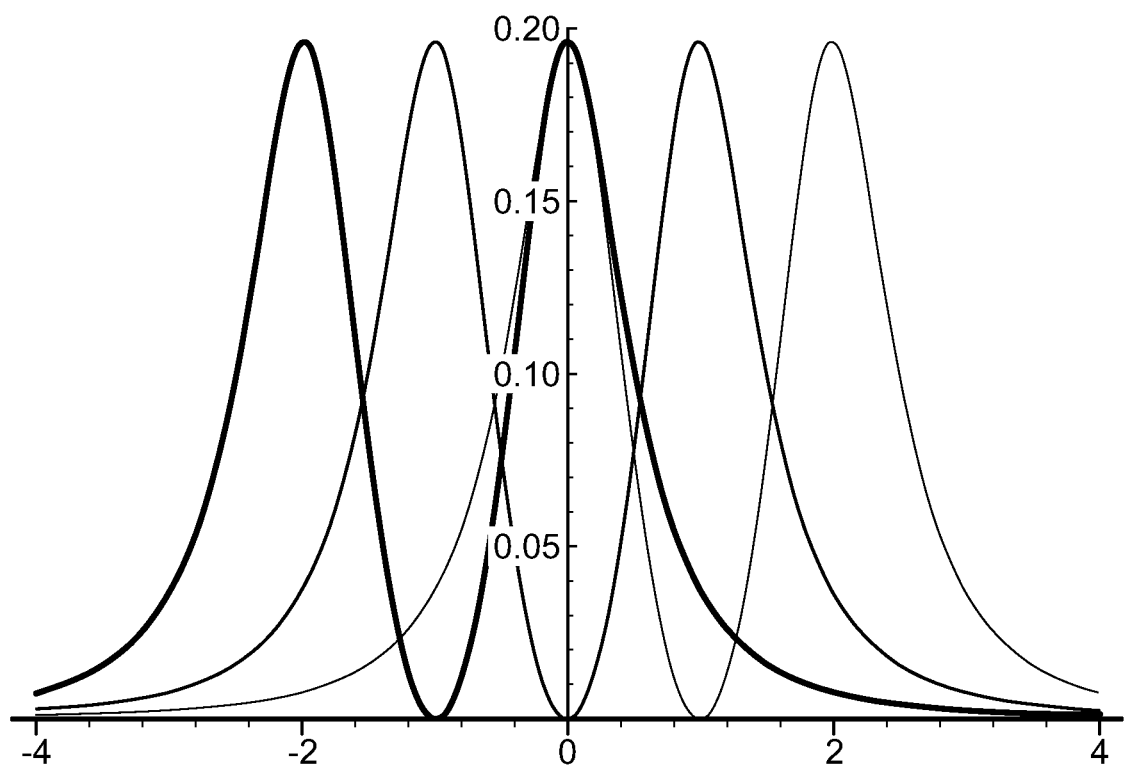
FIG. 53 is a graph depicting the plots of FIGS. 50-52 superimposed upon one another.

FIG. 53 shows the plots of FIGS. 50-52 superimposed, where $(\pi A_\phi/\mu I)^2$ vs the dimensionless variable x'=X/a at z'=Z/a=0.5 for three different locations of a coil of radius a in the z'=0 plane. The left-most curve is for a coil with its center at X=−a and Y=0; the middle curve is for a coil with its center at X=Y=0; and the right-most curve is for a coil with its center at X=a and Y=0.

With continuing reference to FIGS. 49-53, with respect to depth of treatment, if a tissue at a distance $Z_o$ needs to be treated by induction heating, a coil of radius $2Z_0$ should be used. It will treat all tissue between the surface and $Z_o$. For steering, for induction fields, the way to treat different transverse positions is not to "steer" an array by phase delay, but rather to activate individual coils sequentially. Each activated coil will treat the region below it, primarily in a circular strip beneath its circumference.

Figure 54:
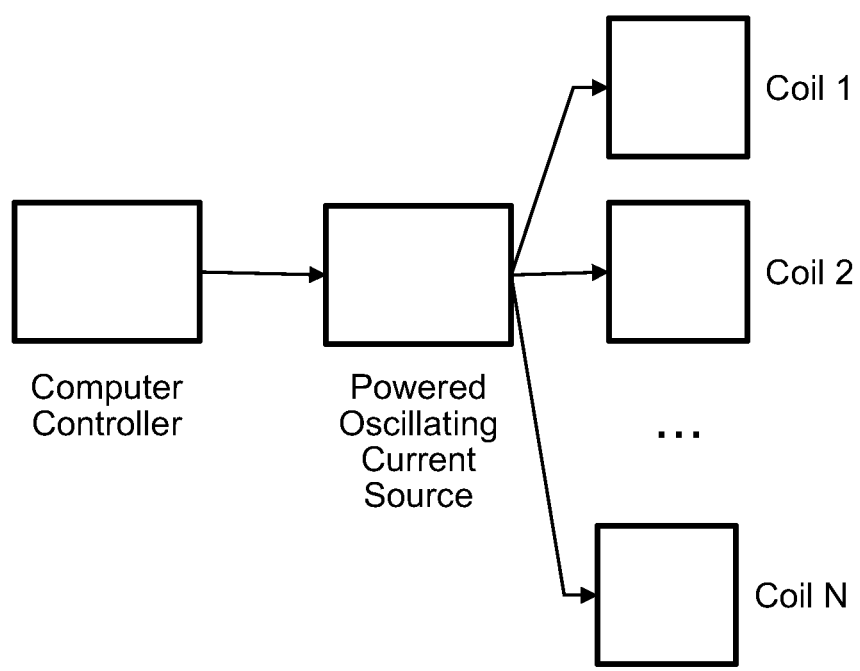
FIG. 54 is a block diagram for an induction array which can be used in accordance with the present invention.

With reference now to FIG. 54, a block diagram for an induction array (near field) for RF sources and low-frequency microwave sources is shown. Here, the computer-controlled powered oscillating current source selects the coils sequentially in order to treat different transverse tissue positions. Thus, coils 1-N are powered sequentially in order to steer the induction fields. Thus, for the different types of radiation or energy, a different steering mechanism or system is utilized in order to treat the desired tissue at a desired depth.

As mentioned above, the controlled manner of applying energy to the target tissue is intended to raise the temperature of the target tissue to therapeutically treat the target tissue without destroying or permanently damaging the target tissue. It is believed that such heating activates HSPs and that the thermally activated HSPs work to reset the diseased tissue to a healthy condition, such as by removing and/or repairing damaged proteins. It is believed by the inventors that maximizing such HSP activation improves the therapeutic effect on the targeted tissue. As such, understanding the behavior and activation of HSPs and HSP system species, their generation and activation, temperature ranges for activating HSPs and time frames of the HSP activation or generation and deactivation can be utilized to optimize the heat treatment of the biological target tissue.

As mentioned above, the target tissue is heated by the pulsed energy for a short period of time, such as ten seconds or less, and typically less than one second, such as between 100 milliseconds and 600 milliseconds. The time that the energy is actually applied to the target tissue is typically much less than this in order to provide intervals of time for heat relaxation so that the target tissue does not overheat and become damaged or destroyed. For example, as mentioned above, laser light pulses may last on the order of microseconds with several milliseconds of intervals of relaxed time.

Thus, understanding the sub-second behaviors of HSPs can be important to the present invention. The thermal activation of the HSPs in SDM is typically described by an associated Arrhenius integral, $$\Omega = \int dt A \exp[-E/k_B T(t)] \quad [28]$$

where the integral is over the treatment time and
A is the Arrhenius rate constant for HSP activation
E is the activation energy T(t) is the temperature of the thin RPE layer, including the laser-induced temperature rise The laser-induced temperature rise—and therefore the activation Arrhenius integral—depends on both the treatment parameters (e.g., laser power, duty cycle, total train duration) and on the RPE properties (e.g., absorption coefficients, density of HSPs). It has been found clinically that effective SDM treatment is obtained when the Arrhenius integrals is of the order of unity.

The Arrhenius integral formalism only takes into account a forward reaction, i.e. only the HSP activation reaction): It does not take into account any reverse reactions in which activated HSPs are returned to their inactivated states. For the typical subsecond durations of SDM treatments, this appears to be quite adequate. However, for longer periods of time (e.g. a minute or longer), this formalism is not a good approximation: At these longer times, a whole series of reactions occurs resulting in much smaller effective HSP activation rates. This is the case during the proposed minute or so intervals between SDM applications in the present invention disclosure.

In the published literature, the production and destruction of heat shock proteins (HSPs) in cells over longer durations is usually described by a collection of 9-13 simultaneous mass-balance differential equations that describe the behavior of the various molecular species involved in the life cycle of an HSP molecule. These simultaneous equations are usually solved by computer to show the behavior in time of the HSPs and the other species after the temperature has been suddenly raised.

These equations are all conservation equations based on the reactions of the various molecular species involved in the activity of HSPs. To describe the behavior of the HSPs in the minute or so intervals between repeated applications of SDM, we shall use the equations described in M. Rybinski, Z. Szymanska, S. Lasota, A. Gambin (2013) Modeling the efficacy of hyperthermia treatment. Journal of the Royal Society Interface 10, No. 88, 20130527 (Rybinski et al (2013)). The species considered in Rybinski et al (2013) are shown in Table 4.

TABLE 4

| | |
|---|---|
| HSP | system species in Rybinski et al (2013) description: |
| HSP | ubiquitous heat shock protein of molecular weight 70 Da (in free, activated state) |
| HSF | heat shock (transcription) factor that has no DNA binding capability |
| $HSF_3$ | (trimer) heat shock factor capable of binding to DNA, formed from HSF |
| HSE | heat shock element, a DNA site that initiates transcription of HSP when bound to $HSF_3$ |
| mRNA | messenger RNA molecule for producing HSP |
| S | substrate for HSP binding: a damaged protein |
| P | properly folded protein |
| HSP.HSE | a complex of HSP bound to HSF (unactivated HSPs) |
| $HSF_3$.HSE | a complex of $HSF_3$ bound to HSE, that induces transcription and the creation of a new HSP mRNA molecule |
| HSP.S | a complex of HSP attached to damaged protein (HSP actively repairing the protein) |

The coupled simultaneous mass conservation equations for these 10 species are summarized below as eqs. [29]-[38]:

$$d[HSP]/dt = (I_1+k_{10})[HSPS]+I_2[HSPHSF]+k_4[mRNA]-k_1[S][HSP]-k_2[HSP][HSF]-I_3[HSP][HSF_3]-k_9[HSP] \quad [29]$$

$$d\{HSF\}/dt = I_2[HSPHSF]+2I_3[HSP][HSF_3]+k_6[HSPHSF][S]-k_2[HSP][HSF]-3k_3[HSF]^3-I_6[HSPS][HSF] \quad [30]$$

$$d[S]/dt = k_{11}\{[P]+I_1[HSPS]+I_6[SPS][HSF]-k_1[S][HSP]-k_6[HSPHSF][S] \quad [31]$$

$$d[HSPHSF]/dt = k_2[HSP][HSF]+I_6[HSPS][HSF]+I_3[HSP][HSF_3]-I_2[HSPHSF]-k_6[HSPHSF][S] \quad [32]$$

$$d[HSPS]/dt = k_1[S][HSP]+k_6[HSPHSF][S]-(I_1+k_{10})[HSPS]-I_6[HSPS][HSF] \quad [33]$$

$$d[HSF_3]/dt = k_3[HSF]^3+I_7[HSF_3][HSE]-I_3[HSP][HSF_3]-k_7[HSF_3][HSE] \quad [34]$$

$$d[HSE]/dt = I_7[HSF_3][HSE]-k_7[HSF_3][HSE] \quad [35]$$

$$d[HSF_3HSE]/dt = k_7[HSF_3][HSE]-I_7[HSF_3][HSE] \quad [36]$$

$$d[mRNA]/dt = k_8[HSF_3HSE]-k_5[mRNA] \quad [37]$$

$$d[P]/dt = k_{10}[HSPS]-k_{11}[P] \quad [38]$$

In these expressions, [ ] denotes the cellular concentration of the quantity inside the bracket. For Rybinski et al (2013), the initial concentrations at the equilibrium temperature of 310K are given in Table 5.

TABLE 5

Initial values of species at 310K for a typical cell in arbitrary units [Rybinski et al (2013)] . The arbitrary units are chosen by Rybinski et al for computational convenience: to make the quantities of interest in the range of 0.01-10.

| | |
|---|---|
| [HSP(0)] | 0.308649 |
| [HSF(0)] | 0.150836 |
| [S(0)] | 0.113457 |
| [HSPHSF(0)] | 2.58799 |
| [HSPS(0)] | 1.12631 |
| [$HSF_3$(0)] | 0.0444747 |
| [HSE(0)] | 0.957419 |
| [$HSF_3$HSE(0)] | 0.0425809 |
| [mRNA(0)] | 0.114641 |
| [P(0)] | 8.76023 |

The Rybinski et al (2013) rate constants are shown in Table 6.

TABLE 6

Rybinski et al (2013) rate constants giving rates in $min^{-1}$ for the arbitrary concentration units of the previous table.

| |
|---|
| $I_1$ = 0.0175 |
| $k_1$ = 1.47 |
| $I_2$ = 0.0175 |
| $k_2$ = 1.47 |
| $I_3$ = 0.020125 |
| $k_3$ = 0.0805 |
| $k_4$ = 0.1225 |
| $k_5$ = 0.0455 |
| $k_6$ = 0.0805 |
| $I_6$ = 0.00126 |
| $k_7$ = 0.1225 |
| $I_7$ = 0.1225 |
| $k_8$ = 0.1225 |
| $k_9$ = 0.0455 |
| $k_{10}$ = 0.049 |
| $k_{11}$ = 0.00563271 |

The initial concentration values of Table 5 and the rate constants of Table 6 were determined by Rybinski et al (2013) to correspond to experimental data on overall HSP system behavior when the temperature was increased on the order of 5° C. for several (e.g. 350) minutes.

Note that the initial concentration of HSPs is 100× 0.308649/(8.76023+0.113457+1.12631)}=3.09% of the total number of proteins present in the cell.

Although the rate constants of Table 6 are used by Rybinski et al for T=310+5+315K, it is likely that very similar rate constants exist at other temperatures. In this connection, the qualitative behavior of the simulations is similar for a large range of parameters. For convenience, we shall assume that the values of the rate constants in Table 6 are a good approximation for the values at the equilibrium temperature of T=310K.

Figure 55A:
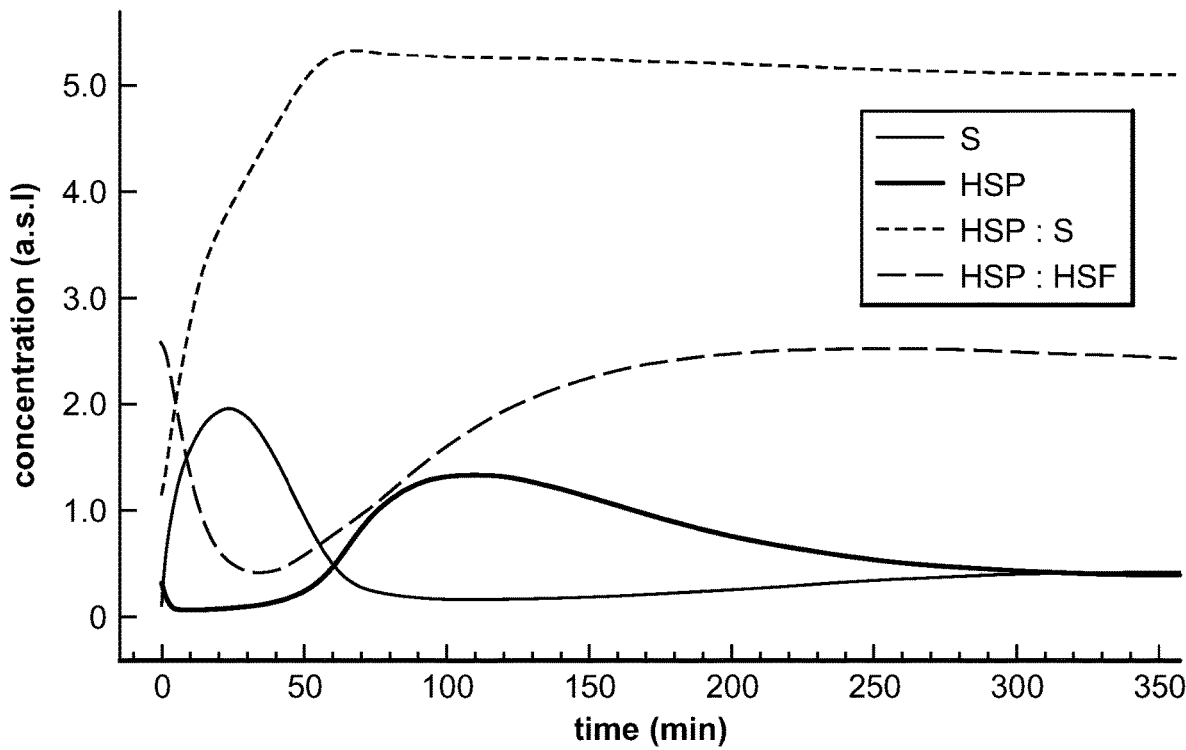
FIGS. 55A and 55B are graphs depicting the behavior of HSP cellular system components over time following a sudden increase in temperature.
Figure 55B:
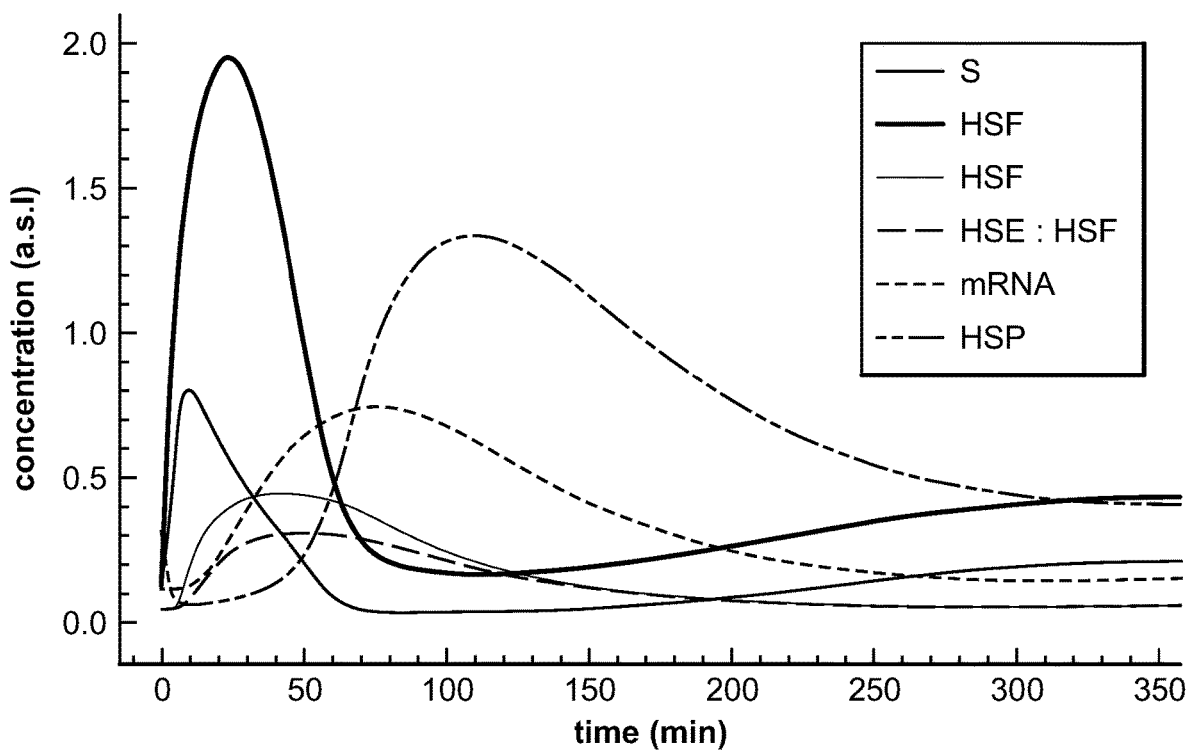
Figure 56A:
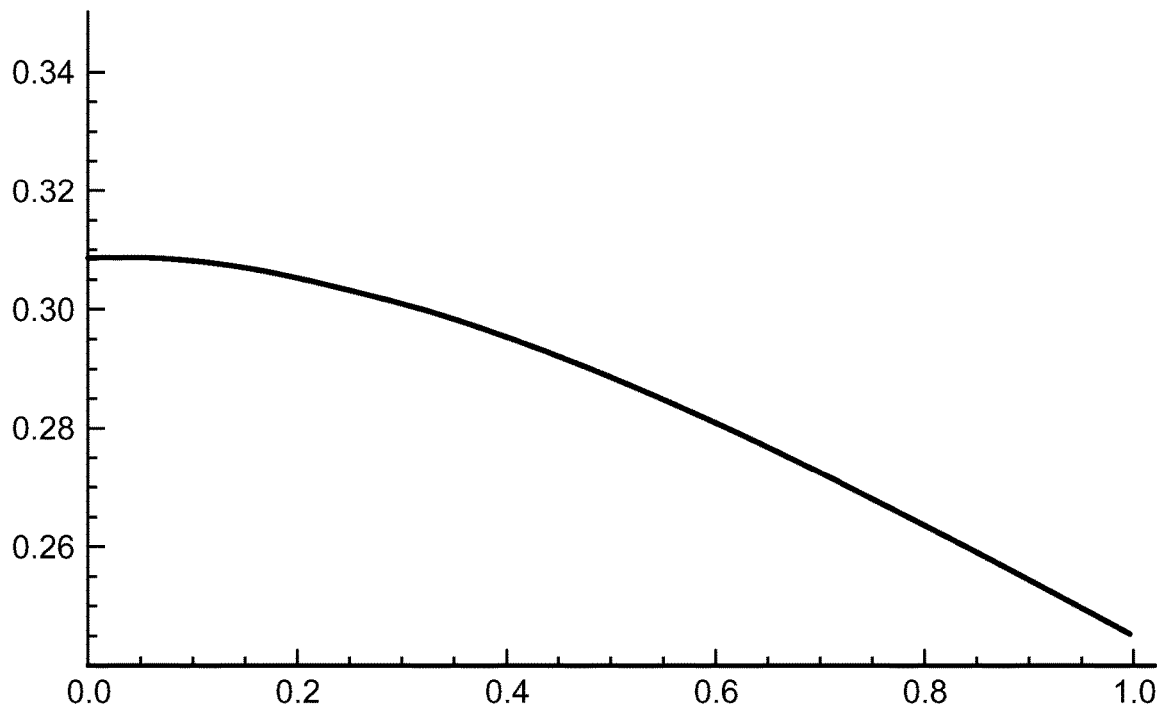
FIGS. 56A-56H are graphs depicting the behavior of HSP cellular system components in the first minute following a sudden increase in temperature.
Figure 56B:
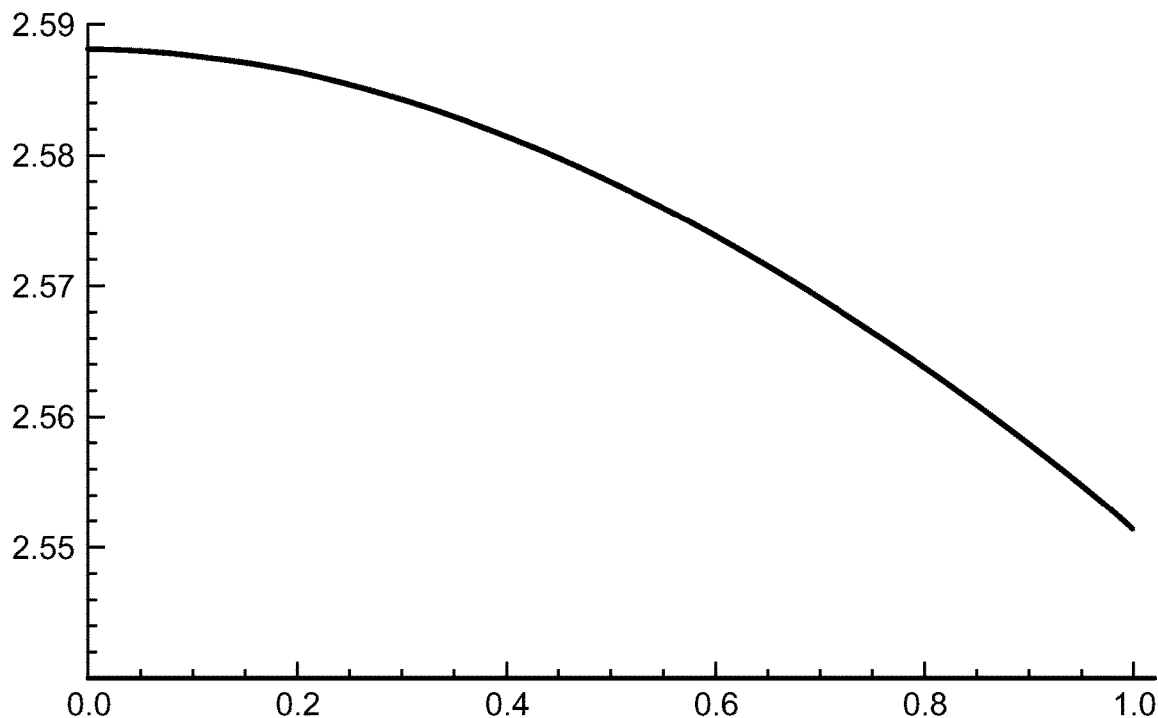
Figure 56C:
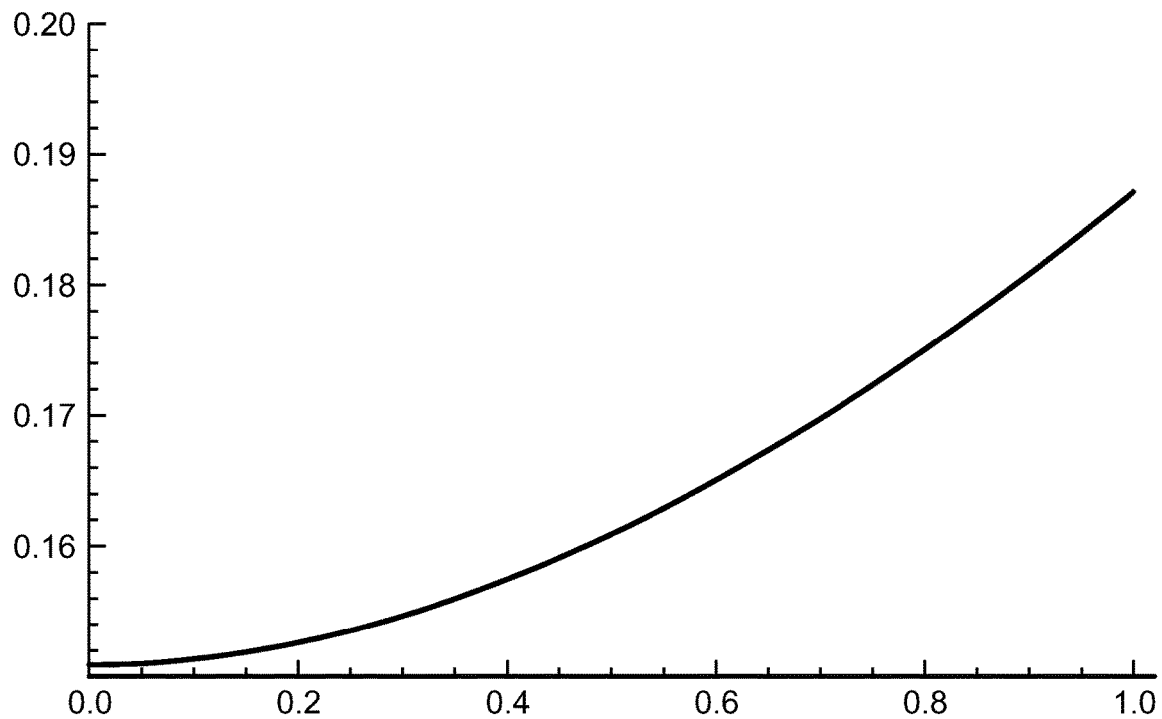
Figure 56D:
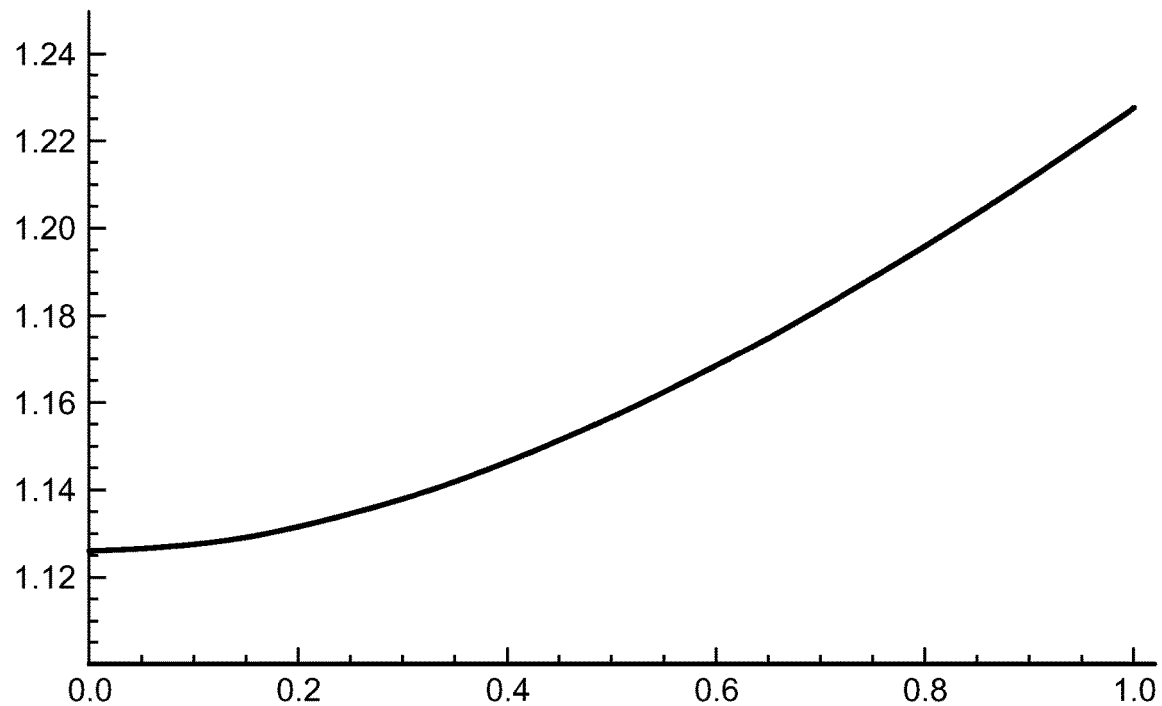
Figure 56E:
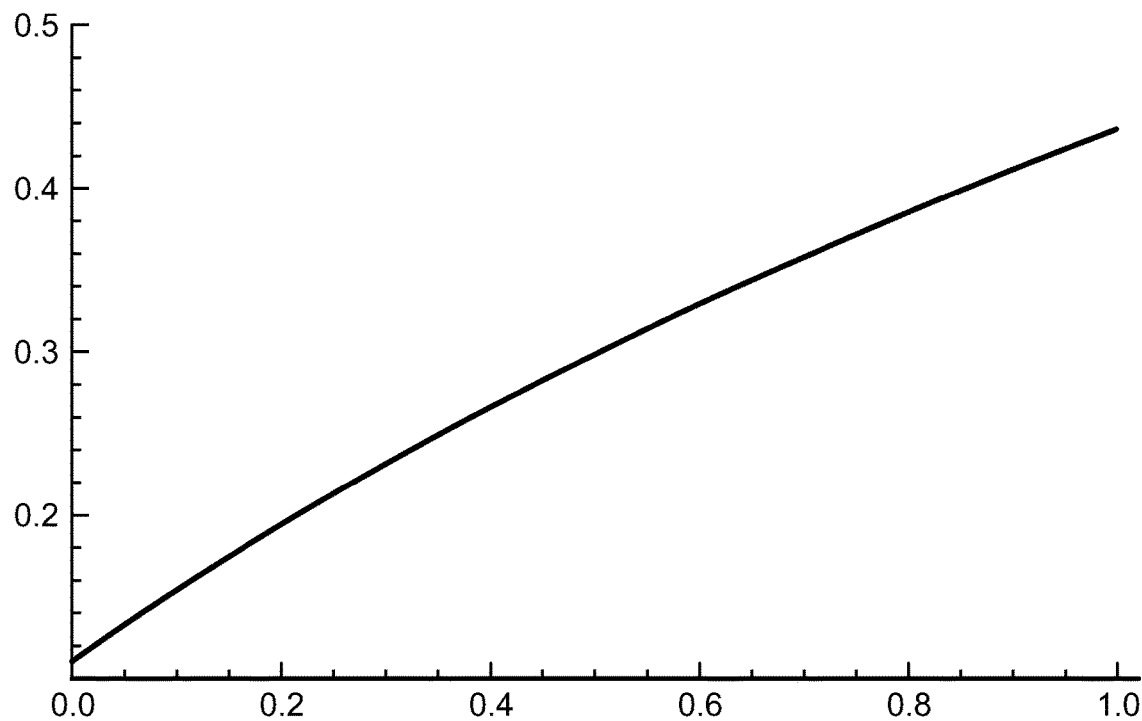
Figure 56F:
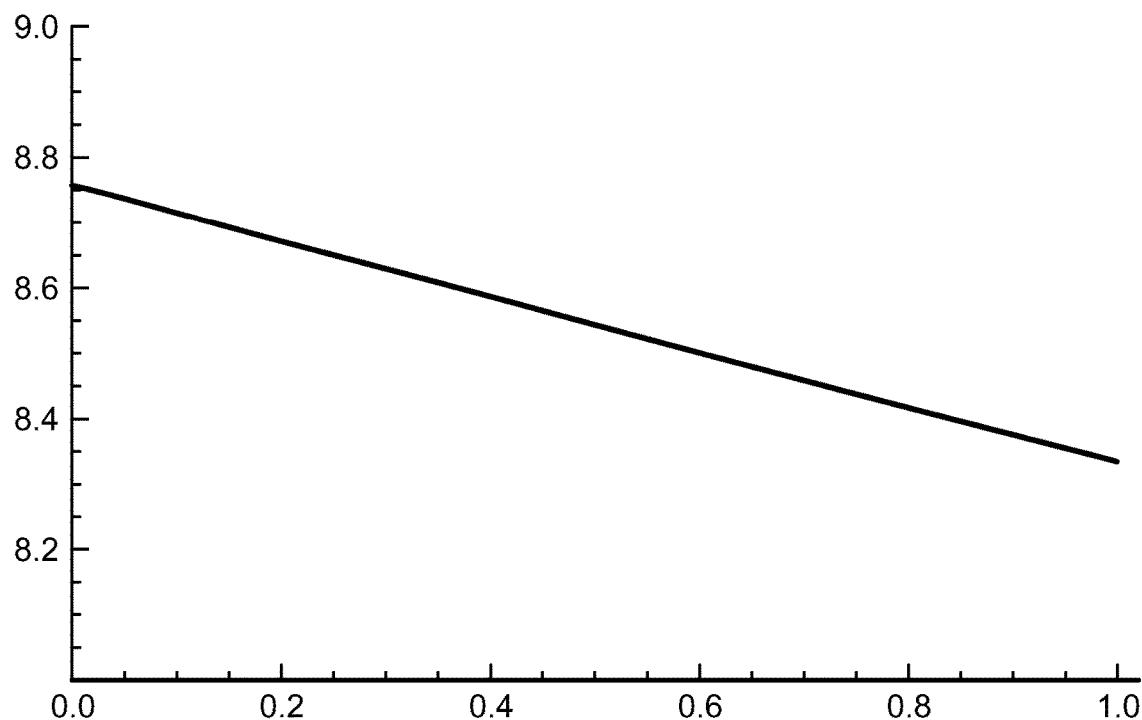
Figure 56G:
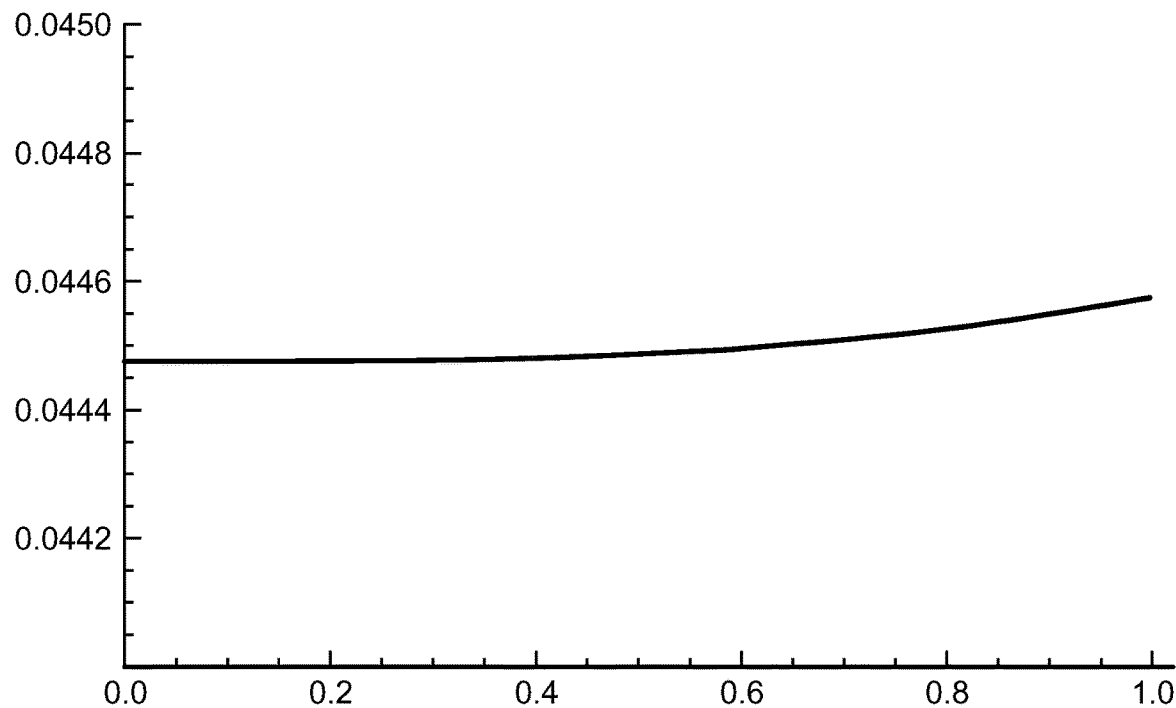
Figure 56H:
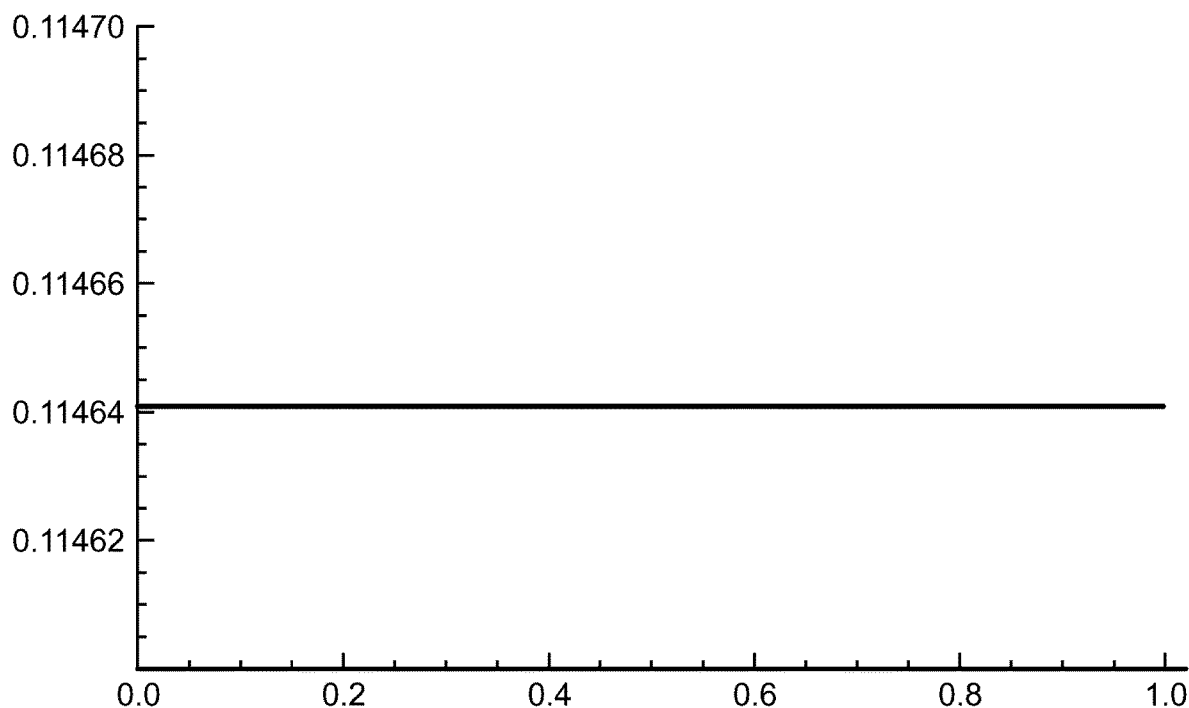

The behavior of the different components in the Rybinski et al cell is displayed in FIGS. 55A and 55B for 350 minutes for the situation where the temperature is suddenly increased 5K at t=0 from an ambient 310K.

With continuing reference to FIG. 55, the behavior of HSP cellular system components during 350 minutes following a sudden increase in temperature from 37° C. to 42° C. is shown.

Here, the concentrations of the components are presented in computationally convenient arbitrary units. S denotes denatured or damaged proteins that are as yet unaffected by HSPs; HSP denotes free (activated) heat shock proteins; HSP:S denotes activated HSPs that are attached to the damaged proteins and performing repair; HSP:HSF denotes (inactive) HSPs that are attached to heat shock factor monomers; HSF denotes a monomer of heat shock factor; $HSF_3$ denotes a trimer of heat shock factor that can penetrate the nuclear membrane to interact with a heat shock element on the DNA molecule; $HSE:HSF_3$ denotes a trimer of heat shock factor attached to a heat shock element on the DNA molecule that initiates transcription of a new mRNA molecule; mRNA denotes the messenger RNA molecule that results from the $HSE:HSF_3$, and that leads to the production of a new (activated) HSP molecule in the cell's cytoplasm.

FIG. 55 shows that initially the concentration of activated HSPs is the result of release of HSPs sequestered in the molecules HSPHSF in the cytoplasm, with the creation of new HSPs from the cell nucleus via mRNA not occurring until 60 minutes after the temperature rise occurs. FIG. 55 also shows that the activated HSPs are very rapidly attached to damaged proteins to begin their repair work. For the cell depicted, the sudden rise in temperature also results in a temporary rise in damaged protein concentration, with the peak in the damaged protein concentration occurring about 30 minutes after the temperature increase.

FIG. 55 shows what the Rybinski et al equations predict for the variation of the 10 different species over a period of 350 minutes. However, the present invention is concerned with SDM application is on the variation of the species over the much shorter O(minute) interval between two applications of SDM at any single retinal locus. It will be understood that the preferred embodiment of SDM in the form of laser light treatment is analyzed and described, but it is applicable to other sources of energy as well.

With reference now to FIGS. 56A-56H, the behavior of HSP cellular system components during the first minute following a sudden increase in temperature from 37° C. to 42° C. using the Rybinski et al. (2013) equations with the initial values and rate constants of Tables 5 and 6 are shown. The abscissa denotes time in minutes, and the ordinate shows concentration in the same arbitrary units as in FIG. 56.

FIG. 56 shows that the nuclear source of HSPs plays virtually no role during a 1 minute period, and that the main source of new HSPs in the cytoplasm arises from the release of sequestered HSPs from the reservoir of HSPHSF molecules. It also shows that a good fraction of the newly activated HSPs attach themselves to damaged proteins to begin the repair process.

The initial concentrations in Table 5 are not the equilibrium values of the species, i.e. they do not give d[ . . . ]/dt=0, as evidenced by the curves in FIGS. 55 and 56. The equilibrium values that give d[ . . . ]/dt=0 corresponding to the rate constants of Table 6 are found to be those listed in Table 7.

TABLE 7

Equilibrium values of species in arbitrary units [Rybinski et al (2013)] corresponding to the rate constants of Table 6. The arbitrary units are those chosen by Rybinski et al for computational convenience: to make the quantities of interest in the range of 0.01-10.

| | |
|---|---|
| [HSP(equil)] | 0.315343 |
| [HSF(equil)] | 0.255145 |
| [S(equil)] | 0.542375 |
| [HSPHSF(equil)] | 1.982248 |
| [HSPS(equil)] | 5.05777 |
| [$HSF_3$(equil)] | 0.210688 |
| [HSE(equil)] | 0.206488 |
| [$HSF_3$HSE(equil)] | 0.643504 |
| [mRNA(equil)] | 0.1171274 |
| [P(equil)] | 4.39986 |

Note that the equilibrium concentration of HSPs is 100× {0.315343/(4.39986+5.05777+0.542375)}=3.15% of the total number of proteins present in the cell. This is comparable, but less than the anticipated 5%-10% total number of proteins found by other researchers. However, we have not attempted to adjust percentage upwards expecting that the general behavior will not be appreciably changed as indicated by other researchers.

The inventors have found that a first treatment to the target tissue may be performed by repeatedly applying the pulsed energy (e.g., SDM) to the target tissue over a period of time so as to controllably raise a temperature of the target tissue to therapeutically treat the target tissue without destroying or permanently damaging the target tissue. A "treatment" comprises the total number of applications of the pulsed energy to the target tissue over a given period of time, such as dozens or even hundreds of light or other energy applications to the target tissue over a short period of time, such as a period of less than ten seconds, and more typically a period of less than one second, such as 100 milliseconds to 600 milliseconds. This "treatment" controllably raises the temperature of the target tissue to activate the heat shock proteins and related components.

What has been found, however, is that if the application of the pulsed energy to the target tissue is halted for an interval of time, such as an interval of time that exceeds the first period of time comprising the "first treatment", which may comprise several seconds to several minutes, such as three seconds to three minutes or more preferably ten seconds to ninety seconds, and then a second treatment is performed on the target tissue after the interval of time within a single treatment session or office visit, wherein the second treatment also entails repeatedly reapplying the pulsed energy to the target tissue so as to controllably raise the temperature of the target tissue to therapeutically treat the target tissue without destroying or permanently damaging the target tissue, the amount of activated HSPs and related components in the cells of the target tissue is increased resulting in a more effective overall treatment of the biological tissue. In other words, the first treatment creates a level of heat shock protein activation of the target tissue, and the second treatment increases the level of heat shock protein activation in the target tissue above the level due to the first treatment. Thus, performing multiple treatments to the target tissue of the patient within a single treatment session or office visit enhances the overall treatment of the biological tissue so long as the second or additional treatments are performed after an interval of time which does not exceed several minute but which is of sufficient length so as to allow temperature relaxation so as not to damage or destroy the target tissue.

This technique may be referred to herein as "stair-stepping" in that the levels of activated HSP production increase with the subsequent treatment or treatments within the same office visit treatment session. This "stair-stepping" technique may be described by a combination of the Arrhenius integral approach for subsecond phenomena with the Rybinski et al. (2013) treatment of intervals between repeated subsecond applications of the SDM or other pulsed energy.

For the proposed stair-stepping SDM (repetitive SDM applications) proposed in this invention disclosure, there are some important differences from the situation depicted in FIG. 55:

SDM can be applied prophylactically to a healthy cell, but oftentimes SDM will be applied to a diseased cell. In that case, the initial concentration of damaged proteins [S(0)] can be larger than given in Table 7. We shall not attempt to account for this, assuming that the qualitative behavior will not be changed.

The duration of a single SDM application is only subseconds, rather than the minutes shown in FIG. 55. The Rybinski et al rate constants are much smaller than the Arrhenius constants: the latter give Arrhenius integrals of the order of unity for subsecond durations, whereas the Rybinski et al rate constants are too small to do that. This is an example of the different effective rate constants that exist when the time scales of interest are different: The Rybinski et al rate constants apply to phenomena occurring over minutes, whereas the Arrhenius rate constants apply to subsecond phenomena.

Accordingly, to analyze what happens in the proposed stair-stepping SDM technique for improving the efficacy of SDM, we shall combine the Arrhenius integral treatment appropriate for the subsecond phenomena with the Rybinski et al (2013) treatment appropriate for the phenomena occurring over the order of a minute interval between repeated SDM applications:

SDM subsecond application described by Arrhenius integral formalism

Interval of O(minute) between SDM applications described by Rybinski et al (2013) equations Specifically, we consider two successive applications of SDM, each SDM micropulse train having a subsecond duration.

For the short subsecond time scale, we assume that the unactivated HSP's that are the source of the activated (free) HSP's are all contained in the HSPHSF molecules in the cytoplasm. Accordingly, the first SDM application is taken to reduce the cytoplasmic reservoir of unactivated HSPs in the initial HSPHSF molecule population from

[HSPHSF(equil)] to [HSPHSF(equil)]exp[$-\Omega$], and to increase the initial HSP molecular population from

[HSP(equil)] to [HSP(equil)]+[HSPHSF(equil)](1$-$exp[$-\Omega$])

as well as to increase the initial HSF molecular population from

[HSF(equil)] to [HSF(equil)]+[HSPHSF(equil)](1$-$exp[$-\Omega$])

The equilibrium concentrations of all of the other species will be assumed to remain the same after the first SDM application The Rybinski et al equations are then used to calculate what happens to [HSP] and [HSPHSF] in the interval $\Delta t=O$(minute) between the first SDM application and the second SDM application, with the initial values of HSP, HSF and HSPHSF after the first SDM application taken to be

[HSP(SDM1)]=[HSP(equil)]+[HSPHSF(equil)](1$-$exp[$-\Omega$])

[HSF(SDM1)]=[HSF(equil)]+[HSPHSF(equil)](1$-$exp[$-\Omega$])

and

[HSPHSF(SDM1)]=[HSPHSF(equil)]exp[$-\Omega$]

For the second application of SDM after the interval $\Delta t$, the values of [HSP], [HSF] and {HSPHSF] after the SDM will be taken to be

[HSP(SDM2)]=[HSP($\Delta t$)]+[HSPHSF($\Delta t$)](1$-$exp[$-\Omega$])

[HSF(SDM2)]=[HSF($\Delta t$)]+[HSPHSF($\Delta t$)](1$-$exp[$-\Omega$])

and

[HSPHSF(SDM2)]=[HSPHSF($\Delta t$)]exp[$-\Omega$]

where [HSP($\Delta t$)], [HSF($\Delta t$)], and [HSPHSF($\Delta t$)] are the values determined from the Rybinski et al (2013) equations at the time $\Delta t$.

Our present interest is in comparing [HSP[SDM2)] with [HSP[SDM1)], to see if the repeated application of SDM at an interval $\Delta t$ following the first application of SDM has resulted in more activated (free) HSP's in the cytoplasm. The ratio $\beta(\Delta t, \Omega)$=[HSP(SDM2)]/[HSP(SDM1)]={[{[HSP($\Delta t$)]+[HSPHSF($\Delta t$)](1$-$exp[$-\Omega$])}/{[HSP(0)]+[HSPHSF(0)](1$-$exp[$-\Omega$])} provides a direct measure of the improvement in the degree of HSP activation for a repeated application of SDM after an interval $\Delta t$ from the first SDM application.

The HSP and HSPHSF concentrations can vary quite a bit in the interval $\Delta t$ between SDM applications.

Figure 57A:
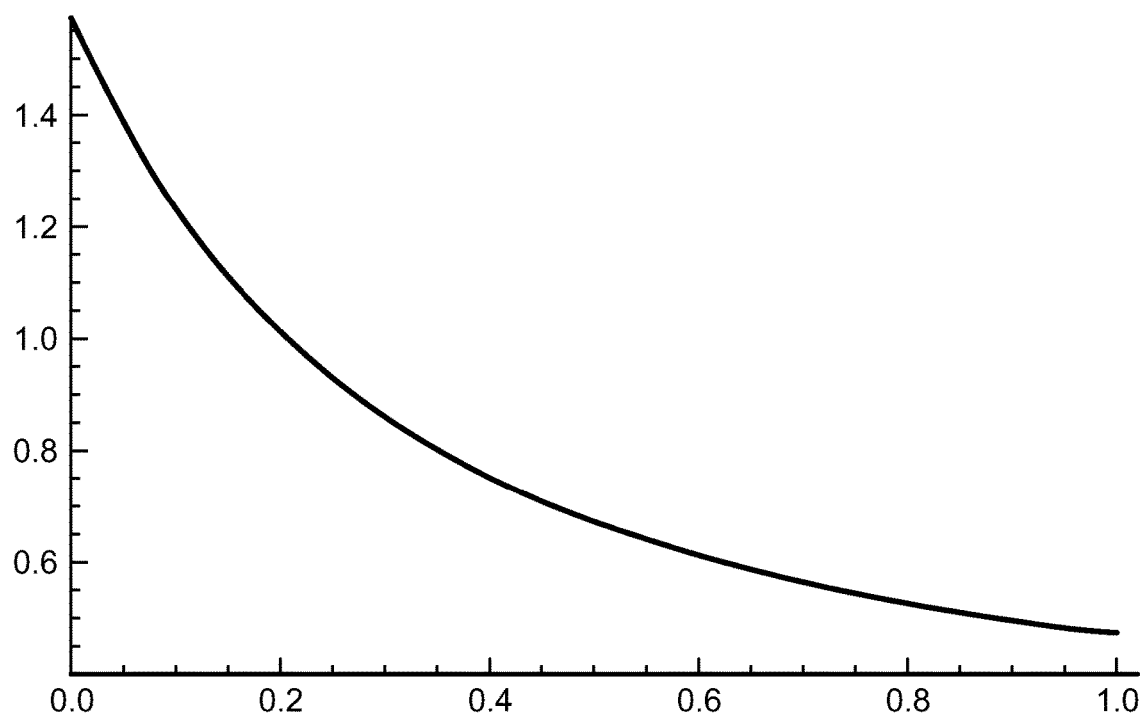
FIGS. 57A and 57B are graphs illustrating variation in the activated concentrations of HSP and unactivated HSP in the cytoplasmic reservoir over an interval of one minute, in accordance with the present invention.
Figure 57B:
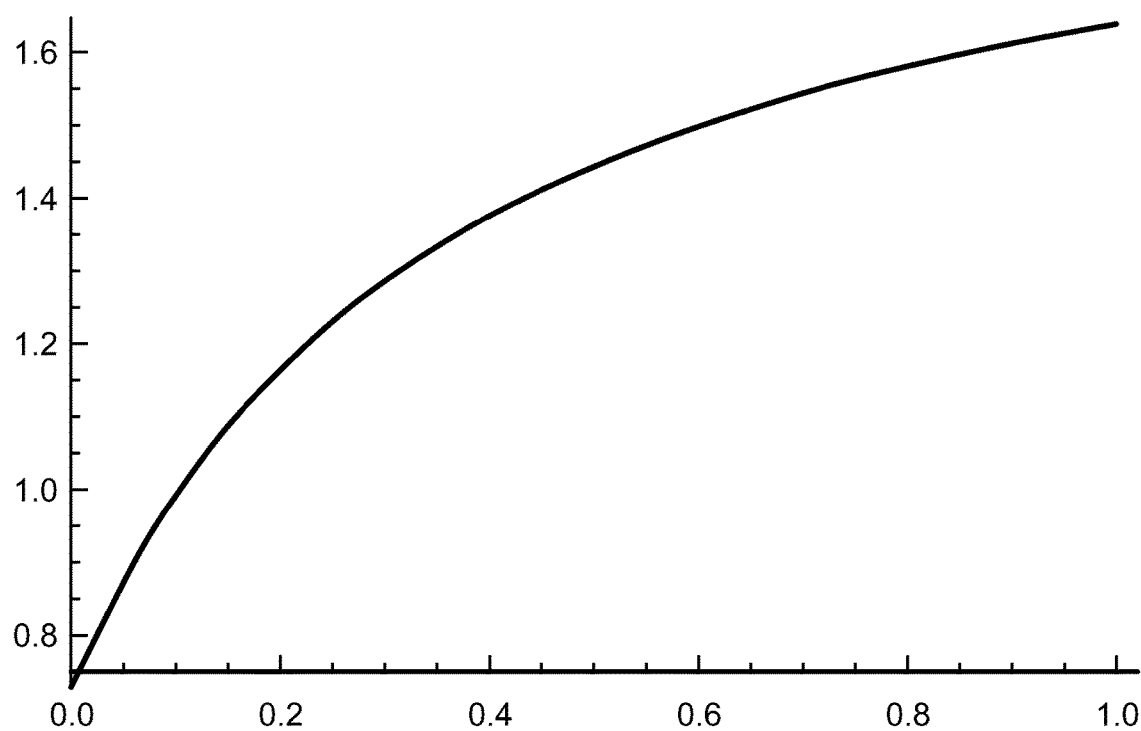

FIGS. 57A and 57B illustrate the variation in the activated concentrations [HSP] and the unactivated HSP in the cytoplasmic reservoir [HSPHSF] during an interval $\Delta t=1$ minute between SDM applications when the SDM Arrhenius integral $\Omega=1$ and the equilibrium concentrations are as given in Table 7.

Although only a single repetition (one-step) is treated here, it is apparent that the procedure could be repeated to provide a multiple stair-stepping events as a means of improving the efficacy of SDM, or other therapeutic method involving activation of tissue HSPs.

Effects of varying the magnitude of the Arrhenius integral $\Omega$ and interval $\Delta t$ between two distinct treatments separated by an interval of time are shown by the following examples and results.

Nine examples generated with the procedure described above are presented in the following. All of the examples are of a treatment consisting of two SDM treatments, with the second occurring at a time $\Delta t$ following the first, and they explore:

The effect of different magnitude Arrhenius integrals Ω in the SDM treatments [Three different Ω's are considered: Ω=0.2, 0.5 and 1.0]

The impact of varying the interval Δt between the two SDM treatments [Three different Δt's are considered: Δt=15 sec., 30 sec., and 60 sec.

As indicated above, the activation Arrhenius integral Ω depends on both the treatment parameters (e.g., laser power, duty cycle, total train duration) and on the RPE properties (e.g., absorption coefficients, density of HSPs).

Table 8 below shows the effect of different Ω (Ω=0.2, 0.5, 1) on the HSP content of a cell when the interval between the two SDM treatments is Δt=1 minute. Here the cell is taken to have the Rybinski et al (2013) equilibrium concentrations for the ten species involved, given in Table 7.

Table 8 shows four HSP concentrations (in the Rybinski et al arbitrary units) each corresponding to four different times:

Before the first SDM treatment: [HSP(equil)]

Immediately after the first SDM application: [HSP(SDM1)]

At the end of the interval Δt following the first SDM treatment: [HSP(Δt)]

Immediately after the second SDM treatment at Δt: [HSP(SDM2)]

Also shown is the improvement factor over a single treatment: β=[HSP(SDM2)]/[HSP(SDM1)]

TABLE 8

HSP concentrations at the four times just described in the text: Effect of varying the SDM Ω for two SDM applications on a cell when the treatments are separated by Δt = 0.25 minutes = 15 seconds.

|   | $[HSP_{(equil)}]$ | $[HSP_{(SDM1)}]$ | $[HSP_{(\Delta t)}]$ | $[HSP_{(SDM2)}]$ | β |
|---|---|---|---|---|---|
| Ω = 0.2 | 0.315 | 0.67 | 0.54 | 0.95 | 1.27 |
| Ω = 0.5 | 0.315 | 1.10 | 0.77 | 1.34 | 1.22 |
| Ω = 1.0 | 0.315 | 1.57 | 0.93 | 1.71 | 1.09 |

Table 9 is the same as Table 8, except that it is for an interval between SDM treatments of Δt=0.5 minutes=30 seconds.

TABLE 9

HSP concentrations at the four times described in the text: Effect of varying the SDM Ω for two SDM treatments on a cell when the treatments are separated by Δt = 0.5 minutes = 30 seconds.

|   | $[HSP_{(equil)}]$ | $[HSP_{(SDM1)}]$ | $[HSP_{(\Delta t)}]$ | $[HSP_{(SDM2)}]$ | β |
|---|---|---|---|---|---|
| Ω = 0.2 | 0.315 | 0.67 | 0.44 | 0.77 | 1.14 |
| Ω = 0.5 | 0.315 | 1.10 | 0.58 | 1.18 | 1.08 |
| Ω = 1.0 | 0.315 | 1.57 | 0.67 | 1.59 | 1.01 |

Table 10 is the same as the Tables 8 and 9, except that the treatments are separated by one minute, or sixty seconds.

TABLE 10

HSP concentrations at the four times just described in the text: Effect of varying the SDM Ω for two SDM treatments on a normal (healthy) cell when the treatments are separated by Δt = 1 minute = 60 seconds.

|   | $[HSP_{(equil)}]$ | $[HSP_{(SDM1)}]$ | $[HSP_{(\Delta t)}]$ | $[HSP_{(SDM2)}]$ | β |
|---|---|---|---|---|---|
| Ω = 0.2 | 0.315 | 0.67 | 0.30 | 0.64 | 0.95 |
| Ω = 0.5 | 0.315 | 1.10 | 0.37 | 1.06 | 0.96 |
| Ω = 1.0 | 0.315 | 1.57 | 0.48 | 1.51 | 0.96 |

Tables 8-10 show that:

The first treatment of SDM increases [HSP] by a large factor for all three Ω's, although the increase is larger the larger Ω. Although not displayed explicitly in the tables, the increase in [HSP] comes at the expense of the cytoplasmic reservoir of sequestered (unactivated) HSP's: [HSPHSF(SDM1)] is much smaller than [HSPHSF(equil)]

[HSP] decreases appreciably in the interval Δt between the two SDM treatments, with the decrease being larger the larger Δt is. (The decrease in [HSP] is accompanied by an increase in both [HSPHSF]—as shown in FIG. 44 and in [HSPS] during the interval Δt—indicating a rapid replenishment of the cytoplasmic reservoir of unactivated HSP's and a rapid attachment of HSP's to the damaged proteins.)

For Δt less than 60 seconds, there is an improvement in the number of activated (free) HSP's in the cytoplasm for two SDM treatments rather than a single treatment.

The improvement increases as Δt becomes smaller.

For Δt becoming as large as 60 seconds, however, the ratio β=[HSP(SDM2)]/[HSP(SDM1)] becomes less than unity, indicating no improvement in two SDM treatments compared to a single SDM treatment although this result can vary depending on energy source parameters and tissue type that is treated.

The improvement for Δt<60 seconds is larger the smaller the SDM Arrhenius integral Ω is.

The results for the improvement ratio β=[HSP(SDM2)]/[HSP(SDM1)] are summarized in FIG. 45, where the improvement ratio β=[HSP(SDM2)]/[HSP(SDM1)]vs. interval between SDM treatments Δt (in seconds) for three values of the SDM Arrhenius integral Ω, and for the three values of the interval Δt=15 sec, 30 sec, and 60 sec. The uppermost curve is for Ω=0.2; the middle curve is for Ω=0.5; and the bottom curve is for Ω=1.0. These results are for the Rybinski et al (2013) rate constants of Table 6 and the equilibrium species concentrations of Table 4.

Figure 58:
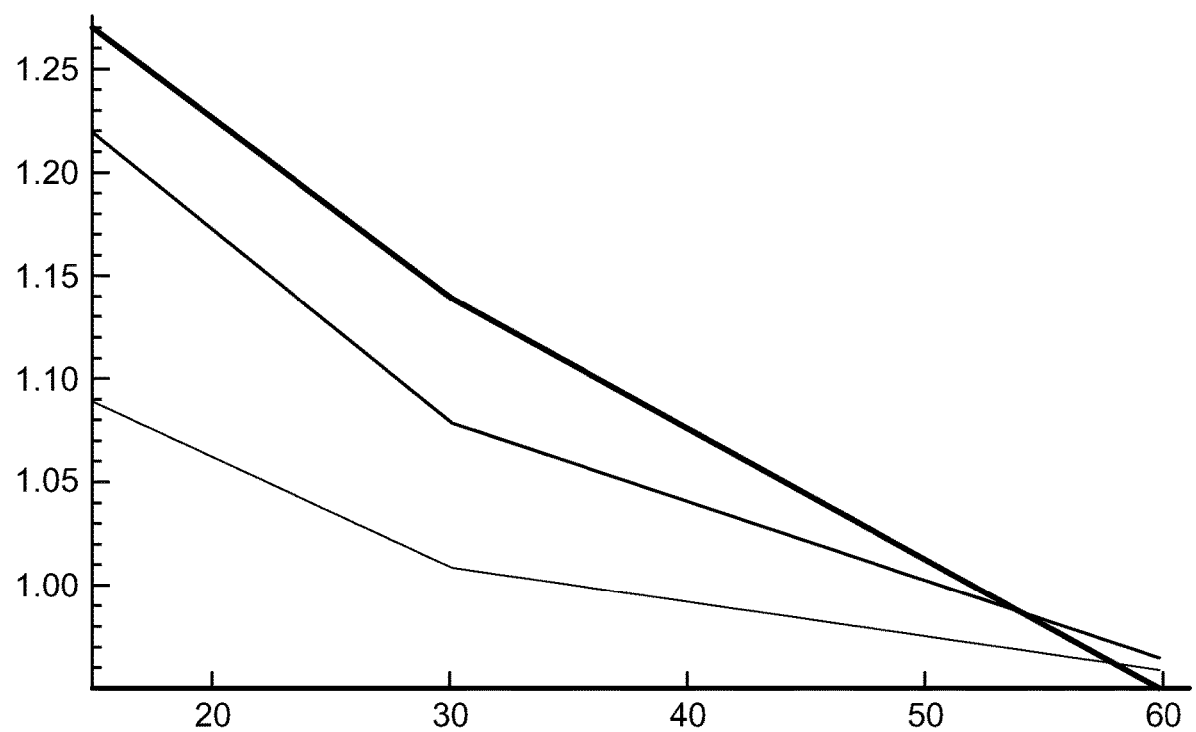
FIG. 58 is a graph depicting the improvement ratios versus interval between treatments, in accordance with the present invention.

It should be appreciated that results of Tables 8-10 and FIG. 58 are for the Rybinski et al. (2013) rate constants of Table 6 and the equilibrium concentrations of Table 7. The actual concentrations and rate constants in a cell may differ from these values, and thus the number results in Tables 8-10 and FIG. 58 should be taken as representative rather than absolute. However, they are not anticipated to be significantly different. Thus, performing multiple intra-sessional treatments on a single target tissue location or area, such as a single retinal locus, with the second and subsequent treatments following the first after an interval anywhere from three seconds to three minutes, and preferably ten seconds to ninety seconds, should increase the activation of HSPs and related components and thus the efficacy of the overall treatment of the target tissue. The resulting "stair-stepping" effect achieves incremental increases in the number of heat shock proteins that are activated, enhancing the therapeutic effect of the treatment. However, if the interval of time between the first and subsequent treatments is too great, then the "stair-stepping" effect is lessened or not achieved.

The technique of the present invention is especially useful when the treatment parameters or tissue characteristics are such that the associated Arrhenius integral for activation is low, and when the interval between repeated applications is small, such as less than ninety seconds, and preferably less than a minute. Accordingly, such multiple treatments must be performed within the same treatment session, such as in a single office visit, where distinct treatments can have a window of interval of time between them so as to achieve the benefits of the technique of the present invention.

Although several embodiments have been described in detail for purposes of illustration, various modifications may be made without departing from the scope and spirit of the invention. Accordingly, the invention is not to be limited, except as by the appended claims.

What is claimed is:

1. A process for heat treating biological tissue, comprising the steps of:
    providing a plurality of energy emitters formed into an array;
    generating treatment energy comprising microwave energy from the plurality of emitters;
    providing an initial treatment to the target tissue by repeatedly applying the energy to the target tissue in a pulsed manner for the exposure duration comprising less than one second;
    halting application of the pulsed energy to the target tissue for an interval of time comprising between three seconds and three minutes; and
    providing a secondary treatment to the target tissue after the interval of time, within a single treatment session, by repeatedly reapplying the pulsed energy for the exposure duration comprising less than one second;
    wherein the treatment energy has energy and application parameters selected so as to raise the target tissue temperature sufficiently to create a therapeutic effect while maintaining an average temperature of the target tissue over several minutes at or below a predetermined temperature so as to not destroy or permanently damage the target tissue.

2. The process of claim 1, wherein the selected energy and application parameters comprise tissue application spot size or area, average power or average power density, and exposure duration.

3. The process of claim 1, wherein during an interval of time, comprising less than one second, between applications of energy applied to a first area of the target tissue, applying treatment energy to a second area of the target tissue sufficiently spaced apart from the first area of the target tissue to avoid thermal tissue damage of the target tissue.

4. The process of claim 3, wherein repeatedly applying, in an alternating manner during the same treatment session, the treatment energy to each of the first and second areas of the target tissue until a predetermined number of energy applications to each of the first and second areas of the target tissue has been achieved.

5. The process of claim 3, including the step of introducing a phase delay in the activation of the energy emitters of the array to generate treatment energy in a phased manner using a predetermined delay of activation in order to apply treatment energy to each of the first and second areas of the target tissue.

6. The process of claim 3, including the step of activating the energy emitters of the array sequentially in order to apply treatment energy to each of the first and second areas of the target tissue.

7. The process of claim 1, wherein the treatment energy raises the target tissue to up to eleven degrees Celsius at least during application of the pulsed treatment energy thereto.

8. The process of claim 1, wherein the average target tissue temperature is maintained at six degrees Celsius or less over several minutes.

9. The process of claim 8, wherein the average target tissue temperature is maintained at one degree Celsius or less over several minutes.

10. The process of claim 1, wherein the applying step comprises the step of stimulating heat shock protein activation in the target tissue.

11. The process of claim 1, wherein the treatment energy and application parameters are selected to have an average power density of 100-590 watts/square centimeter of target tissue, a spot size between 100-500 microns, and a train exposure duration of 500 milliseconds or less.

12. The process of claim 1, wherein the microwave energy comprises a microwave frequency between approximately 10 to 20 GHz and a duty cycle between approximately 2% to 5% and an average power of approximately 8 and 52 watts.

* * * * *